(12) United States Patent
Bearss et al.

(10) Patent No.: US 11,793,802 B2
(45) Date of Patent: Oct. 24, 2023

(54) TREATMENT OF ACUTE MYELOID LEUKEMIA (AML) WITH VENETOCLAX FAILURE

(71) Applicant: Sumitomo Pharma Oncology, Inc., Marlborough, MA (US)

(72) Inventors: David J. Bearss, Alpine, UT (US); Stephen Patrick Anthony, Herber City, UT (US); Michael Vincent McCullar, Walnut Creek, CA (US); Susan Carol Smith, San Antonio, TX (US)

(73) Assignee: Sumitomo Pharma Oncology, Inc., Marlborough, MA (US)

( * ) Notice: Subject to any disclaimer, the term of this patent is extended or adjusted under 35 U.S.C. 154(b) by 123 days.

(21) Appl. No.: 17/435,264

(22) PCT Filed: Mar. 20, 2020

(86) PCT No.: PCT/US2020/023939
§ 371 (c)(1),
(2) Date: Aug. 31, 2021

(87) PCT Pub. No.: WO2020/191326
PCT Pub. Date: Sep. 24, 2020

(65) Prior Publication Data
US 2022/0125776 A1  Apr. 28, 2022

Related U.S. Application Data

(60) Provisional application No. 62/871,934, filed on Jul. 9, 2019, provisional application No. 62/821,342, filed on Mar. 20, 2019.

(51) Int. Cl.
| | |
|---|---|
| *A01N 43/04* | (2006.01) |
| *A61K 31/70* | (2006.01) |
| *A61K 31/453* | (2006.01) |
| *A61P 35/02* | (2006.01) |
| *A61K 9/00* | (2006.01) |
| *A61K 31/7068* | (2006.01) |

(52) U.S. Cl.
CPC .......... *A61K 31/453* (2013.01); *A61K 9/0019* (2013.01); *A61K 31/7068* (2013.01); *A61P 35/02* (2018.01)

(58) Field of Classification Search
None
See application file for complete search history.

(56) References Cited

U.S. PATENT DOCUMENTS

| | | |
|---|---|---|
| 4,132,710 A | 1/1979 | Gauthier et al. |
| 4,146,629 A | 3/1979 | Kubela et al. |
| 4,522,811 A | 6/1985 | Epstein et al. |
| 4,676,980 A | 6/1987 | Segal et al. |
| 4,816,567 A | 3/1989 | Cabilly et al. |
| 4,900,727 A | 2/1990 | Kattige |
| 4,946,778 A | 8/1990 | Ladner et al. |
| 4,971,909 A | 11/1990 | Kaneoya et al. |
| 5,225,539 A | 7/1993 | Winter |
| 5,284,856 A | 2/1994 | Naik et al. |
| 5,310,763 A | 5/1994 | Campion et al. |
| 5,545,806 A | 8/1996 | Lonberg et al. |
| 5,545,807 A | 8/1996 | Surani et al. |
| 5,569,825 A | 10/1996 | Lonberg et al. |
| 5,587,458 A | 12/1996 | King et al. |
| 5,625,126 A | 5/1997 | Lonberg et al. |
| 5,663,425 A | 5/1997 | Lonberg et al. |
| 5,661,016 A | 8/1997 | Lonberg et al. |
| 5,674,980 A | 10/1997 | Frankel et al. |
| 5,747,498 A | 5/1998 | Schnur et al. |
| 5,792,783 A | 8/1998 | Tang et al. |
| 5,804,604 A | 9/1998 | Frankel et al. |
| 5,834,504 A | 11/1998 | Tang et al. |
| 5,849,733 A | 12/1998 | Kim |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,020 A | 3/1999 | Tang et al. |
| 5,908,934 A | 6/1999 | Kim |
| 5,916,771 A | 6/1999 | Hori et al. |
| 5,932,595 A | 8/1999 | Bender et al. |
| 5,939,598 A | 8/1999 | Kucherlapati et al. |
| 5,965,703 A | 10/1999 | Horne et al. |
| 6,077,864 A | 6/2000 | Burgess et al. |
| 6,087,366 A | 7/2000 | Park et al. |
| 6,087,392 A | 7/2000 | Reiter |
| 6,090,852 A | 7/2000 | Dack et al. |
| 6,110,964 A | 8/2000 | Robinson |
| 6,136,981 A | 10/2000 | Brion et al. |

(Continued)

FOREIGN PATENT DOCUMENTS

| | | | |
|---|---|---|---|
| CA | 2929652 A1 | 5/2015 | |
| CN | 1583776 A | 2/2005 | |

(Continued)

OTHER PUBLICATIONS

Zeidner, Joshua F., and Judith E. Karp. "Clinical activity of alvocidib (flavopiridol) in acute myeloid leukemia." Leukemia research 39.12 (2015): 1312-1318.*

(Continued)

*Primary Examiner* — Patrick T Lewis
(74) *Attorney, Agent, or Firm* — Hamilton, Brook, Smith & Reynolds, P.C.

(57) ABSTRACT

Provided herein are various regimens for treating acute myeloid leukemia (AML) in subjects (e.g, patients) who have undergone one or more prior anti-AML therapies involving venetoclax, and have shown disease progression after the one or more prior therapies. The treatment regimens disclosed herein involve alvocidib, either as a monotherapy, or in combination with cytarabine or a hypomethylating agent, such as decitabine or azacitidine. The treatment regimens disclosed herein do not involve combination therapy of alvocidib with venetoclax.

20 Claims, No Drawings

(56) References Cited

U.S. PATENT DOCUMENTS

| | | |
|---|---|---|
| 6,147,061 A | 11/2000 | Reiter |
| 6,153,609 A | 11/2000 | Robinson et al. |
| 6,177,401 B1 | 1/2001 | Ullrich et al. |
| 6,207,669 B1 | 3/2001 | Cockerill et al. |
| 6,214,872 B1 | 4/2001 | Robinson |
| 6,225,473 B1 | 5/2001 | Breipohl et al. |
| 6,258,540 B1 | 7/2001 | Lo et al. |
| 6,284,764 B1 | 9/2001 | Kath et al. |
| 6,291,455 B1 | 9/2001 | Thomas et al. |
| 6,294,532 B1 | 9/2001 | Thomas et al. |
| 6,303,636 B1 | 10/2001 | Robinson, Jr. et al. |
| 6,362,336 B1 | 3/2002 | Lohmann et al. |
| 6,399,633 B1 | 6/2002 | Dumont et al. |
| 6,406,912 B1 | 6/2002 | Holla |
| 6,437,136 B2 | 8/2002 | Breipohl et al. |
| 6,492,383 B1 | 12/2002 | Munchhof et al. |
| 6,495,568 B1 | 12/2002 | Dack et al. |
| 6,511,993 B1 | 1/2003 | Dack et al. |
| 6,576,647 B2 | 6/2003 | Bafus et al. |
| 6,596,726 B1 | 7/2003 | Bridges et al. |
| 6,599,890 B1 | 7/2003 | McClure et al. |
| 6,723,726 B1 | 4/2004 | Cockerill et al. |
| 6,821,990 B2 | 11/2004 | Kessler |
| 6,828,320 B2 | 12/2004 | Cockerill et al. |
| 6,849,631 B2 | 2/2005 | Carini |
| 7,064,193 B1 | 6/2006 | Cory et al. |
| 7,119,090 B2 | 10/2006 | Tang et al. |
| 7,332,582 B2 | 2/2008 | Hardy et al. |
| 7,417,055 B2 | 8/2008 | Cannizzaro et al. |
| 7,452,901 B2 | 11/2008 | Boojamra et al. |
| 7,488,802 B2 | 2/2009 | Collins et al. |
| 7,572,924 B2 | 8/2009 | Tang et al. |
| 7,695,715 B2 | 4/2010 | Hardy et al. |
| 7,714,005 B2 | 5/2010 | Chen et al. |
| 7,790,902 B2 | 9/2010 | Larson et al. |
| 7,816,398 B2 | 10/2010 | Swindell et al. |
| 7,829,662 B2 | 11/2010 | Korsmeyer et al. |
| 7,868,133 B2 | 1/2011 | Korsmeyer et al. |
| 7,884,127 B2 | 2/2011 | Lal et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,168,755 B2 | 5/2012 | Cardone et al. |
| 8,217,149 B2 | 7/2012 | Irving et al. |
| 8,221,966 B2 | 7/2012 | Letai |
| 8,304,449 B2 | 11/2012 | Lal et al. |
| 8,354,509 B2 | 1/2013 | Craven et al. |
| 8,372,819 B2 | 2/2013 | Jones et al. |
| 8,460,927 B2 | 6/2013 | Chen |
| 8,552,154 B2 | 10/2013 | Freeman et al. |
| 8,552,156 B2 | 10/2013 | Takayanagi et al. |
| 8,686,119 B2 | 4/2014 | Roten-Yehudar et al. |
| 8,735,553 B1 | 5/2014 | Li et al. |
| 8,758,752 B2 | 6/2014 | Govindan et al. |
| 8,779,108 B2 | 7/2014 | Queva et al. |
| 8,822,526 B2 | 9/2014 | Rathos et al. |
| 8,841,418 B2 | 9/2014 | Karsunky et al. |
| 8,907,053 B2 | 12/2014 | Sasikumar et al. |
| 8,927,697 B2 | 1/2015 | Davis et al. |
| 8,975,239 B2 | 3/2015 | Green et al. |
| 8,993,731 B2 | 3/2015 | Tyson |
| 9,102,727 B2 | 8/2015 | Freeman et al. |
| 9,138,485 B2 | 9/2015 | Govindan et al. |
| 9,163,087 B2 | 10/2015 | Kuchroo et al. |
| 9,175,082 B2 | 11/2015 | Zhou et al. |
| 9,199,973 B2 | 12/2015 | Carter et al. |
| 9,205,148 B2 | 12/2015 | Langermann et al. |
| 9,241,941 B2 | 1/2016 | Wendal et al. |
| 9,244,059 B2 | 1/2016 | Triebel et al. |
| 9,340,524 B2 | 5/2016 | Chen et al. |
| 9,360,473 B2 | 6/2016 | Cardone |
| 9,493,454 B2 | 11/2016 | Zeng et al. |
| 9,505,839 B2 | 11/2016 | Lonberg et al. |
| 9,540,674 B2 | 1/2017 | Letai |
| 9,605,070 B2 | 3/2017 | Seabatos-Peyton et al. |
| 9,683,048 B2 | 6/2017 | Freeman et al. |
| 9,758,539 B2 | 9/2017 | Siddiqui-Jain et al. |
| 9,856,303 B2 | 1/2018 | Korsmeyer et al. |
| 9,901,574 B2 | 2/2018 | Warner et al. |
| 9,902,759 B2 | 2/2018 | Korsmeyer et al. |
| 9,925,192 B2 | 3/2018 | Strack et al. |
| 9,988,452 B2 | 6/2018 | Freeman et al. |
| 10,132,797 B2 | 11/2018 | Bearss et al. |
| 10,259,835 B2 | 4/2019 | Siddiqui-Jain et al. |
| 10,267,787 B2 | 4/2019 | Bearss et al. |
| 10,357,488 B2 | 7/2019 | Warner et al. |
| 10,422,788 B2 | 9/2019 | Bearss et al. |
| 10,562,925 B2 | 2/2020 | Siddiqui-Jain et al. |
| 10,568,887 B2 | 2/2020 | Bearss et al. |
| 10,624,880 B2 | 4/2020 | Warner et al. |
| 10,682,356 B2 | 6/2020 | Bearss et al. |
| 10,793,915 B2 | 10/2020 | Dettman et al. |
| 10,835,537 B2 | 11/2020 | Bearss et al. |
| 11,034,710 B2 | 6/2021 | Siddiqui-Jain et al. |
| 11,279,694 B2 | 3/2022 | Siddiqui-Jain et al. |
| 11,497,756 B2 | 11/2022 | Bearss et al. |
| 11,530,231 B2 | 12/2022 | Siddiqui-Jain et al. |
| 2001/0021704 A1 | 9/2001 | Ghyczy et al. |
| 2002/0016293 A1 | 2/2002 | Ratain et al. |
| 2002/0115613 A1 | 8/2002 | Kumar |
| 2002/0177609 A1 | 11/2002 | Swindell et al. |
| 2003/0065023 A1 | 4/2003 | Swindell et al. |
| 2003/0073661 A1 | 4/2003 | Matsuyama et al. |
| 2003/0119816 A1 | 6/2003 | Haesslein et al. |
| 2004/0106647 A1 | 6/2004 | Schneider et al. |
| 2004/0171809 A1 | 9/2004 | Korsmeyer et al. |
| 2004/0235783 A1 | 11/2004 | Ghyczy et al. |
| 2005/0026959 A1 | 2/2005 | Kesseler |
| 2005/0153991 A1 | 7/2005 | Gianella-Borradori et al. |
| 2007/0093490 A1 | 4/2007 | Prien et al. |
| 2008/0027105 A1 | 1/2008 | Suarez et al. |
| 2008/0108657 A1 | 5/2008 | Kesseler |
| 2009/0030005 A1 | 1/2009 | Kamb et al. |
| 2009/0142337 A1 | 6/2009 | Squires |
| 2010/0143350 A1 | 6/2010 | Green et al. |
| 2010/0286057 A1 | 11/2010 | Walensky et al. |
| 2011/0008371 A1 | 1/2011 | Michelson |
| 2011/0251240 A1 | 10/2011 | Suarez et al. |
| 2012/0225851 A1 | 9/2012 | Cardone et al. |
| 2013/0079424 A1 | 3/2013 | Gerber et al. |
| 2013/0122492 A1 | 5/2013 | Khosravi et al. |
| 2013/0210024 A1 | 8/2013 | Yu et al. |
| 2014/0140956 A1 | 5/2014 | Fairfax et al. |
| 2014/0286861 A1 | 9/2014 | Govindan et al. |
| 2014/0303167 A1 | 10/2014 | Choidas et al. |
| 2015/0051249 A1 | 2/2015 | Walensky et al. |
| 2015/0150869 A1 | 6/2015 | Cardone et al. |
| 2015/0259420 A1 | 9/2015 | Triebel et al. |
| 2015/0301053 A1 | 10/2015 | Pierceall et al. |
| 2015/0352097 A1 | 12/2015 | Cardone et al. |
| 2015/0362479 A1 | 12/2015 | Letai et al. |
| 2016/0178612 A1 | 6/2016 | Cardone |
| 2016/0231314 A1 | 8/2016 | Ryan et al. |
| 2016/0235779 A1 | 8/2016 | Marcus |
| 2016/0258933 A1 | 9/2016 | Letai |
| 2016/0273020 A1 | 9/2016 | Pierceall et al. |
| 2016/0279106 A1 | 9/2016 | Udea et al. |
| 2017/0184567 A1 | 6/2017 | Letai |
| 2017/0260268 A1 | 9/2017 | Beatty et al. |
| 2018/0280407 A1 | 10/2018 | Warner et al. |
| 2019/0314357 A1 | 10/2019 | Bearss et al. |
| 2020/0048228 A1 | 2/2020 | Siddiqui-Jain et al. |
| 2020/0131210 A1 | 4/2020 | Siddiqui-Jain et al. |
| 2020/0200737 A1 | 6/2020 | Bearss et al. |
| 2020/0276174 A1 | 9/2020 | Bearss et al. |
| 2020/0276215 A1 | 9/2020 | Bearss et al. |
| 2020/0281949 A1 | 9/2020 | Warner et al. |
| 2020/0316084 A1 | 10/2020 | Bearss et al. |
| 2021/0052568 A1 | 2/2021 | Warner et al. |
| 2021/0228582 A1 | 7/2021 | Bearss et al. |
| 2021/0261585 A1 | 8/2021 | Siddiqui-Jain et al. |
| 2021/0277037 A1 | 9/2021 | Siddiqui-Jain |
| 2021/0332071 A1 | 10/2021 | Siddiqui-Jain et al. |
| 2021/0379402 A1 | 12/2021 | Smith et al. |

(56) References Cited

U.S. PATENT DOCUMENTS

| | | |
|---|---|---|
| 2022/0257581 A1 | 8/2022 | Bearss et al. |
| 2022/0305037 A1 | 9/2022 | Bearss et al. |
| 2022/0339172 A1 | 10/2022 | Warner et al. |

FOREIGN PATENT DOCUMENTS

| | | |
|---|---|---|
| EP | 0137193 A2 | 4/1985 |
| EP | 0241003 A2 | 10/1987 |
| EP | 0253738 A1 | 1/1988 |
| EP | 0253739 A1 | 1/1988 |
| EP | 0321918 A2 | 6/1989 |
| EP | 0474129 A2 | 3/1992 |
| EP | 0507278 A2 | 10/1992 |
| EP | 0606046 A1 | 7/1994 |
| EP | 0366061 B1 | 1/1996 |
| EP | 0780386 A1 | 6/1997 |
| EP | 0818442 A2 | 1/1998 |
| EP | 0931788 A2 | 7/1999 |
| EP | 1004578 A2 | 5/2000 |
| EP | 979824 | 10/2004 |
| FR | 2338043 A1 | 8/1977 |
| GB | 9912961.1 | 6/1999 |
| IN | CHENP-2007-03645 | 11/2007 |
| JP | 2004529125 A | 9/2004 |
| JP | 2007-291111 A | 11/2007 |
| JP | 2008-513494 A | 5/2008 |
| JP | 2011-511803 A | 4/2011 |
| JP | 2013-533213 A | 8/2013 |
| RU | 2438664 C2 | 1/2012 |
| RU | 2474582 C2 | 2/2013 |
| RU | 2552642 C2 | 6/2015 |
| WO | 1990/05719 A1 | 5/1990 |
| WO | 1991/00360 A1 | 1/1991 |
| WO | 1992/009589 A1 | 6/1992 |
| WO | 1992/20373 A1 | 11/1992 |
| WO | 1993/08829 A1 | 5/1993 |
| WO | 1994/02602 A1 | 2/1994 |
| WO | 1994/11026 A2 | 5/1994 |
| WO | 1995/19970 A1 | 7/1995 |
| WO | 1995/21613 A1 | 8/1995 |
| WO | 1996/15263 A1 | 5/1996 |
| WO | 1996/27011 A1 | 9/1996 |
| WO | 1996/27583 A1 | 9/1996 |
| WO | 1996/33172 A1 | 10/1996 |
| WO | 1996/33735 A1 | 10/1996 |
| WO | 1996/34096 A1 | 10/1996 |
| WO | 1997/05265 A1 | 2/1997 |
| WO | 1997/13760 A1 | 4/1997 |
| WO | 1997/16447 A1 | 5/1997 |
| WO | 1997/22596 A1 | 6/1997 |
| WO | 1997/30174 A1 | 8/1997 |
| WO | 1997/32856 A1 | 9/1997 |
| WO | 1997/42949 A1 | 11/1997 |
| WO | 1998/02434 A1 | 1/1998 |
| WO | 1998/02437 A1 | 1/1998 |
| WO | 1998/02438 A1 | 1/1998 |
| WO | 1998/03516 A1 | 1/1998 |
| WO | 1998/07697 A1 | 2/1998 |
| WO | 1998/13344 A1 | 4/1998 |
| WO | 1998/14451 A1 | 4/1998 |
| WO | 1998/30566 A1 | 7/1998 |
| WO | 1998/33768 A1 | 8/1998 |
| WO | 1998/33798 A2 | 8/1998 |
| WO | 1998/34915 A1 | 8/1998 |
| WO | 1998/34918 A1 | 8/1998 |
| WO | 1998/50356 A1 | 11/1998 |
| WO | 1998/54093 A1 | 12/1998 |
| WO | 1999/07675 A1 | 2/1999 |
| WO | 1999/10349 A1 | 3/1999 |
| WO | 1999/16755 A1 | 4/1999 |
| WO | 1999/16787 A1 | 4/1999 |
| WO | 1999/24440 A1 | 5/1999 |
| WO | 1999/29667 A1 | 6/1999 |
| WO | 1999/35132 A1 | 7/1999 |
| WO | 1999/35146 A1 | 7/1999 |
| WO | 1999/52889 A1 | 10/1999 |
| WO | 1999/52910 A1 | 10/1999 |
| WO | 1999/53049 A1 | 10/1999 |
| WO | 1999/61422 A1 | 12/1999 |
| WO | 1999/62890 A1 | 12/1999 |
| WO | 2000/06134 A2 | 2/2000 |
| WO | 2000/12071 A2 | 3/2000 |
| WO | 2000/44362 A2 | 8/2000 |
| WO | 2000/59526 A1 | 10/2000 |
| WO | 2001/012661 A2 | 2/2001 |
| WO | 2001/60814 A2 | 8/2001 |
| WO | 2002/20568 A2 | 3/2003 |
| WO | 2003/028001 A2 | 4/2003 |
| WO | 2003/040168 A2 | 5/2003 |
| WO | 2004/022580 A2 | 3/2004 |
| WO | 2004/058804 A1 | 7/2004 |
| WO | 2005/017107 A2 | 2/2005 |
| WO | 2005/044839 A2 | 5/2005 |
| WO | 2006/099667 A1 | 9/2006 |
| WO | 2006/101846 A1 | 9/2006 |
| WO | 2006/121168 A1 | 11/2006 |
| WO | 2007/123791 A2 | 11/2007 |
| WO | 2008/021484 A1 | 2/2008 |
| WO | 2008/106635 A1 | 9/2008 |
| WO | 2008/132601 A1 | 11/2008 |
| WO | 2009-507820 A | 2/2009 |
| WO | 2009/044273 A2 | 4/2009 |
| WO | 2010/019570 A2 | 2/2010 |
| WO | 2010/027827 A2 | 3/2010 |
| WO | 2010/030727 A1 | 3/2010 |
| WO | 2010/093742 A1 | 8/2010 |
| WO | 2010/147961 A1 | 12/2010 |
| WO | 2011/054553 A1 | 5/2011 |
| WO | 2011/066342 A1 | 6/2011 |
| WO | 2011/088137 A2 | 7/2011 |
| WO | 2011/143660 A2 | 11/2011 |
| WO | 2011/153374 A1 | 12/2011 |
| WO | 2012/075383 A2 | 6/2012 |
| WO | 2012/122370 A2 | 9/2012 |
| WO | 2012/145493 A1 | 10/2012 |
| WO | 2013/079174 A1 | 6/2013 |
| WO | 2013/082660 A1 | 6/2013 |
| WO | 2013/138702 A2 | 9/2013 |
| WO | 2013/170176 A3 | 11/2013 |
| WO | 2013/182519 A1 | 12/2013 |
| WO | 2013/188355 A1 | 12/2013 |
| WO | 2013/188978 A1 | 12/2013 |
| WO | 2014/022758 A1 | 2/2014 |
| WO | 2014/047342 A1 | 3/2014 |
| WO | 2014/055897 A2 | 4/2014 |
| WO | 2014/059028 A1 | 4/2014 |
| WO | 2014/066848 A1 | 5/2014 |
| WO | 2014/100079 A1 | 6/2014 |
| WO | 2014/140180 A1 | 9/2014 |
| WO | 2014/179664 A2 | 11/2014 |
| WO | 2014/194302 A2 | 12/2014 |
| WO | 2014/209804 A1 | 12/2014 |
| WO | 2015/010094 A1 | 1/2015 |
| WO | 2015/017788 A1 | 2/2015 |
| WO | 2015/042249 A1 | 3/2015 |
| WO | 2015/047510 A1 | 4/2015 |
| WO | 2015/061668 A1 | 4/2015 |
| WO | 2015/066305 A1 | 5/2015 |
| WO | 2015/070020 A2 | 5/2015 |
| WO | 2015/081158 A1 | 6/2015 |
| WO | 2015/085847 A1 | 6/2015 |
| WO | 2015/109124 A2 | 7/2015 |
| WO | 2015/112800 A1 | 7/2015 |
| WO | 2015/112805 A1 | 7/2015 |
| WO | 2015/116539 A1 | 8/2015 |
| WO | 2015/130585 A1 | 9/2015 |
| WO | 2015/161247 A1 | 10/2015 |
| WO | 2015/181342 A1 | 12/2015 |
| WO | 2015/195163 A1 | 12/2015 |
| WO | 2015/200119 A1 | 12/2015 |
| WO | 2016/000619 A1 | 1/2016 |
| WO | 2016/028672 A1 | 2/2016 |
| WO | 2016/061144 A1 | 4/2016 |
| WO | 2016/071448 A1 | 5/2016 |

(56) References Cited

FOREIGN PATENT DOCUMENTS

| | | |
|---|---|---|
| WO | 2016/073913 A1 | 5/2016 |
| WO | 2016/092419 A1 | 6/2016 |
| WO | 2016/111947 A2 | 7/2016 |
| WO | 2016/115105 A1 | 7/2016 |
| WO | 2016/144803 A2 | 9/2016 |
| WO | 2016/149613 A2 | 9/2016 |
| WO | 2016/154380 A1 | 9/2016 |
| WO | 2016/161270 A1 | 10/2016 |
| WO | 2016/172214 A1 | 10/2016 |
| WO | 2016/176288 A1 | 11/2016 |
| WO | 2016/176299 A1 | 11/2016 |
| WO | 2016/187316 A1 | 11/2016 |
| WO | 2017/024073 | 2/2017 |
| WO | 2017/075349 A1 | 5/2017 |
| WO | 2018/013918 A2 | 1/2018 |
| WO | 2018/094275 A1 | 5/2018 |
| WO | 2018/119000 | 6/2018 |
| WO | 2019/055579 A1 | 3/2019 |
| WO | 2019/200243 A1 | 10/2019 |
| WO | 2019/246421 A1 | 12/2019 |
| WO | 2020/077300 A1 | 4/2020 |
| WO | 2020/092615 A1 | 5/2020 |
| WO | 2020/117988 A1 | 6/2020 |
| WO | 2020/118252 A1 | 6/2020 |
| WO | 2020/191326 A1 | 9/2020 |
| WO | 2021/007316 A1 | 1/2021 |
| WO | 2021/007314 A2 | 2/2021 |

OTHER PUBLICATIONS

Bogenberger, James, et al. "Combined venetoclax and alvocidib in acute myeloid leukemia." Oncotarget 8.63 (2017): 107206.*

Adams, et al., "The Bcl-2 Protein Family: Arbiters of Cell Survival," Science, 281:1322-1326 (1998).

Adlard, et al., "Prediction of the Response of Colorectal Cancer to Systemic Therapy," Lancet Oncol, 3:75-82 (2002).

Aït-Ikhlef, et al., "The Motoneuron Degeneration in the Wobbler Mouse is Independent of the Overexpression of a Bcl2 Transgene in Neurons," Neuoscience Letters, 199:163-166 (1995).

Akgul, C., "Mcl-1 is a Potential Therapeutic Target in Multiple Types of Cancer", Cell. Mol. Life Sci., 66:1326-1336 (2009).

Almarzooqi, et al., "Comparison of Peripheral Blood Versus Bone Marrow Blasts Immuniphenotype in Pediatric Acute Leukemias," Ibnosina Journal of Medicine and Biomedical Sciences, 3(6):195-204 (2011).

Al-Mawali, "Leukemic Stem Cells Shows the Way for Novel Target of Acute Myeloid Leukemia Therapy", J Stem Cell Res Ther, 3(4):1-8 (2013).

Altschul, et al., "Gapped BLAST and PSI-BLAST: a New Generation of Protein Database Search Programs," Nucleic Acids Research, 25(17):3389-3402 (1997).

Alvocidib, definition of alvocidib, NCI Dictionary of Cancer Terms—National Cancer Institute, retrieved from URL: https://www.cancer.gov/publications/dictionaries/cancer-terms/def/alvocidib on Jan. 7, 2021, 1 page.

"Alvocidib Biomarker-driven Phase 2 AML Study," Sumitomo Dainippon Pharma Oncology, ClinicalTrials.gov identifier: NTC02520011, URL:https://www.clinicaltrials.gov/ct2/show/NCT02520011, Accessed: Dec. 31, 2020, 8 pages.

Araki et al., "Allogeneic Hematopoietic Cell Transplantation for Acute Myeloid Leukemia: Time to Move Toward a Minimal Residual Disease-Based Definition of Complete Remission?" J Clin Oncol 34(4):329-336, 2016.

Arguello F., et al., "Flavopiridol induces apoptosis of normal lymphoid cells, causes immunosuppression, and has potent antitumor activity in vivo against human leukemia and lymphoma xenografts", Blood, 91:2482-2490 (1998).

Attal, M., et al., "Lenalidomide Maintenance after Stem-Cell Transplantation for Multiple Myeloma," The New England Journal of Medicine, 366:1782-1791 (2012).

Awan, F. T., et al., "A Phase I Clinical Trial of Flavopiridol Consolidation in Chronic Lymphocytic Leukemia Patients Following Chemoimmunotherapy", Ann Hematol, 95:1137-1143 (2016).

Bae, et al., "Underphosphorylated BAD Interacts with Diverse Antiapoptotic Bcl-2 Family Proteins to Regulate Apoptosis," Apoptosis, 6:319-330 (2001).

Barrentina, et al., "The Cancer Cell Line Encyclopedia Enables Predictive Modelling of Anticancer Drug Sensitivity," Nature, 483:603-607 with Addenedum in Nature 492:290 (2012).

Bearss, "NOXA Priming-Predictive Biomarker for Patients with Acute Myeloid Leukemia to Improve Treatment Outcomes," Harvard Business School Challenge—Open Forum—Precision Trials Challenge, Mar. 11, 2016; URL: https://openforum.hbs.org/challenge/precision-medicine/submit-ideas/noxa-priming . . . downloaded on Dec. 8, 2016; 7 pages.

Bearss, "Targeting MCL1 Dependent Cancers by CDK9 Inhibition", Abstract for Keynote Address, 9th International Conference on Leukemia and Hematologic Oncology, Oct. 5-6, 2017 London, UK, J Hematol Thrombo Dis, 5(5Suppl), 2017 (1 page).

Beauchamp, et al., "Amino Acid Ester Prodrugs of Acyclovir", Antiviral Chemistry and Chemotherapy, 3(3):157-164 (1992).

Belikov, V.G., in *Pharameceutical Chemistry*, vol. 1, Moscow, High School, pp. 43-47 (1993) with English translation.

Belmar, J. and Fesik, S.W., "Small Molecule Mcl-1 Inhibitors for the Treatment of Cancer", Pharmacol Ther., 145:76-84 (2015).

Benyon, B., "FDA Grants Venclexta an Accelerated Approval for AML Treatment", Nov. 21, 2018, 2 pages, URL: https://www.curetoday.com/articles/fda-grants-venclexta-an-accelerated-approval-for-aml-treatment.

Berge, et al., "Pharmaceutical Salts", Journal of Pharmaceutical Sciences 66(1):1-19 (1997).

Besbes, S. and Billard, C., "First MCL-1-Selective BH3 Mimetics as Potential Therapeutics for Targeted Treatment of Cancer", Cell Death and Disease, 6:2 pages (2015).

Bible, K.C., et al., "Cytoxic Synergy Between Flavopiridol (NSC 649890, 186-8275) and Various Antineoplastic Agents: The Importance of Sequence of Adminstration", American Association for Cancer Research, Baltimore MD, US, 57:3375-3380 (1997).

Billard, C., "BH3 Mimetics: Status of the Field and New Developments", Mol Cancer Ther, 12(9):1671-1700 (2013).

Blachly, et al., "Emerging Drug Profile: Cyclin-Dependent Kinase Inhibitors," Leuk Lymphoma, 54:2133-2143 (2013).

Blum, W., et al., "Phase I Clinical and Pharmakokinetic Study of a Novel Schedule of Flavopiridol in Relapsed and Refractory Acute Leukemias", Haematologica, 95(7):1098-1105 (2010).

Bodet, et al., "BH3-Only Protein Bik is Involved in Both Apoptosis Induction and Sensitivity to Oxidative Stress in Multiple Myeloma," British Journal of Cancer, 103:1808-1814 (2010).

Boffo et al., "CDK9 Inhibitors in Acute Myeloid Leukemia," Journal of Experimental & Clinical Cancer Research, 37(36):1-10, 2018.

Bogenberger, et al., "BCL-2 Family Proteins as 5-Azacytidine-Sensitizing Targets and Determinants of Response in Myeloid Malignancies", Leukemia, 28:1657-1665 (2014).

Bogenberger, J., et al., "Combined Venetoclax and Alvocidib in Acute Myeloid Leukemia", Oncotarget, 8(63):107206-107222 (2017).

Bose, et al., "Mcl-1 as a Therapeutic Target in Acute Myelogenous Leukemia (AML)," Leukemia Research Reports, 2:12-14 (2013).

Bouillet, et al., "Proapoptotic Bcl-2 Relative Bim Required for Certain Aopotoic Responses, Leukocyte Homeostasis, and to Preclude Autoimmunity," Science, 286:1735-1738 (1999).

Boyd, et al., "Bik, a Novel Death-Inducing Protein Shares a Distinct Sequence Motif with Bcl-2 Family Proteins and Interacts with Viral and Cellular Survival-Promoting Proteins," Oncogene, 11:1921-1928 (1995).

Bradbury, et al., "Optimisation of a Series of Bivalent Triazolopyridazine Base Bromodomain and Exterminal Inhibitos: The Discovery of (3R)-4-[2-[4-[1-(3-methoxy-[1,2,4]triazolo[4,3-b]pyridazin-6-yl)-4-piperidyl]phenoxy]ethyl]-1,3-dimethyl-piperzin-2-one (AZD5153)", Journal of Medicinal Chemistry, 59(17):7801-7817 (2016).

Brady, et al., "Reflections on a Peptide," Nature, 368:692-693 (1994).

(56) References Cited

OTHER PUBLICATIONS

Braun, et al., "Preclinical Study of the Bromodomain Inhibitor OTX015 in Actue Myeloid (AML) and Lymphoid (ALL) Leukemias," Blood, 122:4218 (44 pages) Abstract Only 2013.
Brennan, et al., "Preparation of Bispecific Antibodies by Chemical Recombination of Monoclonal Immunoglobulin $G_1$ Fragments," Science, 229:81-83 (1985).
Brooks E. E., et al., "CVT-313, a specific and potent inhibitor of CDK2 that prevents neointimal formation", J. Biol. Chem., 272:299207-29911 (1997).
Brunelle, et al., "MCL-1-Dependent Leukemia Cells are More Sensitive to Chemotherapy than BCL-2-Dependent Counterparts," J. Cell. Biol., 187(3):429-442 (2009).
Brunetto, et al., "FIrst-In-Human, Pharmacokinetic and Pharmacodynamic Phase I Study of Resminostat, an Oral Histone Deacetylase Inhibitor, in Patients with Advanced Solid Tumors," Clin Cancer Res., 19(19):5494-5504 (2013).
Brüsselbach, et al., "Cell Cycle-Independent Induction of Apoptosis by the Anti-Tumor Drug Flavopiridol in Endothelial Cells", Int. J. Cancer, 77:146-152 (1998).
Buccisano, et al., "Prognostic and Therapeutic Implications of Minimal Residual Disease Detection in Acute Myeloid Leukemia", Blood, 119(2):332-341 (2012).
Buggy, et al., "CRA-024781: A Novel Synthetic Inhibitor of Histone Deacetylase Enzymes with Antitumor Activity In Vitro and In Vivo," Mol Cancer Ther, 5(5):1309-1317 (2006).
Buijs, A., et al., "A novel CBFA2 single-nucleotide Mutation in Familial Platelet Disorder with Propensity to Develop Myeloid Malignancies", Blood, 89(9):2856-2868 (2001).
Bundgard, H., in *Design of Prodrugs*, Bungard, H. ed., (NY:Elsevier), pp. 7-9 and 21-24, 1985.
Buron, et al., "Use of Human Cancer Cell Lines Mitochondria to Explore the Mechanisms of BH3 Peptides and ABT-737-Induced Mitochondrial Membrane Permeabilization," PLoS One, 5(3):e9924, 13 pages (2010).
Burrer et al., "Selective Peptide Inhibitors of Antiapoptotic Cellular and Viral Bcl-2 Proteins Lead to Cytochrome C Release During Latent Kaposi's Sarcoma-Associated Herpesvirus Infection," Virus Res. 211:86-88, 2016. (Author's manuscript).
Byrd, et al., "Flavopirdol Induces Apoptosis in Chronic Lymphocytic Leukemia Cells via Activation of Caspase-3 Without Evidence of bcl-2 Modulation or Dependence on Functional p53," Blood, 92(10):3804-3816 (1998).
Byrd, et al., "Chronic Lymphocytic Leukemia," American Society of Hematology Education Program Book, pp. 163-183 (2004).
Byrd, et al., "Flavopirdol Administered as a Pharmacologically-Derived Schedule Demonstrates Marked Clinical Actvity in Refractory, Genetically High-Risk Chronic Lymphocytic Leukemia (CLL)," Blood 104, Abstract No. 341, 2 pages (2004).
Byrd, et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," Blood, 104, Abstract No. 3485 2 pages, (2004).
Byrd, et al., "Treatment of Relapsed Chronic Lymphocytic Leukemia by 72-Hour Continuous Infusion or 1-Hour Bolus Infusion of Flavorpiridol: Results from Cancer and Leukemia Group B Study 19805," Clinical Cancer Research 11(11):4176-4181 (2005).
Byrd, et al., "Flavopirdol Administered Using a Pharmacologically Derived Schedule is Associated with Marked Clinical Efficacy in Refractory, Genetically High-Risk Chronic Lymphocytic Leukemia," Blood 109(2):399-404 (2007).
Byrd, J.C., et al., "Pretreatment Cytogenetic Abnormalities are Predictive of Induction Success, Cumulative Incidence of Relapse, and Overall Survival in Adult Patients with de novo Acute Myeloid Leukemia: Results from Cancer and Leukemia Group B (CALGB8461)", Blood, 100:4325-4336 (2002).
Calin, et al., "A Micro RNA Signature Associated with Prognosis and Progression in Chronic Lymphocytic Leukemia," The NEJM, 353:1793-1801 (2005).
Cannon, J.G., "Analog Design" in Burger's Medicinal Chemistry and Drug Discovery, Fith Edition, Manfred E. Wolf ed. (NY:Wiley Interscience), Chapter 19 pp. 783-802 (1995).
Carlson, et al., "Flavopiridol Induces $G_1$ Arrest with Inhibition of Cyclin-Dependent Kinase (CDK) 2 and CDK4 in Human Breast Carcinoma Cells," Cancer Research, 56:2973-2978 (1996).
Caron, et al., "Engineered Humanized Dimeric Forms of IgG are More Effective Antibodies," J Exp Med, 176:1191-1195 (1992).
Cartron, et al., "The First α Helix of Bax Plays a Necessary Role in its Ligand-Induced Activation by the BH3-Only Proteins Bid and PUMA,"Mol. Cell, 16:807-818 (2004).
CAS Registry No. 146426-40-6—Flavopiridol (1993).
CAS Registry No. 951209-71-5, "IRX 2" Entered STN Oct. 23, 2007, 1 page.
Certo, et al., "Mitochondria Primed by Death Signals Determine Cellular Addiction to Antiapoptotic BCL-2 Family Members," Cancer Cell, 9:351-356 (2006).
Chan, D., et al., "Belinostat and Panobinostat (HDACI): in vitro and invivo sStudies in Thyroid Cancer", J. Cancer Res.Clin. Oncol., 139:1507-1514 (2013).
Chang M. W., et al., "Adenovirus-mediated over-expression of the cyclin/cyclin-dependent kinase inhibitor, p21 inhibits vascular smooth muscle cell proliferation and neointima formation in the rat carotid artery model of balloon angioplasty", J. Clin. Invest., 96:2260-2268 (1995).
Chao, et al., "Flavopiridol Inactivates P-TEFb and Blocks Most RNA II Transcription In Vivo," The Jornal of Biological Chemistry, 276(34):31793-31799 (2001).
Chao, et al., "Flavopiridol Inhibits P-TEFb and Blocks HIV-1 Replication," The Jornal of Biological Chemistry, 275(37):28345-28348 (2000).
Chen D., "Downregulation of cyclin-dependent kinase 2 activity and cyclin A promoter activity in vascular smooth muscle cells by p27(KIP1), an inhibitor of neointima formation in the rat carotid artery", J. Clin. Invest., 99:2334-2341 (1997).
Chen, et al., "Capase Cleavage of $Bim_{EL}$ Triggers a Positive Feedback Amplification of Apoptotic Signaling," PNAS, 101(5):1235-1240 (2004).
Chen, et al., "Differential Targeting of Prosurvival Bcl-2 Proteins by their BH3-Only Ligands Allows Complementary Apoptotic Function," Molecular Cell, 17:393-403 (2005).
Chen, et al., "Transcriptional Inhibition by Flavopiridol: Mechanism of Chronic Lymphocytic Leukemia Cell Death," Blood, 106:2513-2519 (2005).
Chen, et al., "Mcl-1 Down-Regulation Potentiates ABT-737 Lethality by Cooperatively Inducing Bak Activation and Bax Translocation," Cancer Res, 67(2):782-791 (2007).
Chen, et al., "Mechanism of Action of SNS-032, a Novel Cyclin-Dependent Kinase Inhibitor in Chronic Lymphocytic Leukemia," Blood, 113:4637-464645 (2009).
Chen, et al., "Androgen Receptor Serine 81 Phosphorylation Mediates Chromatin Binding and Transcriptional Activation", Journal of Biological Chemistry, 287(11):8571-8583 (2012).
Chen, C., et al., "Lenalidomide in Multiple Myeloma—a Practice Guideline", Curr Oncol, 20(2):e136-e149 (2013).
Cheng, et al., "Bax-Independent Inhibition of Apoptosis by $Bcl-x_L$," Nature, 379:554-556 (1996).
Cheng, et al., "BCL-2, $BCL-X_L$ Sequester BH3 Domain-Only Molecules Preventing BAX- and BAK-Mediated Mitochondrial Aopotosis," Mol. Cell, 8:705-711 (2001).
Cheronis, "Semimicro Experimental Organic Chemistry," deGratt, pp. 67-69 (1958).
Cheson, et al., "National Cancer Institute Sponsored Working Group Guidelines for Chronic Lymphocytic Leukemia: Revised Guidelines for Diagnosis and Treatment," Blood, 87(12):4990-4997 (1996).
Chipuk, et al., "Direct Activation of Bax by p53 Mediates Mitochondrial Membrane Permeabilization and Apoptosis," Science, 303:1010-1014 (2014).
Chittenden, et al., "A Conserved Domain in Bak, Distinct from BH1 and BH2, Mediates Cell Death and Protein Binding Functions," The EMBO Journal, 14(22):5589-5596 (1995).

(56) References Cited

OTHER PUBLICATIONS

Chittenden, et al., "Induction of Apoptosis by the Bcl-2 Homologue Bak," Nature, 374:733-736 (1995).
Chonghaile, et al., "Mimicking the BH3 Domain to Kill Cancer Cells," Oncogene, 27:S149-S157 (2009).
Chonghaile, et al., "Mitochondrial Apoptotic Priming Measured by BH3 Profiling Regulates Clinical Response to Chemotherapy in Myeloma and Acute Lymphoblastic Leukemia and Explains Therapeutic Index," Blood, 118:1142—6 pages (2011)—Abstract Only.
Chonghaile, et al., "Pretreatment Mitochondrial Priming Correlates with Clinical Response to Cytotoxic Chemotherapy," Science, 334:1129-1133 (2011).
Chou, T.-C. and Talalay, P., "Quantitative Analysis of Dose-Effect Relationships: The Combined Effects of Multiple Drugs or Enzyme Inhibitors", Advances in Enzyme Regulation, 22:27-55 (1984).
Choudhary, et al., "MCL-1 and BCL-xL-Dependent Resistance to the BCL-2 Inhibitor ABT-199 can be Overcome by Preventing PI3K/AKT/mTOR Activation in Lymphoid Malignancies," Cell Death and Disease, 6:e1593—12 pages (2015).
Christian, B. A., et al., "Flavopiridol in Chronic Lymphocytic Leukemia: A Concise Review," Clinical Lymphoma & Myeloma, 9(Suppl 3):S179-S185 (2009).
Clinical Study, No Authors Available, "Alvocidib, Followed by Cytarabine + Mitoxantrone, Makes Impact in AML", Inpharma Weekly, 1606:8 (2007).
Clowes A W, et al., "Significance of quiescent smooth muscle migration in the injured rat carotid artery", Circ. Res., 56:139-145 (1995).
Cole, et al., "The EBV-Hybridoma Technique and its Application to Human Lung Cancer," in Monoclonal Antibodies and Cancer Therapy, Reisfel et al., eds., (NY:Alan R. Liss, Inc.), pp. 77-96 (1985).
Common Terminology Criteria for Adverse Events (CTCAE) Version 5.0 Publichsed: Nov. 7, 2017 U.S. Department of Health and Human Services, National Institutes of Health, National Cancer Institute, URL=https://ctep.cancer.gov/protocoldevelopment/electronic_applications/docs/CTCAE_v5_Quick Reference Accessed: Dec. 31, 2020, 147 pages.
Conaway, et al., "Mediator Complex and Transcription Elongation," Biochim Biophys Acta, 1829(1):69-75 (2013).
Corbett, et al., "Evaluation of Single Agents and Combinations of Chemotherapeutic Agents in Mouse Colon Carcinomas", Cancer 40:2660-2680 (1987).
Corbett, et al., "Response to Transplantable Tumors of Mice to Antracenedione Derivatives Alone and in Combination with Clinically Useful Agents", Cancer Treatment Reports 66:1187-1200 (1982).
Cory, et al., "The BCL-2 Family: Regulators of the Cellular Life-Or-Death Switch," Nature Reviews Cancer, 2:647-656 (2002).
Cosulich, et al., "Regulation of Apoptosis by BH3 Domains in a Cell-Free System," Current Biology, 7:913-920 (1997).
Cote, et al., "Generation of Human Monoclonal Antibodies Reactive with Cellular Antigens," Proc. Natl. Acad. Sci., 80:2026-2030 (1983).
Czabotar, et al., "Bax Activation by Bim?," Cell Death and Differentiation, 16:1187-1191 (2009).
Czabotar, et al., "Structural Insights into the Degradation of Mcl-1 Induced by BH3 Domains," PNAS, 104(15):6217-6222 (2007).
Czech, et al., "Antitumoral Activity of Flavone L 86-8275," International Journal of Oncology, 6:31-36 (1995).
Daigle, et al., "Potent Inhibition of DOT1L as Treatment of MLL-Fusion Leukemia," Blood, 122(6):1017-1025 (2013).
Dang, "MYC on the Path to Cancer," Cell 149(1):22-35, 2012. (28 pages).
Danial, et al, "Cell Death: Critical Control Points," Cell, 116:205-219 (2004).
Davids, et al., "Targeting the B-Cell Lymphoma/Leukemia 2 Family in Cancer," Journal of Clinical Oncology, 30(25):3127-3135 (2012).
Davids, et al., "BH3 Profiling Demonstrates that Resotration of Apoptotic Priming Contributes to Increased Sensitivity to PI3K Inhibition in Stroma-Exposed Chronic Lymphocytic Leukemia Cells," Blood, 118:974—6 pages (2011).
Dawson, M.A., et al., "Inhibition of BET Recruitment to Chromatin as an Effective Treatment for MLL-Fusion Leukaemia", Nature, 478:328-333 (2011).
De Azevedo, Jr., et al., "Structural Basis for Inhibition of Cyclin-Dependent Kinase 9 by Flavopiridol," Biochemical and Biophysical Research Communications, 293:566-571 (2002).
De Azevedo, Jr., et al., "Structural Basis for Specificity and Potency of a Flavanoid Inhibitor of Human CDK2, a Cell Cycle Kinase", Proc. Natl. Acad. Sci., 93:2725-2740 (1996).
De Haas et al., "Initial Diagnostic Work-Up of Acute Leukemia: ASCO Clinical Practice Guideline Endorsement of the College of American Pathologists and American Society of Hematology Guideline," J Clin Oncol 37(3):239-253, 2018.
De Young M. B, and Dichek D. A., "Gene therapy for restenosis", Circ. Res., 82:306-313 (1998).
Debrincat, et al., "BCL-2 is dispensable for hrombopoiesis and Platelet Survival", Cell Death & Disease, 6:e1721, 8 pages (2015).
Degrado, "Design of Peptides and Proteins," Advances in Protein Chemistry, 39:51-124 (1988).
Dehm, et al., "Alternatively Spliced Androgen Receptor Variants", Endocrine-Related Cancer, 18(5):R183-R196(2011).
Deng, et al, "BH3 Profiling Identifies Three Distinct Classes of Apoptotic Blocks to Predict Response to ABT-737 and Conventional Chemotherapeutic Agents," Cancer Cell, 12:171-185 (2007).
Derenne, et al, "Antisense Strategy Shows that Mcl-1 Rather than Bcl-2 or Bcl-$_{XL}$ is an Essential Survival Protein in Human Myeloma Cells," Blood, 100:194-199 (2002).
Desagher, et al., "Bid-Induced Conformational Change of Bax is Responsible for Mitochondrial Cytochrome c Release During Apoptosis," The Journal of Cell Biology, 144(5):891-901 (1999).
Dettman, et al., "Mitochondrial Profiling in AML Patients Treated with an Alvocidib Containing Regimen Reveals MCL1 Dependency in Responder Bone Marrow," Cancer Research, 75: Abstract No. 3400, 2 pages (2015).
Di Lisa, et al., "Mitochondrial Function and Cell Injury in Single Cardiac Myocytes Exposed to Anoxia and Reoxygenation," Transplantation Proceedings, 27(5):2829-2830 (1995).
Di Lisa, et al., "Mitochondrial Membrane Potential in Single Living Adult Rat Cardiac Myocytes Exposed to Anoxia or Metabolic Inhibition," Journal of Physiology, 486:1-13 (1995).
Diamandis, et al., *Immunoassay*, Academic Press, Inc., New York 1996.
Dillman, R.O., et al., "A Comparative Study of Two Different Doses of Cytarabine for Acute Myeloid Leukemia: A Phase III Trial of Cancer and Leukemia Group B", Blood, 78(10):2520-2526 (1991).
Dimopoulos et al., "Multiple Myeloma: EAH-ESMO Clinical Practice Guidelines for Diagnosis, Treatment and Follow-Up," Annals of Oncology 32(3):309-322, 2021.
DiNardo, C.D., et al., "Venetoclax Combined with Decitabine or Azacitidine in Treatment-Naïve, Elderly Pations With Acute Myeloid Leukemia", Blood, 133:7-17 (2019).
DiNardo, C.D. and Cortes, J.E., "New Treatment for Acute Myelogenous Leukemai," Expert Opin. Pharmacother, 16(1):95-106 (2015).
Dinnen, et al, "Redirecting Apoptosis to Aponecrosis Induces Selective Cytotoxicity to Pancreatic Cancer Cells Through Increased ROS, Decline in ATP Levels and VDAC," Mol Cancer Ther, 12(12):2972-2803 (2013).
Dittmann, et al., "The Commonly Used P13-Kinase Probe LY294002 is an Inhibitor of BET Bromodomains", ACS Chem. Biol., 9(2):495-502 (2014).
Döhner, et al., "Genomic Abberations and Survival in Chronic Lymphocytic Leukemia," NEJM, 343:1910-1916 (2000).
Döhner, H., et al., "Acute Myeloid Leukemia", The New England Journal of Medicine, 373(12), 1136-1152 (2015).
Döhner et al., "Diagnosis and Management of AML in Adults: 2017 ELN Recommendations From an International Expert Panel," Blood 129(4):424-447, 2017.
Drees M., eta l., "Flavopiridol (L86-8275): Selective antitumor activity in vitro and activity in vivo for prostate carcinoma cells", Clin. Cancer Res., 3:273-279 (1997).

(56) References Cited

OTHER PUBLICATIONS

Egle, et al., "Bim is a Suppressor of Myc-induced Mouse B Cell Leukemia," PNAS, 101(16):6164-6169 (2004).
Eichhorst et al., "Chronic Lymphocytic Leukaemia: ESMO Clinical Practice Guidelines for diagnosis, treatment and follow up," Annals of Oncology 32(1):23-33, 2020.
Ellerby, et al., "Anti-Cancer Activity of Targeted Pro-Apoptotic Peptides," Nature Meicine, 5(9):1032-1038 (1999).
Elliot, et al, "Intracellular Trafficking and Protein Delivery by a Herpesvirus Structural Protein," Cell, 88:223-233 (1997).
Elston, et al., "Pathological Prognostic Factors in Breast Cancer. I. The Value of Histological Grade in Breast Cancer: Experience from a Large Study with Long-Term Follow-Up," Hisopathology, 19:403-410 (1991).
Ember, et al., "Acetyl-lysine Binding Site of Bromodomain-Containing Protein 4 (BRD4) Interacts with Diverse Kinase Inhibitors," ACS Chem Biol, 9:1160-1171 (2014).
Eskes, et al., "Bid Induces the Oligomerization and Insertion of Bax into the Outer Mitochondrial Membrane," Mol and Cell biol, 20(3):929-935 (2000).
Evans, "Clathrate Compounds" in *An Introduction to Crystal Chemistry*, (London:Cambridge University Press), pp. 393-397 (1964).
Falkenberg, et al., "Histone Deacetylases and their Inhibitors in Cancer, Neuological Diseases and Immune Disorder, " Nature Reviews Drug Discovery, 13: 673-691 (2014)—addendum included.
Fanidi, et al., "Cooperative Interaction Between c-myc and bcl-2 Proto-Oncogenes," Nature, 359:554-556 (1992).
Fenaux et al., "Myelodysplastic syndromes: ESMO Clinical Practice Guidelines for diagnosis and follow-up," Annals of Oncology 25(Supplement 3):iii57-iii69, 2014.
Fernandez, et al., "Anthracycline Dose Intesification in Acute Myeloid Leukemia", New England Journal of Medicine, 361(13):1249-1259 (2009).
Ferrara, et al., "Consensus-Based Definition of Unfitness to Intensive and Nonintensive Chemotherapy in Acute Myeloid Leukemia: a Project of SIE, SIES and GITMO Group on a New Tool for Therapy Decision Making", Leukemia, 27:997-999 (2013).
Férriz, J.M. and Vinšová, J., "Prodrug Design of Phenolic Drugs", Current Pharmaceutial Design, 16:2033-2052 (2010).
Filippakopoulos, et al., "Targeting Bromodomains: Epigenetic Readers of Lysine Acetylation," Nature Reviews Drug Discovery, 13:337-356 (2014).
Filippakopoulos, et al., "Selective Inhibition of BET Bromodomains," Nature, 468:1067-1073 (2010).
Fish, et al., "Identification of a Chemical Probe for Bromo and Extra C-Terminal Bromodomain Inhibition through Optimization of a Fragment-Derived Hit," J Med. Chem., 55:9831-9837 (2012).
Fiskum, et al., "[21] Apoptosis-Related Activities Measured with Isolated Mitochondria and Digitonin-Permeabilized Cells," Methods in Enzymology, 322:222-234 (2000).
Fiskus, et al., Highly Active Combiniation of BRD4 Antagonist and Histone Deacetylase Inhibitor Against Human Acute Myelogenous Leukemia Cells, Molecular Cancer Therapeutics, 13(5):1142-1154 (2014).
Flinn, et al., "Flavopiridol Administered as a 24-hour Continuous Inufsion in Chronic Lymphocytic Leukemia Lacks Clinical Activity," Leukemia Research, 29:1253-1257 (2005).
Foight, et al., "Designed BH# Peptides with High Affinity and Specificity for Targeting Mcl-1 in Cells," ACS, Chem Biol., 9:1962-1968 (2014).
Forostyan, T.V., et al., "Abstract C081: Targeting CDK9 and MCL1 in Castration-Sensitive and Resistant Prostate Cancer Models", as present at AACR-NCI-EORTC International Conference on Molecular Targets and Cancer Therapeutiics, Oct. 26-30, 2019, Boston, MA, Molecular Cancer Therapeutic, 18(12):Supplement, 4 pages (2019).
Frankel, et al., "Activity of Synthetic Peptides from the Tat Protein of Human Immunodeficiency Virus Type 1," Proc. Natl. Acad. Sci. USA, 86:7397-7401 (1989).
Freeman et al., "Measurable Residual Disease at Induction Redefines Partial Response in Acute Myeloid Leukemia and Stratifies Outcomes in Patients at Standard Risk Without NPM1 Mutations," J Clin Oncol 36(15):1486-1497, 2018. (24 pages).
Freeman et al., "Prognostic Relevance of Treatment Response Measured by Flow Cytometric Residual Disease Detection in Older Patients with Acute Myeloid Leukemia," J Clin Oncol 31(32):4123-4131, 2013.
Freidman, et al., "Precision Medicine for Cancer with Next-Generation Functional Diagnostics," Nat. Rev. Cancer, 15(12):747-756 (2015).
Fuchs, et al., "Precision for Polyarginine Entry into Mammalian Cells," Biochemsitry, 43(9):2438-2444 (2004).
Fukui, et al., "The Analysis of the Effect of JQ1 and Flavopirdol on Chondrocytes Under Inflammatory Stimuli," ORS 2014 Annual meeting, New Orleans, LA, Mar. 15-18, 2014, 4 pages.
Futaki, et al., "Arginine-Rich Peptides: An Abundant Source of Membrane-Permeable Peptides Having Potential as Carriers for Intracellular Protein Delivery," The Journal of Biological Chemistry, 276(8):5836-5840 (2001).
Gambella et al., "Minimal Residual Disease by Flow Cytometry and Allelic-Specific Oligonucleotide Real-Time Quantitative Polymerase Chain Reaction in Patients With Myeloma Receiving Lenalidomide Maintenance: A Pooled Analysis," Cancer 125:750-760, 2019.
Gao et al., "Multiple Myeloma Cancer Stem Cells," Oncotarget 7(23):35466-35477, 2016.
Geng Y. J., et al., "Apoptosis of vascular smooth muscle cells induced by in vitro stimulation with interferon-gamma, tumor necrosis factor-alpha, and interleukin-1 beta", Arterioscier. Thromb. Biol, 16:19-27 (1996).
George, B., et al., "A Phase I, First-In-Human, Open-Label, Dose-Escalation, Safety, Pharmacokinetic, and Pharmacodynamic Study of Oral TP-1287 Administered Daily to Patients with Advanced Solid Tumors", Journal of Clinical Oncology, 38(15) Abstract 3611—3 pages (2020).
George B, et al., "A Phase I, First-in-human, Open-label, Dose escalation, Safety, Pharmacokinetic, and Pharmacodynamic Study of Oral TP-1287 Administered Daily to Patients with Advanced Solid Tumors," American Society of Clinical Oncology—56th Annual Meeting. 2020, poster, 1 page.
Gerber, et al., "Association of Acute Myeloid Leukemia's Most Immature Phenotype with Risk Groups and Outcomes", Haematologica, 101(5):607-616 (2016).
Gerber, et al., A Clinically Relevant Population of Leukemic CD34+ CD38-Cells in Acute Myeloid Leukemia, Blood, 119(15):3571-3577 (2012).
Geserick, et al., "The Ratio of Mcl-1 and Noxa Determines ABT737 Resistance in Squamous Cell Carcinoma of the Skin," Cell Death and Disease, 5:e1412, 14 pages (2014).
Ghyczy, M., et al., "Electrophilic Methyl Groups Present in the Diet Ameliorate Pathological States Induced by Reductive and Oxidative Stress: A Hypothesis", Britis Journal of Nutrition, 85(4):409-414 (2001).
Giles, et al. "A Phase I Study of Intravenous LBH589, a Novel Cinnamic Hydroxamic Acid Analogue Histone Deacetylase Inhibitor, In Patients withRefractory Hematologic Malignancies," Clin Cancer Res., 12(15):4628-4635 (2006).
Glossary of medical education terms, Institute of International Medical Education, URL: http://www.iime.org/glossart.htm, accessed Mar. 2013.
Gojo, et al., "The Cyclin-Dependent Kinase Inhibitor Falovpiridol Induces Apoptosis in Multiple Myeloma Cells Through Transcriptional Respression and Down-Regulation of Mcl-1," Clinical Cancer Research, 8:3527-3538 (2002).
Goldsmith, et al., "BH3 Peptidomimetics Potentially Activate Apoptosis and Demonstrate Single Agent Efficacy in Neuroblastoma," Oncogene 25:4525-4533 (2006).
Gores, et al., "Selectively Targeting Mcl-1 for the Treatment of Acute Myelogeneous Leukemia and Solid Tumors", Genes & Development, 26:305-311 (2012).
Göttlicher, et al., "Valproic Acid Defines a Novel Class of HDAC Inhibitors Inducing Differentiation of Transformed Cells," The EMBO Journal, 20(24):6969-6978 (2001).

(56) References Cited

OTHER PUBLICATIONS

Green, et al., "A Matter of Life and Death," Cancer Cell, 1:19-30 (2002).
Green, et al., "The Pathophysiology of Mitochondrial Cell Death," Science, 305:626-629 (2004).
Green, et al., "Life, Death, BH3 Profiles, and the Salmon Mousse," Cancer Cell, 12:97-99 (2007).
Griffiths, et al., "Cell Damage-Induced Conformational Changes of the Pro-Apoptotoic Protein Bak In Vivo Precede the Onset of Apoptosis," The Journal of Cell Biology, 144(5):903-914 (1999).
Gross, et al., "Enforced Dimerization of BAX Results in its Translocation, Mitochondrial Dysfunction and Aopoptosis," The EMBO Journal, 17(14):3878-3885 (1998).
Gruber, et al., "Efficient Tumor Cell Lysis Mediated by a Bispecific Single Chain Antibody Expressed in Escherichia coli," Journal of Immuology, 152:5368-5374 (1994).
Guha, "Cyclin-Dependent Kinase Inhibitors Move into Phase III," Nature Reviews Drug Discovery, 11:892-894(2012).
Gul, et al., "Apoptotic Blocks and Chemotherapy Resistance: Strategies to Identify Bcl-2 Protein Signatures," Briefings in Functional Genomics and Proteomics, 7(1):27-34 (2008.
Hamid, et al., "Safety and Tumor Responses with Lambrolizumab (Anti-PD-1) in Melanoma", The Journal of Medicine, 369(2):134-144 (2013).
Hanahan, "Heritable Formation of Pancreatic β-cell Tumours in Trangenic Mice Expressing Insulin/Simian Virus 40 Oncogenes," Nature, 315:115-122 (1985).
Hanahan, et al., "The Hallmarks of Cancer," Cell, 100:57-70 (2000).
Hans, et al., "β-Carbolines Induce Apoptosis in Cultured Cerebellar Granule Neurons via the Mitochondrial Pathyway," Neuropharmacology, 48:105-117 (2005).
Harada, et al., "Survival Factor-Induced Extracellular Signal-Regulated Kinase Phosphorylastes BIM, Inhibiting Its Association with BAX and Proapoptotic Activity," PNAS, 101(43): 15313-15317 (2004).
Harada, et al., "Discovery of Potent Orally Bioavailable 17β-hydroxysteroid Dehydrogenase Type 3 Inhibitors", Bioorganic & Medicinal Chemistry, 20:3242-3254 (2012).
Harkevich, D. A., In Pharmacology 3rd Ed., Moscow, Medicine, pp. 51-55, (1987) with English translation.
Haws, et al., "E881: By an MCL-1 Dependent Mechanism, Alvocidib Potentiates the Activity of Cytarabine Mitoxantrone when Administered in a Time Sequential Regimen in AML", Hematologica 102(Suppl. 2):362 (2017).
Haws, et al., "E1204: Alvocidib Synergizes with Venetoclax in Preclinical Models of Multiple Myeloma", Hematologica 102(Suppl. 2):495 (2017).
Hemann, et al., "Suppression of Tumorigenesis by the p53 Target PUMA," PNAS, 101(25):9333-9338 (2004).
Hemann, et al., "Evasion of the p53 Tumour Surveillance Network by Tumour-Derived MYC Mutants," Nature, 436(7052):807-8011, 2005.
"Hematologic Malignancies: Regulatory Considerations for Use of Minimal Residual Disease in Development of Drug and Biological Products for Treatment, Guidance for Industry," U.S. Department of Health and Human Services, Food and Drug Administration, Oncology Center of (OCE), Center for Drug Evaluation and Research (CDER), Center for Biologics Evaluation and Research (CBER), Jan. 2020, available from https://www.fda.gov/media/134605/download. 21 pages.
Hengartner, et al., "C. elegans Cell Survival Gene ced-9 Encodes a Functional Homolog of the Mammalian Proto-Oncogene bcl-2," Cell, 76:665-676 (1994).
Hengartner, et al., "Acute Myeloid Leukaemia in Adult Patients: ESMO Clinical Practice Guidelines for diagnosis, treatment and follow-up," Annals of Oncology 31(6):697-712, 2020.
Hewings et al., "Optimization of 3,5-Dimethylisoxazole Derivatives as Potent Bromodomain Ligands" J. Med. Chem., 56:3217-3227, 2013.

Higuchi, T. and Stella, V., "Pro-drugs as Novel Delivery Systems," A.C.S. Symposium Series 14; ACS meeting, Atlantic City, NJ 1975, 118 pages.
Hillengass et al., "Minimal Residual Disease in Multiple Myeloma: Use of Magnetic Resonance Imaging," Seminars in Hematology 55(1):19-21, 2018. (Abstract Only).
Hirst, et al., "Application of Non-Parametric Regression to Quantitative Structure-Activity Relationships," Bioorganic & Medicinal Chemistry, 10:1037-1041 (2002).
Hnisz, et al., "Super-Enhancers in the Control of Cell Identity and Disease," Cell, 15 5:934-947 (2013).
Hoelzer et al., "Acute Lymphoblastic Leukaemia in adult patients: ESMO Clinical Practice Guidelines for diagnosis, treatment, and follow-up" Annals of Oncology 27(Supplement 5):v69-v82, 2016.
Holinger, et al., "Bak BH3 Peptides Antagonize Bcl-$x_L$ Function and Induce Aopoptosis Through Cytochrome c-independent Activation of Caspases," The Journal of Biological Chemistry, 274(19):13298-13304 (1999).
Hollenbach, et al., "A Comparison of Azacitidine and Decitabine Activities in Acute Myeloid Leukemia Cell Lines", PLoS One, 5(2):10 pages (2010).
Holliger, et al., ""Diabodies": Small Bivalent and Bispecific Antibody Fragments," Proc. Natl. Acad. Sci. USA, 90:6444-6448 (1993).
Hoogenboom, et al., "By-passing Immunisation-Human Antibodies form Synthetic Repertoires of Germline $V_H$ Gene Segments Rearranged In Vitro," J Mol Biol, 227:381-388 (1992).
Hopp, et al., "Predicition of Protein Antigenic Determinants from Amino Acid Sequences," Proc. Nat. Acad., Sci. USA, 78(6):3824-3828 (1981).
Hoppel, et al., "The Action of Digitonin on Rat Liver Mitochondria," Biochem J, 107:367-375 (1968).
Hourigan, et al., "Development of Therapeutic Agents for Older Patients with Acute Myelogenous Leukemia", Current Opinion in Investigational Drugs, 11(6):669-677 (2010).
Hourigan, C.S. and Karp, J.E., "Minimal Residual Disease in Acute Myeloid Leukaemia", Nature, 10:460-471 (2013).
Hsu, et al., "Nonionic Detergents Induce Dimerization Among Members of the Bcl-2 Family," The J of biol Chem., 272(21):13829-13834 (1997).
Huang, et al., "BH3-Only Proteins-Essenstial Initiators of Aopoptotic Cell Death," Cell, 103:839-842 (2000).
Huber, et al., "Profile of Venetoclax and its Potential in the Context of Treatment of Relapsed or Refractory Chronic Lymphosytic Leukemai", Onco. Targets Ther., 10:645-656 (2017).
Hunter T., "Braking the cycle", Cell, 75:839-841 (1993).
Hunter T., "Protein kinases and phosphatases: The yin and yang of protein phosphorylation and signaling", Cell, 80:225-236 (1995).
Huse, et al., "Generation of a Large Combinatorial Library of the Immunoglobulin Repertoire in Phage Lambda," Science, 246:1275-1281 (1989).
Innocenti, et al., "Flavopiridol Metabolism in Cancer Patients is Associated with the Occurance of Diarrhea," Clinical Cancer Research, 6:3400-3405 (2000).
Inohara, et al., "harakiri, a Novel Regulator of Cell Death, Encoldes a Protein that Activates Apoptosis and Interacts Selectively with Survival-Promoting Proteins Bcl-2 and Bcl-$X_L$," The EMBO Journal, 16(7):1686-1694 (1997).
Ishizawa, et al., "Mitochondrial Profiling of Acute Myeloid Leukemia in the Assessment of Response to Apoptosis Modulating Drugs," PLoS One, 10(9):e0138377 16 pages (2015).
Itzykson, R. and Fenaux, P., "Predicting the Outcome of Patients with Higher-Risk Myelodysplastic Syndrome Treated with Hypomethylating Agents", Leukemia & Lymphoma, 53(5):760-762 (2012).
Ivey et al., "Assessment of Minimal Residual Disease in Standard-Risk AML," The New England Journal of Medicine, 374(5):422-433, 2016.
Jackson, et al., "Heat Shock Induces the Release of Fibroblast Growth Factor 1 from NIH 3T3 Cells," Proc. Natl. Acad. Sci. USA, 89:10691-10695 (1992).
Jameson, et al., "A Rationally Designed CD4 Analog Inhibits Experimental Allergic Encephalomyelitis," Nature, 368:744-746 (1994).

(56) References Cited

OTHER PUBLICATIONS

Ji, et al., "A Pharmacokinetic/Pharmacodynamic Model of Tumor Lysis Syndrome in Chronic Lynphocytic Leukemia Patients Treated with Flaovpiridol", Clinical Cancer Research, 19(5):1269-1280 (2013).
Jones, et al., "Jones 1986" Nature, 321:522-525 (1986).
Jongen-Lavrencic et al., "Molecular Minimal Residual Disease in Acute Myeloid Leukemia," The New England Journal of Medicine, 378(13): 1189-1199, 2018.
Jonkers, et al., "Oncogene Addition: Sometimes a Temporary Slavery," Cancer Cell, 6:535-538 (2004).
Jornada, D.H., et al., "The Prodrug Approach: A Successful Tool for Improving Drug Solubility", Molecules, 21,42, 31 pages (2016).
Kantajian, et al., "Decitabine Improves Patient Outcomes in Myelodysplastic Syndromes", Cancer, 106(8):1794-1803 (2006).
Karp, et al., "Timed Sequential Therapy of Acute Leukemia with Flavopiridol: In Vitro Model for a Phase I Clinical Trial", Clinical Cancer Research, 9:307-315 (2003).
Karp, et al., "Phase I and Pharmacokinetic Study of Falvopiridol Followed by 1-Beta-D-Arabinofuranosylcytosine and Mitoxantrone in Relapsed and Refractory Adult Acute Leukemias", Clin Cancer Res, 11(23):8403-8412 (2005).
Karp, et al., "Sequential Flavopiridol, Cytosine Arabinoside, and Mitoxantrone: A Phase II Trial in Adults with Poor-Risk Acute Myelogenous Leukemia", Clin Cancer Res, 13(15 Pt. 1):4467-4473 (2007).
Karp, et al., "Radomized Phase II Study of Two Schedules of Flavopiridol Given as Timed Sequential Therapy with Cytosine Arabinoside and Mitoxantrone for Adults with Newly Diagnosed, Poor-Risk Acute Myelogenous Leukemia", Hematologica, 97(11):1736-1742 (2012).
Karp, et al., Phase I and Pharmacokinetic Study of Bolus-Infusion Flavopiridol Followed by Cytosine arabinoside and mitoxantrone for Acute Leukemias:, Blood, 117(12):3302-3310 (2011).
Kasper, et al., "Targeting MCL-1 Sensitizes FLT3-ITD-Positive Leukemias to Cytotoxic Therapies," Blood Cancer J, 2:10 pages (2012).
Kaur, et al., "Growth Inhibition with Reversible Cell Cycle Arrest of Carcinome Cells by Falvone L86-8275,", JNCI, 22(84):1736-1740 (1992).
Kearney M., et al., "Histopathology of in-stent restenosis in patients with peripheral artery disease", Circulation, 95:1998-2002 (1997).
Keating, et al., "Therapeutic Role of Alemtuzumab (Campath-1H) in Patients who Have Failed Fludarabine: Results of a Large International Study," Blood, 99(10):3554-3561 (2002).
Keating, et al., "Results of First Salvage Therapy for Patients Refractory to Fludarabine Regimen in Chronic Lymphocytic Leukemia," Leukemia and Lymphoma, 43(9):1755-1762 (2002).
Kelekar, et al., "Bcl-2 Family Proteins: The Role of the BH3 Domain in Apoptosis," Trends in Cell Biology, 8:324-330 (1998).
Kelekar, et al., "Bad is a BH3 Domain-Containing Protein that Forms an Inactivating Dimer with Bcl-$x_L$," Molecular and Cellular Biology, 17(12):70407046 (1997).
Kelland, L.R., "Flavopiridol, The First Cyclin-Dependent Kinase Inhibitor to Enter the Clinic: Current Status", Expert Opinion on Investigational Drugs, 9(12):2903-2911 (2000).
Kern et al., "Determination of Relapse Risk Based on Assessment of Minimal Residual Disease during Complete Remission by Multiparameter Flow Cytometry in Unselected Patients with Acute Myeloid Leukemia," Blood 104(10):3078-3085, 2004.
KG-1, ATCC® CCL-246™, ATCC Product Sheet, 3 pages, May 31, 2013.
Kim et al., "Alvocidib Potentiates the Activity of Cytarabine and Mitoxantrone through the Targeting of MCL-1 When Administered in a Time Sequential Regimen in AML," Blood 126(23), 3799, 2015.
Kim, W., et al., "Alvocidib Potentiates the Activity of Azacytidine in an MCL-1-Dependent Fashion", Blood, 126(23):Abstract 1343, 3 pages (2015).
Kim, et al., "Abstract 3728: Targeting MCL-1 Expression Through the Inhibition of CDK9 and Super Enhancer Driven Transcription, Offers Multiple Opportunities for Rational Drug Combinations", Cancer Research, 76(14 Suppl.):3728 (2016).
Kim, et al., "Alvocidib Synergizes with Cytarabine and Daunorubicin (7+3) in Preclinical Models of Acute Myeloid Leukemia", EHA Learning Center, May 18, 2017, retrieved from https://learningcenter/ ehaweb.org/eha/2017/22nd/1080678, 3 pages. (2016).
Kim, et al., "TP-1287, an oral prodrug of the cyclin-dependent kinase-9 inhibitor alvocidib", EHA Library Jun. 9, 2016. Retrieved on Jan. 24, 2020 URL:https://library.ehaweb.org/eha/2016/21st/ 132440/clifford.whatcott.tp-1287.prodrug.of.the.cyclin-dependent. kinase-9.htm; poster.
Kim, et al., "The CDK9 Inhibitor, Alvocidib, Potentiates the Non-Clinical Activity of Azacytidine or Decitabine in an MCL-1-Dependent Fashio, Supporting Clinical Exploration of a Decitabine and Alvocidib Combination", Blood, 132(suppl 1):4355—6 pages (2018).
Kimura, et al., "Antiproliferative and Antitumor Effects fo Azacitidine Against Human Myelodysplastic Syndrome Cell Line SKM-1", Anticancer Research, 32:795-798 (2012.
Kitada, et al., "Protein Kinase Inhibitors Flavoripidol and 7-hydroxy-staurosporine Down-Regulate Antiapoptosis Proteins in B-Cell Chronic Lymphocytic Leukemia," Blood, 96(2):393-397 (2000).
Klaeger, et al., "The Target Landscape of Clinical Kinase Drugs", Science, 358:1148-1164 (2017).
Knutson, et al., "Synergistic Anti-Tumor Activity of EZH2 Inhibitors and Glucocorticoid Receptor Agonists in Models of Germinal Center Non-Hodgkin Lymphomas", PLoS One, 9(12):e111840 (2014).
Köhler, et al., "Continuous Cultures of Fused Cells Secreting Antibody of Predefined Specificity," Nature, 256:495-497 (1975).
König, et al., "The Novel Cyclin-Dependent Kinase Inhibitor Flavopiridol Downregulates Bcl-2 and Induces Growth Arrest and Aopotosis in Chronic B-Cell Leukemia Lines," Blood, 90(11):4307-4312 (1997).
Konopleva et al., "BCL-2 Inhibition in AML: An Unexpected Bonus?" Blood 132(10):1007-1012, 2018.
Korsmeyer, et al., "Pro-Apoptotic Cascade Activates BID, which Oligomerizes BAK or BAX into Pores that Result in the Release of Cytochrome c," Cell Death and Differentiation, 7:1166-1173 (2000).
Kozbor, et al., "The Production of Monoclonal Antibodies from Human Lymphocytes," Immunology Today, 4(3):72-79 (1983).
Kryštof, et al., "Cyclin-Dependent Kinase Inhibitors as Anticancer Drugs," Current Drug Targets, 11:291-302 (2010).
Kumar, S., et al., "International Myeloma Working Group Consensus Criteria for Response and Minimal Residual Disease Assesment in Multiple Myeloma," Lancet Oncology, 17:e328-e346 (2016).
Kuwana, et al., "Bid, Bax, and Lipids Cooperate to Form Supramolecular Openings in the Outer Mitochondrial Membrane," Cell, 111:331-342 (2002).
Kuwana, et al., "BH3 Domains of BH3-Only Proteins Differentially Regulate Bax-Mediated Mitochondrial Membrane Permeabilization Both Directly and Indirectly," Molecular Cell, 17:525-535 (2005).
Kyte, et al., "A Simple Method for Displaying the Hydropathic Character of a Protein," J. Mol Biol, 157:105-132 (1982).
LA Vieira, et al., "Cell Permeable BH3-Peptides Overcome the Cytoprotective Effect of Bcl-2 and Bcl-$X_L$," Oncogene, 21:1963-1977 (2002).
Labi, et al., "Targeting the Bcl-2-Regulated Apoptosis Pathyway by BH3 Mimetics: A Breakthrough in Anticancer Therapy?," Cell Death and Differentiation, 15:977-987 (2008).
Landgren et al., "MRD Testing in Multiple Myeloma: The Main Future Driver for Modern Tailored Treatment," Seminars in Hematology 55(1):44-50, 2018. (Abstract Only).
Landgren, "MRD Testing in Multiple Myeloma: From a Surrogate Marker of Clinical Outcomes to an Every-Day Clinical Tool," Seminars in Hematology 55(1):1-3, 2018. (Abstract Only).
Lazarus, et al., "High-Dose Cytosine Arabinoside and Daunorubicin as Primary Therapy in Elderly Patients with Acute Myelogenous Leukemia", Cancer, 63:1055-1059 (1989).
Lee DJ et al., "Zella 101: Phase 1 Study of Alvocidib Followed by 7+3 Induction in Newly Diagnosed AML Patients," European Hematology Association—24th Congress, 2019, Hemasphere, 3:S1:94.

(56) References Cited

OTHER PUBLICATIONS

Lee, D., et al., "Abstract PF285: Zella 101 Phase I Study of Alvocidib Followed by 7+3 Induction in Newly Diagnosed AML Patients" as present during the 24th Annual Congress of the European Hematology Association 2019, HemaSphere, 3:S1: 94 (2019).
Lemke, et al., "Immunobiology of the TAM Receptors," Nature Reviews Immunology, 8:327-336 (2008).
Leo, et al., "Characterization of the Antiapoptotic Bcl-2 Family Member Myeloid Cell Leukemia-1 (Mcl-1) and the Stimulation of its Message by Gonadotropins in the Rat Ovary," Endocrinology, 140(12):5469-5477 (1999).
Letai, et al., "Distinct BH3 Domains Either Sensitize or Activate Mitochondrial Apoptosis, Serving as Prototype Cancer Therapeutics," Cancer Cell, 2:183-192 (2002).
Letai, et al., "BH3 Domains as BCL-2 Inhibitors: Prototype Cancer Therapeutics," Expert Opin Biol. Ther., 3(2):293-304 (2003).
Letai, et al., "Antiapoptotic BCL-2 is Required for Maintenance of a Model Leukemia," Cancer Cell, 6:241-249 (2004).
Letai, et al., "The BCL-2 Network: Mechanistic Insights and Therapeutic Potential," Drug Discovery Today: Disease Mechanisms, 2(2):145-151 (2005).
Letai, et al., "Perturbing Cancer Cell Mitochondria to Learn How to Kill Cancer with BH3 Profiling," Dana Farber Cancer Institute,, Broad Institute, Cell Circuits and Epigenomics, 47 pages, Jul. 28, 2014.
Li, et al., "tsg101: A Novel Tumor Susceptibility Gene Isolated by Controlled Homozygous Functional Knockout of Allelic Loci in Mammalian Cells," Cell, 85:319-329 (1996).
Li, et al., "Cleavage of BID by Capase 8 Mediates the Mitochondrial Damage in the Fas Pathyway of Apoptosis," Cell, 94:491-501 (1998).
Li, et al., "Endonuclease G is an Aopototic DNase When Released from Mitochondria," Nature, 412:95-99 (2001).
Lin, C.Y., et al., "Transcriptional Amplification in Turmor Cells with Elevated c-Myc", Cell, 151:56-67 (2012).
Lin, K.H., et al., "Targeting MCL-1/BCL-XL Forestalls the Acquisition of Resistance to ABT-1999 in Acutes Myeloid Leukemia", Scientific Reports, 6(1): 9 Pages (2016).
Lin, T.S., et al., "Flavopiridol Given as a 30-min Intravenous (IV) Bolus Followed by a 4-hr Continuous IV Infusion (CIVI) Results in Clinical Activity and Tumor Lysis in Refractory Chronic Lymphocytic Leukemia (CLL)," Journal of Clinical Oncology, 2004 ASCO Annual Meeting Proceedings (Post Meeting Edition) 22(14S):Abstract No. 6564, 1 page (2004).
Lin, T.S., et al., "Seventy-Two Hour Continuous Infusion Flavopiridol in Relapsed and Refractory Mantle Cell Lymphoma," Leukemia & Lymphoma, 43(4):793-797 (2002).
Lin, T.S., et al., "Phase II Study of Flavopiridol in Relapsed Chronic Lymphocytic Leukemia Demonstrating High Response Rates in Genetically High-Risk Disease", Journal of Clinical Oncology, 27(35):6012-6018 (2009).
Lindsley, R.C., et al., "Acute Myeloid Leukemia Ontogeny is Defined by Distinct Somatic Mutations", Blood, 125(9):1367-1376 (2015).
Linenberger, K.J. and Bretz, S.L., "Biochemistry Students' Ideas About Shape and Charge in Enzyme-Substrate Interactions", Biochemistry and Molecularbiology Education, 203-212 (2014).
Litzow, M.R., et al., "A Randomized Trial of Three Novel Regimens for Recurrent Acute Myeloid Leukemia Demonstrates the Continuing Challenge of Treating this Difficult Disease", Am. J. of Hematol, 94(1):111-117 (2019).
Liu, et al., "Bax Conformation Change is a Crucial Step for PUMA-Mediated Apoptosis in Human Leukemia," Biochemical and Biophysical Research Communications, 310:956-962 (2003).
Liu, et al., "BH3-Based Fusion Artificial Peptide Induces Apoptosis and Targets Human Colon Cancer," Molecular Therapy, 17:1509-1516 (2009).
Liu, et al., "CDKI-17, a Novel CDK9 Inhibitor, is Preferentially Cytotoxic to Cancer Cells Compared to Flavopiridol," Int. J. Cancer, 130:1216-1226 (2012).
Lonberg, et al., "Antigen-Specific Human Antibodies from Mice Comprising Four Distinct Genetic Modification," Nature 368:856-859 (1994).
Londoño, et al., "A Reliable Method for Quantification of Splice Variants Using RT-qPCR", BMC Mol. Biol., 17(8):1-12 (2016).
Long, et al., "Optimization and Validation of Mitochondria-Based Functional Assay as a Useful Tool to Identify BH3-Like Molecules Selectively Targeting Anti-Apoptotic Bcl-2 Proteins," BMC Biotechnology, 13:45—10 pages (2013).
Lovén, et al., "Selective Inhibition of Tumor Oncogenes by Disruption of Super-Enhancers," Cell, 153(2):320-334 (2013).
Lozanski, et al., "Alemtuzumab is an Effective Therapy for Chronic Lymphocytic Leukemia with p53 Mutations and Deletions," Blood, 103(9):3278-3281 (2004).
Lu, H., et al., "Compensatory Induction of MYC Expression by Sustained CDK9 Inhibition via a BRD4-dependent Mechanism", eLife, 26 pages Jun. 17, 2015.
Luo, et al., "Bid, a Bcl2 Interacting Protein, Mediates Cytochrome c Release from Mitochondria in Response to Activation of Cell Surface Death Receptors," Cell, 94:481-490 (1998).
Lutter, et al., "The Pro-Apoptotic Bcl-2 Family Member tBid Localizes to Mitochondrial Conact Sites," BMC Cell Biology, 2:22—9 pages (2001).
Malcovati et al., "Diagnosis and Treatment of Primary Myelodysplastic Syndromes in Adults: Recommendations From the European LeukemiaNet," Blood 122(17):2943-2964, 2013.
Malumbres, "Cyclin-Dependent Kinases", Genome Biol., 15(122):1-10 (2014).
Mann M. J., et al., "Cell cycle inhibition preserves endothelial function in genetically engineered rabbit vein grafts", J. Clin. Invest., 99:1295-1301 (1997).
Marani, et al., "Identification of Novel Isoforms of the BH3 Domain Protein Bim which Directly Activates Bax to Trigger Apoptosis," Molecular and Cellular Biology, 22(11):3577-3589 (2002).
Marks, et al., "By-Passing Immunization: Human Antibodies from V-gene Libraries Displayed on Phage," J. Mol. Biol., 222:581-597 (1991).
Marks, et al., "By-Passing Immunization: Building High Affinity Human Antibodies By Chain Shuffling," Nature BioTechnology, 10:779-783 (1992).
Martin, "Opening the Cellular Poison Cabinet," Science, 330:1330-1331 (2010).
Mason, et al., "The Hypogonadal Mouse: Reproductive Functions Restored by Gene Therapy," Science, 234:1372-1378 (1986).
Matasushita, et al., "A High-Efficiency Protein Transduction System Demonstrating the Role of PKA in Long-Lasting Long-Term Potentiation," The Journal of Neuroscience, 21(16):6000-6007 (2001).
Matsumura, Y., et al., "1959-CDK9 Inhibition Combined with Hypomethylating Agents Target MCL-1 Dependency in MDS and AML", AACR Annual Meeting 2021—Virtual—Poster to be presented during Session PO.MCB06.01—Cell Cycle on Apr. 10, 2021, downloaded from AACR website, URL: https://www.abstractsonline.com/pp8/#!/9325/presentation/3238 on Mar. 30, 2021, 2 pages.
Matsumura Y et al., "CDK9 Inhibition Combined with Hypomethylating Agents Target MCL-1 Dependency in MDS and AML," American Association for Cancer Research—112th Annual Meeting, Poster, 2021.
Matsumura Y, et al., "Pharmacodynamic biomarker strategies for CDK9 inhibition," American Association for Cancer Research—111th Annual Meeting, Poster, 2020.
Matsumura, Y., et al., "Abstract 5813: Pharmacodynamic Biomarker Strategies for CDK9 Inhibition" as presented Annual Meeting of the American Associateion for Cancer Research 2020; Apr. 27-28 and Jun. 22-24, 2020 in Philadelphia, PA, Cancer Res., 80(Supplement 16):4 pages.
Matsuzaki, et al., "Why and How are Peptide-Lipid Interactions Utilized for Self Defence?," Biochem. Soc. Transactions, 29:598-601 (2001).
Mayer, "Induction of apoptosis by flavopiridol unrelated to cell cycle arrest in germ cell tumour derived cell lines," Invest New Drugs 23(3):205-211, 2005.

(56) References Cited

OTHER PUBLICATIONS

McDonnell, et al., "bcl-2-Immunoglobulin Transgenic Mice Demostrate Extended B Cell Survival and Follicular Lymphoproliferation," Cell, 57:79-88 (1989).
Means, et al., "Modifications to Change Properties", in *Chemical Modification of Proteins*, (San Francisco: Holden-Day, Inc.), Chapter 3, pp. 35-54 (1971).
Mian, S.A., et al., "Splicesome Mutations Exhibit Specific Associations with Epigenetic Modifiers and Proto-Oncogenes Mutated in Myelodysplastic Syndrome", Haematologica, 98(7): 1058-1066 (2013).
Mikhael et al., "Treatment of Multiple Myeloma: ASCO and CCO Joint Clinical Practice Guideline," J Clin Oncol 37(14):1228-1264, 2019. (40 pages).
Miller, et al., "Therapeutic Strategies to Enhance the Anticancer Efficacy of Histone Deacetylase Inhibitors," Journal of Biomedicine and Biotechnology, 2011:514261—17 pages (2011).
Milstein, et al., "Hybrid Hybridomas and their Use in Immunohistochemistry," Nature, 305:537-540 (1983).
Mintz G.S., "In-stent restenosis: the Washington Hospital Center experience", Am. J. Cardiol., 81:7E-13E (1998).
Mintz G.S., "Arterial remodeling after coronary angioplasty: a serial intravascular ultrasound study", Circulation,; 94:35-43 (1996).
Mirguet, O., et al., "Discovery of Epigenetic Regulator I-BET762: Lease Optimization to Afford a Clinical Candidate Inhibitor of the BET Bromodomains", Journal of Medicinal Chemistry, 56:7501-7515 (2013).
Molassiotis, et al., "Use of Complementary and Alternative Medicine in Cancer Patients: A European Survey", Annals of Oncology, 16:655-663 (2005).
Montero, et al., "Drug-Induced Death Signaling Strategy Rapidly Predicts Cancer Response to Chemotherapy," Cell, 160:977-989 (2015).
Montesinos, et al., "Tumor Lysis Syndrome in Patients with Acute Myeloid Leukemia: Identification of Risk Factors and Development of a Predictive Model", Haematologica, 93:67-74 (2008).
Moore, et al., "BH3 Profiling—Measuring Integrated Function of the Mitochondrial Apoptotic Pathway to Predict Cell Fate Decisions," Cancer Letters, 332(2):202-205 (2013).
Moore, et al., "Chronic Lymphocytic Leukemia Requires BCL2 to Sequester Prodeath BIM, Explaining Sensitivity to BCL2 Antagonist ABT-737," The Journal of Clinical Investigation , 117(1):112-121 (2007).
Morishita R., et al., "A gene therapy strategy using a transcription factor decoy of the E2F binding site inhibits smooth muscle proliferation in vivo", Proc. Natl. Acad. Sci. USA, 92:5855-5859 (1995).
Morita, Y., et al., "Phase 1 Study of Alvocidib (DSP-2033) in Combination with Cytarabine/Mitoxantrone (ACM) or Cytarabine/Daunorubicin (A=7+3) in Japanese Patients (pts) with Acute Myeloid Leukemia (AML)", Blood, 136(Supplement 1):4 pages (2020).
Morita, Y. et al., "Phase 1 Study of Alvocidib (DSP-2033) in Combination with Cytarabine/Mitoxantrone (ACM) or Cytarabine/Daunorubicin (A+7+3) in Japanese Patients (Pts) with Acute Myeloid Leukemia (AML)," American Society of Hematology—62nd Annual Meeting. 2020.
Moros, et al., "Synergistic Antitumor Activity of Lenalidomide with the BET Bromodomain Inhibitor CPI203 in Bortezomib-Resistant Mantle Cell Lymphoma", Leukemia, 28(10):2049-2059 (2015).
Morrison, Success in Specification, Nature, 368:812-813 (1994).
Motwani, M., et al., "Sequential Dependent Enhancement of Caspase Activation and Apoptosis by Flavopiridol on Paclitaxel-Treated Human Gastric and Breast Cancer Cells", Clinical Cancer Research, The American Association for Cancer Research, 5(7):1876-1883 (1996).
Motwani, M., et al., "Docetaxel and Navelbine Induced Apoptosis is Enhanced by Flavopiridol (Flavo) in Breast Cancer Cells and is Sequence Dependent", Proceedings of the Annual Meeting of The American Association for Cancer Research, New York, NY, 41:143 (2000).

Muchmore, et al., "X-ray and NMR Structure of Human Bcl-$x_L$, an Inhibitor of Programmed Cell Death," Nature, 381:335-341 (1996).
Munson, et al., "Ligand: A Versatile Computerized Approach for Characterization of Ligand Binding Systems," Analytical Biochemistry, 107:220-239 (1980).
Murthi, et al., "Structure-Activity Relationship Studies of Flavopiridol Analogues," Bioorganic & Medicinal Chemistry Letters, 10:1037-1041 (2000).
Nagai, et al., Studies on Psychotropic Agents. VI. Synthesis of 1'-Methylspiro[6-fluoroindan-1, 3'-pyrrolidine]-3-one and Related Compounds, Chem and Pharm Bull, 28(5):1387-1393 (1980).
Naik, et al., "An Antiinflammatory Cum Immunomodulatory Piperidinylbenzopyranone from Dysoxylum Binectariferum: Isolation, Structure and Total Synthesis," Tetrahedron, 44(7):2081-2086 (1988).
Nakanishi, T. and Tamai, I., "Solute Carrier Transporters as Targets for Drug Delivery and Pharmacological Intervention for Chemotherapy," J. Pharm Sci, vol. 100; 3731-3750 (2011).
Nakano, et al., "PUMA, a Novel Proapoptotic Gene, is Induced by p53," Molecular Cell, 7:683-694 (2001).
Narita, et al., "Bax Interacts with the Permeability Transition Pore to Induce Permeability Transition and Cytochrome c Release in Isolated Mitochondria," Proc. Natl. Acad. Sci. USA, 95:14681-14686 (1998).
NCCN Clinical Practice Guidelines in Oncology (NCCN Guidelines®) Acute Myeloid Leukemia, Version 2.2014, NCCN.org, 6 pages.
Neuberger, "Generating High-Avidity Human Mabs in Mice," Nature Biotechnology, 14:826 (1996).
Nguyen, A.N., et al., "Azacitidine and Decitabine have Different Mechanisms of Action in Non-Small Cell Lung Cancer Cell Lines", Lung Cancer: Targets and Therapy, 1:119-140 (2010).
NICE guidelines, "Myeloma: Diagnosis and Management," National Institute for Health and Care Excellence: 1-27, 2016.
Noel, et al., "Development of the BET Bromodomain Inhibitor OTX015," Proceedings of the AACR-NC1-EORTC International Conference: Molecular Tagets and Cancer Therapeutics, Boston, MA and Philadelphia, PA, Oct. 19-23, 2013, Mol. Cancer Ther, 12(11 Suppl):Abstract C244—4pages (2013).
O'Brien, et al., "Phase I to II Multicenter Study of Oblimersen Sodium, a Bcl-2 Antisense Oligonucleotide in Patients with Advanced Chronic Lymphocytic Leukemia," Journal of Clinical Oncology, 23(30):7697-7702 (2005).
O'Brien E. R., et al., "Proliferation in primary and restenotic coronary atherectomy tissue: implications for anti-proliferative therapy", Circ. Res., 73:223-231 (1993).
O'Connor, et al., "Bim: A Novel Member of the Bcl-2 Family That Promotes Apoptosis," The EMBO Journal, 17(2):384-395 (1998).
Oda, et al., "Noxa, a BH3-Only Member of the Bcl-2 Family and Candidate Mediator of p53-Induced Apoptosis," Science, 288:1053-1058 (2000).
Odore, et al., Abstract LB-231, "A Phase I Pharmacokinetic Study of OXT015 for the Treatment of Patients with Hemato Malignancies", Proceedings of AACR Annual Meeting, Apr. 5-9, 2014, San Diego, CA.
Oh, et al., Conformational Changes in BID, a Pro-Apoptotic BCL-2 Family Member, Upon Membrane Binding, The Journal of Biological Chemistry, 280(1):753-767 (2005).
Okamoto et al., "Increased antitumor potential of the raloxifene prodrug, raloxifene diphosphate," *Int. J. Cancer* 122:2142-2147, 2008.
Oken, et al., "Toxicity and Response Criteria of the Eastern Cooperative Oncology Group", Am. J. Clin. Oncol., 5(6):649-655 (1982).
Oltersdorf, et al., "An Inhibitor of Bcl-2 Family Proteins Induces Regression of Solid Tumours," Nature, 435:677-681 (2005).
Opferman, et al., "Development and Maintenance of B and T Lymphocytes Requires Antiapoptotic MCL-1," Nature, 426:671-676 (2003).
Opferman, et al., "Obligate Role of Anti-Apoptotic MCL-1 in the Survival of Hematopoietic Stem Cells", Science, 307:1101-1104 (2005).

(56) References Cited

OTHER PUBLICATIONS

Opperman, et al., "High-content screening identifies kinase inhibitors that overcome venetoclax resistance in activated CLL cells", Blood, 128(7):934-347 (2016).
Oscier, et al., "Multivariate Analysis of Prognostic Factors in CLL: Clinical Stage, IGVH Gene Mutational Status, and Loss or Mutation of the p53 Gene are Independent Prognostic Factors," Blood, 100(4):1177-1184 (2002).
Otsuka, et al., "Effect of Polymorphic Forms of Bulk Powders on Pharmaceutical Properties of Carbamazepine Granules," Chem and Pharm Bull, 47(6):852-856 (1999).
Pandit-Taskar, "Functional Imaging Methods for Assessment of Minimal Residual Disease in Multiple Myeloma: Current Status and Novel ImmunoPET Based Methods," Seminars in Hematology, 55(1):22-32, 2018.
Paoluzzi, et al., "The BH3-Only Mimetic ABT-737 Synergizes the Antineoplastic Activity of Proteasome Inhibitors in Lymphoid Malignancies," Blood, 112:2906-2916 (2008).
Papaemmanuil et al., "Genomic Classification and Prognosis in Acute Myeloid Leukemia," The New England Journal of Medicine 374(23):2209-2221, 2016.
Paquin, et al., "Design and Synthesis of 4-[(s-triazin-2-ylamino)methyl]-N-(2-aminophenyl)-benzamides and their Analogues as a Novel Class of Histone Deacetylase Inhibitors," Bioorganic & Medicinal Chemistry Letters, 18:1067-1071 (2008).
Park D. S., et al., "Inhibitors of cyclin-dependent kinases promote survival of post-mitotic neuronally differentiated PC12 cells and sympathetic neurons", J. Biol. Chem., 271:8161-8169 (1996).
Parker, et al., "Early Induction of Apoptosis in Hematopoietic Cell Lines After Exposure to Flavopiridol," Blood, 91(2):458-465 (1998).
Parovichnikova, E., et al., "The MRD-Negativity Rate Measured By Flow Cytometry After the 1st and 2nd Induction Course Among CR AML Patients from Different Cytogenetic Subgroups Does Not Differ Though the Morphological CR Achievement Does", Blood, 132(Suppl1:1495, 6 pages (2018).
Parry, et al., "Dinaciclib (SCH 727965), a Novel and Potent Cyclin-Dependent Kinase Inhibitor," Mol Cancer Ther, 9(8):2344-2353 (2010).
Paruch, et al., "Discovery of Dinaciclib (SCH 727965): A Potent and Selective Inhibitor of Cyclin Dependent Kinases," ACS Med. Chem. Lett., 1:204-208 (2010).
Payne D. M., et al., "Identification of the regulatory phosphorylation sites in pp42/mitogen-activated protein kinase (MAP kinase)", EMBO J., 10:885-892 (1991).
Pepper, et al., "Flavopiridol Circumvents Bcl-2 Family Mediated Inhibition of Apoptosis and Drug Resistance in B-Cell Chronic Lymphocytic Leukaemia", Br. J. Haematol, 114(1):70-77 (2001).
Perkins, et al., "Frequency and Type of Serious Infections in Fludarabine-Refractory B-Cell Chronic Lymphocytic Leukemia and Small Lyphocytic Lymphoma," Cancer, 94(7):2033-2039 (2002).
Perrot et al., "Minimal Residual Disease Negativity Using Deep Sequencing is a Major Prognostic Factor in Multiple Myeloma," Blood 132(23):2456-2464, 2018.
Phelps, et al., "Clinical Response and Pharmacokinetics from a Phase I Study of an Active Dosing Schedule of Flavopiridol in Relapsed Chronic Lymphocytic Leukemia", Blood, 113(12):2637-2645 (2009).
Phillips, et al., "Loss in MCL-1 Function Sensitizes Non-Hodgkin's Lymphoma Cell Lines to the BCL-2-Selective Inhibitor Venetoclax (ABT-199)", Blood Cancer J., 5:e368, 8 pages (2015).
Picaud, et al., "RVX-208, an Inhibitor of BET Transcriptional Regulators with Selectivity for the Second Bromodomain", PNAS, 110(49):19754-19759 (2013).
Picaud, et al., "PFI-1, a Highly Selective Protein Interaction Inhibitor, Targeting BET Bromodomains," Cancer Res., 73(II):3336-3346 (2013).
Piekarz, et al., "Inhibitor of Histone Deacetylation, Depsipeptide (FR901228), in the Treatment of Peripheral and Cutaneous T-Cell Lymphoma: a Case Report," Blood, 98:2865-2868 (2001).
Pierceall, et al., "BH3 Profiling Discriminates Response to Cytarabine-Based Treatment of Acute Myelogenous Leukemia," Molecular Cancer Therapeutics, 12(12):2940-2949 (2013).
Pierceall, et al., "Mcl-1 Dependence Predicts Response to Vorinostat and Gemtuzumab Ozogamicin in Acute Myeloid Leukemia," Leukemia Research, 38(5):564-568 (2014).
Pierceall, et al., "Mitochondrial Priming of Chronic Lymphocytic Leukemia Patients Associates Bcl-$x_L$ Dependence with Alvocidib Response," Leukemia 28(11):2251-2254 (2014).
Pinkert, et al., "An Albumin Enhancer Located 10kb Upstream Functions Along with its Promoter to Direct Efficient, Liver-Specific Expression in Transgenic Mice," Genes & Development, 1:268-276 (1987).
Plumb, et al., "Pharmacodynamic Response and Inhibition of Growth of Human Tumor Xenografts by the Novel Histone Deacetylase Inhibitor PXD101," Mol Cancer Ther, 2:721-728 (2003).
Pode-Shakked, et al., "Development Tumourigeneisi: NCAM as a Putative Marker for the Malignant Renal Stem/Progenitor Cell Population," J Cell Mol Med, 13(8B):1792-1808 (2009).
Polster, et al., "BH3 Death Domain Peptide Induces Cell Type-Selective Mitochondrial Outer Membrante Permeability," The J of Biol Chem, 276(41):37887-37894 (2001).
Presta, "Antibody Engineering," Curr Opin in Struc Biol, 2:593-596 (1992).
Pritzker, "Cancer Biomarkers: Easier Said than Done," Clin Chem, 48(8):1147-1150 (2002).
Pugh, "Circulating Tumour DNA for Detecting Minimal Residual Disease in Multiple Myeloma," Seminars in Hematology 55:38-40, 2018.
Putcha, et al., "Induction of BIM, a Proapoptotic BH3-Only BCL-2 Family Member, is Critical for Neuronal Aopotosis," Neuron, 29:615-628 (2001).
Puthalakath, et al., "The Proapoptotic Activity of the Bcl-2 Family Member Bim is Regulated by Interaction with the Dynein Motor Complex," Mol. Cell, 3:287-296 (1999).
Puthalakath, et al., "Bmf: A Proapoptotic BH3-Only Protein Regulated by Interaction with the Myosin V Actin Motor Complex, Activated by Anoikis," Science, 293:1829-1832 (2001).
Puthalakath, et al., "Keeping Killers on a Tight Leash: Transcriptional and Post-Translational Control of the Pro-Apoptotic Activity of BH3-Only Proteins," Cell Death and Differentiation, 9:505-512 (2002).
Qi, et al., "A Subset of Small Cell Lunng Cancer (SCLC) Cell Lines is MCL-1-Dependent and Responds to Cyclin-Dependent Kinase (CDK)9 Inhibition in vitro and in vivo", Cancer Research, 72(8): Suppl. 1, Abstract 2016, 4 pages, (2012).
Quinsay, et al. "Pro-Apoptotic Bnip3 Mediates Penneabilization of Mitochondria and Release of Cytochrome c via a Novel Mechanism," Circulation, 118:Abstract 1783 (S388)—5 pages (2008).
Quinsay, et al., "Bnip3 Mediates Permeabilization of Mitochondria and Release of Cytochrome c via a Novel Mechanism," J Mol Cell Cardiol, 48(6):1146-1156 (2010).
Raff, "Social Controls on Cell Survival and Cell Death," Nature, 356:397-400 (1992).
Ramsey, H.E., et al., "A Novel MCL1 Inhibitor Combined with Venetoclax Rescues Venetoclax-Resistant Acute Myelogenous Leukemia", Cancer Discov, 8(12):1566-1581 (2018).
Rassenti, et al., "ZAP-70 Compared with Immunoglobulin Heavy-Chain Gene Mutation Status as a Predictor of Disease Progression in Chronic Lymphocytic Leukemia," NEJM, 351:893-901 (2004).
Ravandi, et al., "Evaluating Measurable Residual Disease in Acute Myeloid Leukemia", Blood Adv., 2(11):1356-1366 (2018).
Ray, et al., "BNIP3 Heterodimerizes with Bcl-2/Bcl-$X_L$ and Induces Cell Death Independent of a Bcl-2 Homology 3 (BH3) Domain at Both Mitochondrial and Nonmitochondrial Sites," The J. of Biol. Chem., 275(2):1439-1448 (2000).
Raychaudhuri, "Low Probability Bid-Bax Reaction Generates Heterogeneity in Apoptosis Resistance of Cancer and Cancer Stem Cells," arXiv:1108.2091[a-bio.MN], 17 pages (2011).
Ren, et al., "BID, BIM and PUMA are Essential for Activation of the BAX- and BAK-Dependent Cell Death Program," Science, 330:1390-1393 (2010).

(56) References Cited

OTHER PUBLICATIONS

Rezaei, et al., "Leukemia Markers Expression of Peripheral Blood vs. Bone Marrow Blasts Using Flow Cytometry," Medical Science Monitor, 9(8):CR359-CR362 (2003).

Riabov, V., et al., "Preclinical Assessment of Alvocidib in Combination with 5-Azacytidine in High-Risk Myelodysplastic Syndromes", Blood, 138(Supplement 1):4649 (2021).

Richard, D.., et al., "Hydroxyquinoline-derived compounds and analoguing of selective Mcl-1 inhibitors using a functional biomarker"Bioorg Med Chem. 21(21):6642-9, 2013.

Richon, et al., "A Class of Hybrid Polar Inducers of Transformed Cell Differentiation Inhibits Histone Deacetylases," Proc. Natl. Acad. Sci. USA, 95:3003-3007 (1998).

Riechmann, et al., "Reshaping Human Antibodies for Therapy," Nature, 332:323-327 (1988).

Rollins-Raval, et al., "The Value of Immunohistochemistry for CD14, CD123, CD33, Myeloperoxidase and CD68R in the Diagnosis of Acute and Chronic Myelomonocytic Leukemias," Histopathology, 60:933-942 (2012).

Rosenblatt, et al., "PD-1 Blockade by CT-011, Anti PD-1 Antibody, Enhances Ex-Vivo T Cell Responses to Autologous Dendritic/Myeloma Fusion Vaccine", J. Immunother, 34(5):409-418 (2011).

Roshal, "Minimal Residual Disease Detection by Flow Cytometry in Multiple Myeloma: Why and How?" Seminars in Hematology 55(1):4-12, 2018.

Rothbard, et al., "Conjugation of Arginine Oligomers to Cyclosporin A Facilitates Topical Delivery and Inhibition of Inflammation," Nature Medicine, 6(11):1253-1257 (2000).

Rudeck, et al., "Clinical Pharmacology of Flavopiridol Following a 72-Hour Continuous Infusion," Annals of Pharmacotherapy, 37:1369-1374 (2003).

Ruef, J., "Induction of vascular endothelial growth factor in balloon-injured baboon arteries," Circulation Res, 81:24-33 (1997).

Ruef, J., "Induction of rat aortic smooth muscle cell growth by the lipid peroxidation product 4-hydroxy-2-nonenal," Circulation, 97:1071-1078 (1998).

Ruef, J., "Flavopiridol Inhibits Smooth Muscle Cell Proliferation In Vitro and Neointimal Formation In Vivo After Carotid Injury in the Rat," Circulation, 100(6):659-665 (1999).

Ryan, et al., "Heightened Mitochondrial Priming is the Basis for Apoptotic Hypersensitivity of CD4$^+$ CD8$^+$ Thymocytes," PNAS, 107(29):12895-12900 (2010).

Ryan, et al., "BH3 Profiling in Whole Cells, Fluorimeter of FACS," Methods, 61(2):156-164 (2013).

Saito, et al., "A Synthetic Inhibitor of Histone Deacetylase, MS-27-275, with Marked In Vivo Antitumor Activity Against Human Tumors," Proc. Natl. Acad. Sci. USA, 96:4592-4597 (1999).

Salomon, C.J., et al., "Recent Developments in Chemical Deprotection of Ester Functional Groups", Tetrahedron, 49(18):3691-3748 (1993).

Samson, et al., "A 35 Amino Acid Fragment of Leptin Inhibits Feeding in the Rat," Endocrinology, 137(11):5182-5185 (1996).

San Miguel et al., "Early Immunophenotypical Evaluation of Minimal Residual Disease in Acute Myeloid Leukemia Identifies Different Patient Risk Groups and May Contribute to Postinduction Treatment Stratification," Blood 98(6):1746-1751, 2001.

Sata, M., et al., "Fas ligand gene transfer to the vessel wall inhibits neointima formation and overrides the adenovirus-mediated T cell response", Proc. Natl. Acad. Sci. USA, 95:1213-1217 (1998).

Sattler, et al., "Structure of Bcl-$x_L$-Bak Peptide Complex: Recognition Between Regulators of Apoptosis," Science, 275:983-986 (1997).

Sausville, et al., "Inhibition of CDKs as a Therapeutic Modality," Ann NY Acad. of Sci., 910:207-222 (2000).

Schimmer, et al., "The BH3 Domain of BAD Fused to the Antennapedia Peptide Induces Apoptosis via it Alpha Helical Structure and Independent of Bcl-2," Cell Death and Differentiation, 8:725-733 (2001).

Schuurhuis, et al., "Minimal/Measurable Residual Disease in AML: A Consensus Document from the Duropean LeukemiaNet MRD Working Party", Blood, 131(12):1275-1291 (2018).

Schwartz, G.K., et al., "Phase I Trial of Sequential Paclitaxel and Cisplatin in Combination with the Cyclin Dependent Kinase Inhibitor Flavopiridol (Flavo) in Patients with Advanced Solid Tumors", Clinical Cancer Research, 5, p. 3754s, abstract #122 (1999).

Schwartz, et al., "The intima: soil for atherosclerosis and restenosis", Circ. Res., 77:445-465 (1995).

Schwartz, G.K., et al., "Phase I Study of the Cyclin-Dependent Kinase Inhibitor flavopiridol in combination with Paclitaxel in Patients with Advanced Solid Tumors", Journal of Clinical Oncology, 20(8) Apr. 15, 2002: pp. 2157-2170.

Schwartz, et al, "Phase II Study of the Cyclin-Dependent Kinase Inhibitor Falvopiridol Administered to Patients with Advanced Gastric Carcinoma," J Clin Oncol, 19:1985-1992 (2001).

Score Search Results Details for Application 11789557 and Search Result 20091106_10462_ . . . , downloaded from URL: http://es/ScoreAccessWeb/GetItem.action?AppID=11789557swqId=09323b6780cf451a&ItemN . . . , on Nov. 24, 2009—4 pages.

Seal, et al., "Identification of a Novel Series of BET Family Bromodomain Inhibitors: Binding Mode and Profile of I-BET151 (GSK1210151A)," Bioorganic & Medicinal Chemistry Letters, 22:2968-2972 (2012).

Sedlacek, et al., "Flavoiridol (L86 8275; NSC 649890), a New Kinase Inhibitor for Tumor Therapy," International Journal of Oncology, 9:1143-1168 (1996).

Sen, et al., "Artemisinin Triggers Induction of Cell-Cycle Arrest and Apoptosis in *Leishmania donovani* Promastigotes," Journal of Medical Microbiology, 56:1231-1218 (2007).

Senderowicz, et al., "Phase I Trial of Continuous Infusion Flavopiridol, A Novel Cyclin-Dependent Kinase Inhibitor, in Patients with Refractory Neoplasms," J Clin Oncol, 16:2986-2999 (1998).

Senderowicz, et al., "Flavopiridol: The First Cyclin-Dependent Kinase Inhibitor in Human Clinical Trials," Investigational New Drugs, 17(3):313-320 (1999).

Senderowicz, et al., "Preclinical and Clinical Development of Cyclin-Dependent Kinase Modulators," Journal of the National Cancer Institute, 92(5):376-387 (2000).

Shalaby, et al., "Development of Humanized Bispecific Antibodies Reactive with Cytotoxic Lymphocytes and Tumor Cells Overexpressing the HER2 Protooncogene," J Exp Med., 175:217-225 (1992).

Shangary, et al., "Peptides Derived From BH3 Domains of Bcl-2 Family Members: A Comparative Analysis of Inhibition of Bcl-2, Bcl-$x_L$ and Bax Oligomerization, Induction of Cytochrome c Release, and Activatin of Cell Death," Biochemistry, 41:9485-9495 (2002).

Shapiro, et al., "A Phase II Trial of the Cyclin-Dependent Kinase Inhibitor Flavopiridol in Patients with Previously Untreated Stage IV Non-Small Cell Lung Cancer," Clinical Cancer Research, 7:1590-1599 (2001).

Shibue, et al., "Differential Contribution of Puma and Noxa in Dual Regulation of P53-Mediated Apoptotic Pathways," The EMBO Journal, 25(20):4952-4962 (2006).

Shimizu, et al., "Proapoptotic BH3-Only Bcl-2 Family Members Induce Cytochrome c Release, but Not Mitochondrial Membrane Potential Loss, and do Not Directly Modulate Voltage-Dependent Anion Channel Activity," PNAS, 97(2):577-582 (2000).

Shopes, "A Genetically Engineered Human IgG Mutant with Enhanced Cytolytic Activity," The Journal of Immunology, 148(9):2918-2922 (1992).

Sinicrope, et al., "Prognostic Impact of Bim, Puma and Noxa Expression in Human Colon Carcinomas," Clin Cancer Res., 14(18):5810-5818 (2008).

Sinicrope, et al., "Proapoptotic Bad and Bid Protein Expression Predict Survival in Stages II and III Colon Cancers," Clin Cancer Res., 14(13):4128-4133 (2008).

Sirois, M.G., et al., "Antisense oligonucleotide inhibition of PDGFR-b receptor subunit expression directs suppression of intimal thickening", . Circulation,; 95:669-676 (1997).

Smith, D. B., et al., "An Alvocidib-Containing Regimen is Highly Effective in AML Patients Through a Mechanism Dependent on MCL1 Expression and Function," J. Clin. Oncol, 33: abstract 7062 (2015).

(56) References Cited

OTHER PUBLICATIONS

Smith, et al., "Enhancer Biology and Enhanceropathies," Nature Stuctural & Molecular Biology, 21(3):210-219 (2014).
Smith, et al., "Real-World Outcomes Among AML Patients Treated with Decitabine or Azacitidine", Hematologica, 98(sl):19 (2013 (From the 18th Congress of the European Hematology Association, Stockholm, Sweden, Jun. 13-16, 2013, Abstract No. P047).
Soltow, et al., "Overexpression of CuZnSOD or MnSOD Protects Satellite Cells from Doxorubicin-Induced Apoptosis," The FASEB Journal, 21(5):Abstract No. A449—2 pages (2007).
Sommakia, S., et al., "Alvocidib Synergizes with BRD4 Inhibitors to Improve Cytotoxity in an AML Cell Line" Poster P255 presented at AACR-NCI-EORTC Virtual International Conference on Molecular Targets and Cancer Therapeutics, Oct. 7-10, 2021.
Song, et al., "Application of Flavopiridol, Novel Small Molecule Cyclin-Dependent Kinase Inhibitor in Tumor Therapy", National Medical Journal of China, 85(12):862-864 (2005)—With English Translation of 10 pages.
Song, et al., "Carbon Monoxide Promotes Fas/CD9-Induced Apoptosis in Jurkat Cells," The Journal of Biological Chemisry, 279(43):44327-44334 (2004).
Song, et al., "Carbon Monoxide Promotes Fas/CD9-Induced Apoptosis in Jurkat Cells," The Journal of Biological Chemisry, 279(43):44327-44334 (2004)—Additions and Correction, The Journal of Biological Chemistry, 280(23):22555-22556 (2005).
Soucek et al., "Modelling Myc inhibition as a cancer therapy," Nature 455(7213):679-683, 2008. (16 pages).
Stephens, D.M., et al., "Cyclophosphamide, Alvocidib (Flavorpiridol), and Rituximab, a Novel Feasible Chemoimmunotherapy Regimen for Patients with High-Risk Chronic Lymphocytic Leukemia", Leukemia Research, 37:1195-1199 (2013).
Stevenson, et al., "A Chimeric Antibody with Dual Fc Regions (bisFabFc) Prepared by Manipulations at the IgG Hinge," Anti-Cancer Drug Design, 3:219-230 (1989).
Stewart, et al., "The MCL-1 BH3 Helix is an Exclusive MCL-1 Inhibitor and Apoptosis Sensitizer," Nat. Chem Biol, 6(8):595-601 (2010).
Sturm, et al., "Mutation of p53 and Consecutive Selective Drug Resistance in B-CLL Occurs as a Consequence of Prior DNA-Damaging Chemotherapy," Cell Death and Differentiation, 10:477-484 (2003).
Sugiyama, et al., "Activation of Mitochondrial Voltage-Dependent Anion Channel by a Pro-Apoptotic BH3-Only Protein Bim," Oncogene, 21:4944-4956 (2002).
Suzuki, et al., "Possible Existence of Common Internalization Mechanisms Among Arginine-Rich Peptides," The Journal of Biological Chemistry, 277(4):2437-2443 (2002).
Szabo, C., "Understanding What Causes Relapse in Patients with Acute Myeloid Leukemia", Sep. 8, 2015, 3 pages. URL:https://www.pharmacytimes.com/ajax/understanding-what-cause-relpase-in-ptients-with-acute-myeloid-leukemia.
Tahir, et al., "Potential Mechanisms of Resistance to Venetoclax and Strategies to Circumvent it," BMC Cancer, 17:399—10 pages (2017).
Tan, et al., "Phase I Clinical and Pharmacokinetic Study of Falvorpiridol Administered as a Daily 1-Hour Infusion in Patients with Advanced Neoplasms", J Clin Oncol, 20:4074-4082 (2002).
Tan, et al., "The DNA Methyltransferase Inhibitor Zebularine Induces Mitochondria-Mediated Apoptosis in Gastric Cells in Vitro and in Vivo", Biochemical and Biophysical Research Communications, 430:250-255 (2013).
Tanaka, et al., "Design and Characterization of Bivalent BET Inhibitors", Nat. Chem. Biol., 12(12):1089-1096 (2016).
Taussig, et al., "Anti-CD38 Antibody-Mediated Clearance of Human Repopulating Cells Masks the Heterogeneity of Leukemia-Initiating Cells," Blood, 112:568-575 (2008).
Tefferi, A. and Vardiman, J.W., "Mechanics of Disease: Myelodysplastic Syndromes," The New England Journal of Medicine, vol. 361; 1872-1885 (2009).

Terradillos, et al., "Direct Addition of BimL to Mitochondria Does Not Lead to Cytochrome c Release," FEBS Letters, 522:29-34 (2002).
Terwijn et al., "High Prognostic Impact of Flow Cytometric Minimal Residual Disease Detection in Acute Myeloid Leukemia: Data From the HOVON/SAKK AML 42A Study," J Clin Oncol 31(31):3889-3897, 2013.
Theisen, et al., "Reversible Inhibition of Lysine Specific Demethylase 1 is a Novel Anti-Tumor Stategy for Poorly Differentiated Endometrial Carcinoma," BMC Cancer, 14:751—12 pages (2014).
Thomas, et al., "Phase I Clinical Pharmacokinetic Trial of the Cyclin-Dependent Kinase Inhibitor Flavopiridol," Cancer Chemother Pharmacol, 50:465-472 (2002).
Thomas, et al., "Phase I Clinical and Pharmacokinetic Trial Flavopiridol," Abstract #1496—Proceeding of the Annual Meeting of the American Association of Cancer Research, 38(14):222, Mar. 1997).
Thomenius, et al., "Using BH3 Profiling as a Predictive Indicator for Myeloma Patient Response to Bortezomib," Blood, 118:3592—6 pages (2011).
Thoren, "Mass Spectrometry Methods for Detecting Monoclonal Immunoglobulins in Multiple Myeloma Minimal Residual Disease," Seminars in Hematology 55(1):41-43, 2018.
Thornton, et al., "High-Dose Methylprednisolone can Induce Remissions in CLL Patients with p53 Abnormalities," Annals of Hematology, 82:759-765 (2003).
Thornton, et al., "Characterisation of TP53 Abnormalities in Chronic Lymphocytic Leukemia," The Hematology Journal, 5:47-54 (2004).
Tibes, R. and Bogenberger, J.M., "Transcriptional Silencing of MCL-1 Through Cyclin-Dependent Kinase Inhibition in Acute Myeloid Leukemia", Frontiers in Oncoogy, 9:Article 1205, 13 pages (2019).
Tolero Pharmaceuticals, "Making Meaningful Medicines," presented at the Jeffereies 2016 Healthcare Conference, New York, NY Jun. 7-10, 2016, 31 pages.
Toogood, et al., "Discovery of a Potent and Selective Inhibitor of Cyclin-Dependent Kinase 4/6," J Med. Chem, 48:2388-2406 (2005).
Touzeau, et al. "BH3-Profiling Identifies Heterogeneous Dependency of Bcl-2 Family Members in Multiple Myeloma and Predicts Sensitivity to BH3 Mimetics," Leukemia, 30(3):761-764 (2016).
Traunecker, et al, "Bispecific Single Chain Molecular (Janusins) Target Cytotoxic Lymphocytes on HIV Infected Cells," The EMBO Journal, 10(12):3655-3659 (1991).
Tsao, et al., "Concomitant Inhibitin of DNA Methyltransferase and BCL-2 Protein Function Synergistically Induce Mitochonrial Apoptosis in Acute Myelogenous Leukemia Cells," Ann Hemaltol., 91(12):1861-1870 (2012).
Tutt, et al., "Trispecific F(ab')$_3$ Derivatives that use Cooperative Signaling via the TCR/CD3 Complex and CD2 to Activate and Redirect Resting Cytotoxic T Cells," The Journal of Immunology, 147(1):60-69 (1991).
U.S. National Library of Medicine, "Flavopiridol in Treating Patients with Previously Treated Chronic Lymphocytic Leukemia or Lymphocytic Lymphoma", Apr. 9, 2003, URL=https://www.clinicaltrial.gov/ct2/show/NCT00058240?term=alvocidib&rank=16, retrieved on Dec. 11, 2018, 10 pages.
U.S. National Library of Medicine, "Flavopiridol in Treating Patients with Relapsed or Refractory Lymphoma or Multiple Myeloma", Jun. 3, 2005 URL=https://www.clinicaltrial.gov/ct2/show/NCT00112723?term=alvocidib&rank=8, retrieved on Dec. 11, 2018, 14 pages.
U.S. National Library of Medicine, "Ph I Study of Alvocidib and Cytarabine/Daunorubicin (7+3) in Patients with Newly Diagnosed Acute Myeloid Leukemia (AML)", ClinicalTrials.gov, Identifier, NCT03298984, First Posted Oct. 2, 2017, Last Update Posted Mar. 14, 2019, retrieved from https://clinicaltrials.gov/ct2/show/study/NCT03298984, 8 pages.
U.S. National Library of Medicine, "History of Changes for Study: NCT01949883 A Phase 1 Study Evaluating CPI-0610 in Patients with Progressive Lymphoma" ClinicalTrials.gov, Identifier, NCT01949883 First Posted Sep. 13, 2013, Last Update Posted Sep. 26, 2013, retrieved from https://clinicaltrials.gov/ct2/history/NCT0194883?a=2&b=2&c=merged#StudyPageTop, 7pages.

(56) References Cited

OTHER PUBLICATIONS

U.S. National Library of Medicine, "Alvocidib, Cytarabine, and Mitoxantrone in Treating Patients with Newly Diagnosed Acute Myeloid Leukemia", ClinicalTrials.gov Identifier: NCT00795002 First Posted Nov. 21, 2008, Last Update Posted Aug. 7, 2018, retrieved from https://clinicaltrials.gov/ct2/show/NCT00795002, 11 pages.
Use of a novel small molecule cyclin inhibitor flavopiridol in tumor therapy, Natl Med J China, vol. 85, No. 12, pp. 862-864 (2005).
Valencia, et al., "A New Reliable Fluorescence In Situ Hybridization Method for Identifying Multiple Specific Cytogenetic Abonormalities in Acute Myeloid Leukemia," Leukemia & Lymphoma, 51(4):680-685 (2010).
Vaquero, et al., "Extracellular Matrix Proteins Protect Pancreatic Cancer Cells from Death via Mitochondrial and Nonmitochondrial Pathways," Gastroenterology, 125:1188-1202 (2003).
Vaux, et al., "Bcl-2 Gene Promotes Haemopoietic Cell Survival and Cooperates with c-myc to Immortalize Pre-B Cells," Nature, 335:440-442 (1998).
Venkat, "Flavopiridol: A Drug that May Save Lives," CLL Topics, Archived; screenshot of webpage retrieved from Https://web.archive.org/web/20060615112217/http://clltopic.org/Chemo/Flavopirdol.htm on Aug. 16, 2016 7 pages/.
Venkatesh, S. and Lipper, R.A., "Role of the Development Scientist in Compound Lead Selection and Optimization", Journal of Pharmaceutical Sciences, 89(2):145-154 (2000).
Venugopal, et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," Clin Cancer Res, 19(15):4262-4272 (2013).
Verhoeyen, et al., "Reshaping Human Antibodies: Grafting an Antilysozyme Activity," Science, 239:1534-1536 (1988).
Ververis, et al., Histone Deacetylase Inhibitors (HDACIs): Multitargeted Anticancer Agents, Biologics: Targets and Therapy, 7:47-60 (2013).
Villela, L. and Bolanos-Mead, J., "Acute Myeloid Leukaemia Optimal Management and Recent Developments", Drugs, 71(12):1537-1550 (2011).
Vitetta, et al., "Redesigning Nature's Poisons to Create Anti-Tumor Reagents," Science, 238:1098-1104 (1987).
Vivès, et al. "A Truncated HIV-1 Tat Protein Basic Domain Rapidly Translocates Through the Plasma Membrane and Accumulates in the Cell Nucleus," The Journal of Biological Chemistry, 272(25):16010-16017 (1997).
Vo, et al., "Mitochondrial Priming Determines Chemotherapeutic Response in Acute Myeloid Leukemia," Dissertation, The Division of Medical Sciences, Harvard University, Cambridge, Massachusetts. 119 pages, Apr. 2012.
Vo, et al., "Relative Mitochondrial Priming of Myeloblasts and Normal HSCs Determines Chemotherapeutic Success in AML," Cell, 151:344-355 (2012).
Vogelzang, N.J., et al., "Phase I, first-in-human, dose-expansion study of oral TP-1287, a cyclin-dependent kinase 9 (CDK9) inhibitor, in patients with advanced solid tumors (ASTs)", Poster presented at the annual meeting of the American Association for Cancer Research, New Orleans, Louisiana, Apr. 8-13, 2022.
Wagner, A.J., et al., "Phase 1, first-in-human, dose-expansion study of oral TP-1287, a cyclin-dependent kinase 9 (CDK9) inhibitor, in patients with sarcoma", Poster presented at the American Association for Cancer Research (AACR): Special Conference on Sarcomas; May 9-12, 2022; Montreal, Quebec, Canada.
Waldschmidt et al., "Comprehensive Characterization of Circulating and Bone Marrow-Derived Multiple Myeloma Cells at Minimal Residual Disease," Seminars in Hematology 55(1):33-37, 2018.
Wang, et al., "BID: A Novel BH3 Domain-Only Death Agonist," Genes & Development, 10:2859-2869 (1996).
Wang, et al., "Cell Permeable Bcl-2 Binding Peptides: A Chemical Approach to Apoptosis Induction in Tumor Cells," Cancer Res. 60:1498-1502 (2000).
Wang, et al., "Structure-Based Discovery of an Organic Compound that Binds Bcl-2 Protein and Induces Apoptosis of Tumor Cells," PNAS, 97(13):7124-7129 (2000).
Wang, "The Expanding Role of Mitochondria in Apoptosis," Genes & Development, 15:2922-2933 (2001).
Wang, et al., "Synthesis of Pochoxime Prodrugs as Potent HSP90 Inhibitors", Bioorganic & Medicinal Chemistry Letters, 19:3836-3840 (2009).
Wei G. L., et al., "Temporally and spatially coordinated expression of cell cycle regulatory factors after angioplasty", Circ. Res., 80:418-426 (1997).
Wei, et al., "tBID, a Membrane-Targeted Death Ligand, Oligomerizes BAK to Release Cytochrome c," Genes & Development, 14:2060-2071 (2000).
Wei, et al., "Proapoptotic BAX and BAK: A Requisite Gateway to Mitochondrial Dysfunction and Death," Science, 292:727-730 (2001).
Weinstein, "Addiction to Oncogenes—the Achilles Heal of Cancer," Science 297:63-64 (2002).
Weniger, et al. "Treatment-Induced Oxidative Stress and Cellular Antioxidant Capacity Determine Response to Bortezomib in Mantle Cell Lymphoma," Clinical Cancer Research, 17(15): 5101-5112 (2011).
Werner, et al., "Bcl-2 Family Member Bfl-1/A1 Sequesters Truncated Bid to Inhibit its Collaboratin with Pro-Apoptotic Bak or Bax," The Journal of Biological Chemistry, 277(25):22781-22788 (2002).
Westerhoff, et al., Magainins and the Disruption of Membrane-Linked Free-Energy Transduction, Proc. Natl. Acad. Sci. USA, 86:6597-6601 (1989).
Whatcott, et al., "Alvocidib Potentiates the Activity of Venetoclax in Preclinical Models of Acute Myeloid Leukemia", Blood, 128(22):1652 (2016).
Wilkinson, "Ultimate Abs—Immunochemical Techniques Inspire Development of New Antibody Purification Methods," The Sceintist, 14(8):25-28 (2000).
Willis, et al., "Proapoptotic Bak is Sequestered by Mcl-1 and Bcl-$x_L$, but Not Bcl-2, Until Displaced by BH3-Only Proteins," Genes & Development, 19:1294-1305 (2005).
Willis, et al., "Apoptosis Initiated When BH3 Ligands Engage Multiple Bcl-2 Homologs, Not Bax or Bak," Science, 315:856-859 (2007).
Wolff, et al., "Monoclonal Antibody Homodimers: Enhanced Antitumor Activity in Nude Mice," Cancer Research, 53:2560-2565 (1993).
Wolff, M.E., "9 Some Considerations for Prodrug Design" in Burger's Medicinal Chemistry and Drug Discovery, Fifth Edition, vol. 1: Principles and Practice, Wolff, Manfred ed. (NY:Wiley & Sons) pp. 975-977 (1997).
Wolter, et al. "Movement of Bax from the Cytosol to Mitochondria During Apoptosis," The Journal of Cell Biology, 139(5):1281-1292 (1997).
Worland, et al., "Alteration of the Phorphorylation State of $p34^{cdc2}$ Kinase by the Falvone L86-8275 in Breast Carcinoma Cells," Biochemical Pharmacology, 46(10):1831-1840 (1993).
Woyach, et al., "Targeted Therapies in CLL: Mechanisms of Resistance and Stategies for Management," Blood, 126:471-477 (2015).
Wyatt, et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design," J. Med. Chem, 51:4986-4999 (2008).
Xiang et al., "Mcl1 haploinsufficiency protects mice from Myc-induced Acute Myeloid Leukemia," J Clin Invest., 120(6):2109-2118, 2010.
Yamaguchi, et al., "Bcl-XL Protects BimEL-Induced Bax Conformational Change and Cytochrome c Release Independent of Interacting with Bax or BimEL," The Journal of Biological Chemistry, 277(44):41604-41612 (2002).
Yamauchi, "[Incorporation of Novel Agents into the Treatment for Acute Myeloid Leukemia]", Rinsho Ketsueki, 59(10):1988-1996 (2018) English Abstract Only.

(56) References Cited

OTHER PUBLICATIONS

Yanagisawa, et al., "Translating Leukemia Stem Cells into the Clinical Setting: Harmonizing the Heterogeneity", Experimental Hematology, 44(12):1130-1137 (2016).
Yancey, D., et al., "BAD Dephosphorylation and Decreased Expression of MCL-1 Induce Rapid Apoptosis in Prostate Cancer Cells", PLOS One, 8(9):e74561, 11 pages (2013).
Yang, et al. "Calculation of Protein Conformation from Circular Dichroism," Methods Enzymol, 130:208-296 (1986).
Yang, et al. "Bad, a Heterodimeric Partner for Bcl-$x_L$ and Bcl-2, Displaces Bax and Promotes Cell Death," Cell, 80:285-291 (1995).
Yang, et al. "A Novel Liposomal Formulation of Flavopiridol," International Journal of Phamaceutics, 365:170-174 (2009).
Yang, et al. "Bone Marrow Stroma-Mediated Resistance to FLT3 Inhibitors in FLT3-ITD AML is Mediated by Persistent Activation of Extracellular Regulated Kinase," British Journal of Haematology, 164:61-72 (2014).
Yasuda, et al. "BNIP3α: A Human Homolog of Mitochondrial Proapoptotic Proetin BNIP3," Cancer Research, 59:533-537 (1999).
Yeh, et al., "Up-Regulation of CDK9 Kinase Activity and Mcl-1 Stability Contributes to the Acquired Resistance to Cyclin-Dependent Kinase Inhibitors in Leukemia," Oncotarget, 6(5):2667-2679 (2014).
Yi, et al., "Inhibition of Bid-Induced Apoptosis by Bcl-2," The Journal of Biological Chemistry, 278(19):16992-16999 (2003).
Yoshimoto, et al., "FLT3-ITD Up-Regulates MCL-1 to Promote Survival of Stem Cells in Acute Myeloid Leukemia via FLT3-ITD-Specific STAT5 Activation", Blood, 114(24):5034-5043 (2009).
Yu, et al., "Catalytic Site Remodelling of the DOT1L Methyltransferase by Selective Inhibitors," Nature Communications, 3:1288—12 pages (2012).
Zeidner, et al., "Randomized Multicenter Phase II Study of Flavopiridol (Alvocidib), Cytarabine, and Mitoxantrone (FLAM) Versus Cytarabine/Daunorubicin (7+3) in Newly Diagnosed Acute Myeloid Leukemia", Haematologica, 100(9):1172-1179 (2015).
Zeidner, et al., "Randomized Phase II Trial of Timed-Sequential Therapy (TST) with Flavopirodol (Alvocidib), Ara-C and Mitoxantrone (FLAM) Versus "7+3" for Adults Ages 70 Year and Under with Newly Diagnosed Acute Myeloid Leukemia (AML)", Blood, 120(21):Abstract 47; 5 pages (2012).
Zeidener, J.F. and Karp, J.E., "Clinical Activity of Alvocidib (Flavopiridol) in Acute Myeloid Leukemia", Leukemia Research, 39:1312-1318 (2015).
Zeidner, J.F., et al., "Phase II Study Incorporating A Novel BH3-Profiling Biomarker Approach of Alvocidib Followed by Cytarabine and Mitoxantrone in Relapsed/Refractory Acute Myeloid Leukemia (AML)", Abstract PF243, 23rd European Hematology Association Congress, Stockholm Sweden Jun. 14-17, 2018-Jun. 15, 2018, EAH library, retrieved from https://library.ehaweb.org.eha.2018/stockholm/214729/joshua.f.zeidner.phase.ii.study.incorporating.a.nove.bh3-profileing.biomarker.html?f=topic=1574*media=3, 3 pages.
Zeidner, J.F., et al., "Zella201: A Biomarker-Guided Phase II Study of Alvocidib Followed by Cytarabine and Mitoxantrone in MCL-1 Dependent Relapsed/Refractory Acute Myeloid Leukemia (AML)", Blood, 132(Suppl 1):6 pages (2018)-.
Zeidner, J.F., et al., "Final Results of a Randomized Multicenter Phase II Study of Alvocidib, Cytarabine, and Mitoxantrone Versus Cytarabine and Daunorubicin (7+3) in Newly Diagnosed High-Risk Acute Myeloid Leukemia (AML)", Leukemia Research, 72:92-95 (2018).
Zeidner, J.F., et al., "Zella-101: Phase 1 Study of Alvocidib Followed by 7 + 3 Induction in Newly Diagnosed AML Patients," Poster as presented at European Hematology Association, 25th Congress held virtually Jun. 11-21, 2020, 1 page.
Zeidner, J.F., et al., "Zella 201: A Biomarker-Guided Phase II Study of Alvocidib Followed by Cytarabine and Mitoxantrone in MCL-1 Dependent Acute Myeloid Leukemia (AML): Results of Newly Diagnosed High-Risk Exploratory Arm", Blood, 136(Supplement 1):48-50 (2020).

Zeidner J et al., Zella 201: A Biomarker-Guided Phase II Study of Alvocidib Followed by Cytarabine and Mitoxantrone in MCL-1 Dependent Acute Myeloid Leukemia (AML): Results of Newly Diagnosed High-Risk Exploratory Arm . American Society of Hematology—62nd Annual Meeting. 2020.
Zeidner, J.F., et al., "Phase I Study of Alvocidib Followed by 7+3 (Cytarabine + Daunorubicin) in Newly Diagnosed Acute Myeloid Leukemia", Clin Cancer Res, 27:60-69 (2021).
Zeidner, J.F., et al., "A Prospective Biomarker Analysis of Alvocidib Followed by Cytarabine and Mitoxantrone in MCL-1-dependent Relapsed/Refractory Acute Myeloid Leukemia", Blood Cancer Journal, 11(175):5 pages (2021).
Zeng, et al., Targeting the Leukemia Microenvironment by CXCR4 Inhibition Overcomes Resistance to Kinase Inhibitors and Chemotherapy in AML, Blood, 113(24):6215-6224 (2009).
Zha, et al. "Serine Phosphorylation of Death Agonist BAD in Response to Survival Factor Results in Binding to 14-3-3 Not BCL-$X_L$," Cell, 87:619-628 (1996).
Zha, et al. "BH3 Domain of BAD is Required for Heterodimerization with BCL-$X_L$ and Proapoptotic Activity," The Journal of Biological Chemistry, 272(39):24101-24104 (1997).
Zha, et al. "Posttranslational N-Myristoylation of BID as a Molecular Switch for Targeting Mitochondria and Apoptosis," Science, 290:1761-1765 (2000).
Zhai, et al., "Clinical Pharmacology and Pharmacogenetics of Flavopirido 1-h i.v. Infusion in Patients with Refractory Neoplasms," Anti-Cancer Drugs, 14:125-135 (2003).
Zhang, et al., "Bcl-2 Family Proteins are Essential for Platelet Survival", Cell Death Differ, 14(5):943-951 (2007).
Zhao, et al., "The Making of I-BET762, a BET Bromodomain Inhibitor Now in Clinical Development," J Med Chem, 56:7498-7500 (2013).
Zhao, et al., "BCL2 Amplicon Loss and Transcriptional Remodeling Drives ABT-199 Resistance in B Cell Lymphoma Models", Cancer Cell, 35:752-766 (2019).
Zhou, et al., "Novel Mutant-Selective EGFR Kinase Inhibitors Against EGFR T790M," Nature, 462(7276):1070-1074 (2009).
Zhou, et al., "Flavopiridol Enhances ABT-1999 Sensitivity in Unfavourable-Risk Multiple Myeloma Cells in vitro and in vivo", Br. J. Cancer, 118(3):388-397 (2018).
Zhu, et al., "Development of Venetoclax for Therapy of Lymphoid Malignancies", Drug Des. Devel. Ther., 11:685-694 (2017).
Zong, et al., "BH3-Only Proteins that Bind Pro-Survival Bcl-2 Family Members Fail to Induce Apoptosis in The Absence of Bax and Bak," Genes & Development, 15:1481-1486 (2001).
Beesley, A.H. et al., "Comparative drug screening in NUT midline carcinoma," British Journal of Cancer, vol. 110; 1189-1198 (2014).
Byrn, S. et al., "Pharmaceutical Solids: A Strategic Approach to Regulatory Considerations," Pharmaceutical Research, vol. 12; No. 7; 10 pages (1995).
Caira, M.R., "Crystalline Polymorphism of Organic Compounds," Topics in Current Chemistry, vol. 198; Springer Verlag; 46 pages (1998).
Gomez, L. et al., "Sequential combination of flavopiridol and docetaxel reduces the levels of X-linked inhibitor of apoptosis and AKT proteins and stimulates apoptosis in human LNCaP prostate cancer cells," Molecular Cancer, vol. 5; No. 5; 1216-1226 (2006).
Gordon, V. et al., "CDK9 Regulated AR Promoter Selectivity and Cell Growth through Serine 81 Phosphorylation," Molecular Endocrinology, vol. 24; 2267-2280 (2010).
Hilfiker, R. et al., "Relevance of Solid-State Properties for Pharmaceutical Products," Polymorphism: In the Pharmaceutical Industry, Wiley-VCH; Chapter 1; 19 pages (2006).
Kim, W. et al., "Abstract 5133: TP-1287, an oral prodrug of the cyclin-dependent kinase-9 inhibitor alvocidib," Cancer Res, vol. 77; 13 Suppl; 2 pages; 5133 (2017).
Nathwani, S. et al., "Novel microtubule-targeting agents, pyrrolo-1,5-benzoxazepines, induce cell cycle arrest and apoptosis in prostate cancer cells," Oncology Reports, vol. 24; 1499-1507 (2010).
Quinn et al., "Targeting Mcl-1 for the therapy of cancer," Expert Opin Investig Drugs 20(10): 1397-1411, 2011. (24 pages).

(56) References Cited

OTHER PUBLICATIONS

Ranganathan, P. et al., "Preclinical activity of a novel CRM1 inhibitor in acute myeloid leukemia," Blood, vol. 120; No. 9; 1765-1773 (2012).

Zalazar, F. et al., "Abstract 2340: CPS49 and Flavopiridol: A new selective drug combination for advanced prostate cancer," Cancer Res, vol. 72; Supplement 8; 2 pages (2012).

* cited by examiner

TREATMENT OF ACUTE MYELOID LEUKEMIA (AML) WITH VENETOCLAX FAILURE

RELATED APPLICATIONS

This application is the U.S. National Stage of International Application No. PCT/US2020/023939, filed Mar. 20, 2020, which designates the U.S., published in English, which claims the benefit of U.S. Provisional Application No. 62/821,342, filed on Mar. 20, 2019, and U.S. Provisional Application No. 62/871,934, filed on Jul. 9, 2019. The entire teachings of these applications are incorporated herein by reference.

BACKGROUND

Acute myeloid leukemia (AML) is a hematological cancer that affects myeloid cells, and is the most common type of acute leukemia in adults. The American Cancer Society estimates that there will be about 21,450 new cases of AML in the United States in 2019. AML is characterized by the rapid growth of abnormal blood cells (e.g., white blood cells, red bloods, platelets) that accumulate in the bone marrow and blood, interfering with normal blood cell function and production. If left untreated, AML progresses rapidly and can cause fatality within months.

The B-cell lymphoma 2 (BCL-2) inhibitor venetoclax (ABT-199, Venclexta) is used for treating hematological cancers, including AML. Despite the success of venetoclax in cancer treatment, approximately 20-30% of patients showed no response, a low number of patients demonstrated complete remission (8-20%), and nearly 50% of patients showed disease progression after 18 months (Huber, H., et al. Oncotargets and Therapy, 2017, 10, 645-56).

Accordingly, it is of great interest and importance to develop therapies for treating AML patients who failed prior venetoclax treatment.

SUMMARY

Provided herein are various regimens for treating acute myeloid leukemia (AML) in patients who have undergone one or more prior anti-AML therapies involving venetoclax and have shown disease progression after the prior therapy(ies). The treatment regimens disclosed herein involve alvocidib, either as a monotherapy or in combination with cytarabine or a hypomethylating agent, such as decitabine or azacitidine. The treatment regimens disclosed herein do not involve combination therapy of alvocidib with venetoclax.

The alvocidib used in any of the treatment regimens disclosed herein can be a compound of Formula (I) or a pharmaceutically acceptable salt thereof. The compound of Formula (I), or a pharmaceutically acceptable salt thereof, can be administered to a subject in need of the treatment regimen via injection, for example, intravenous injection. Alternatively, the alvocidib can be a phosphate prodrug of the compound of Formula (I) having the structure of Formula (I-b), or a pharmaceutically acceptable salt thereof. The compound of Formula (I-b), or a pharmaceutically acceptable salt thereof, can be administered to a subject in need of the treatment orally.

In one aspect, the present disclosure features a method for treating AML in a subject in need thereof, comprising administering an effective amount of alvocidib to the subject in the absence of venetoclax, wherein the subject has refractory, resistant, or relapsed AML after one or more prior therapies, at least one of which comprises venetoclax (e.g., venetoclax and a hypomethylating agent (HMA)). The one or more prior therapies may further comprise one or more therapeutic agents (e.g., a hypomethylating agent such as azacitidine and/or decitabine) for AML treatment, in addition to the venetoclax. In some instances, the method comprises the alvocidib as a sole treatment agent for AML. In some instances, the method comprises administering an effective amount of alvocidib to the subject in the absence of an additional chemotherapeutic agent (e.g., an additional chemotherapeutic agent for AML). Alternatively, in some instances, the method further comprises administering cytarabine (e.g., an effective amount of cytarabine) to the subject. In some instances, the method comprises administering an effective amount of alvocidib and an effective amount of cytarabine to the subject in the absence of an additional chemotherapeutic agent (e.g., an additional chemotherapeutic agent for AML).

In some embodiments, the subject may have refractory AML, and the one or more prior therapies comprise up to 2 cycles of venetoclax treatment. In some embodiments, the subject may have relapsed AML after the one or more prior therapies. For example, the subject may have relapsed AML after a first complete remission (CR1) period of about 90 days to about 18 months.

In some embodiments, the effective amount of the alvocidib may be from about 20 mg/m$^2$ to about 100 mg/m$^2$ once per week, preferably, from about 20 mg/m$^2$ to about 80 mg/m$^2$ once per week and, more preferably, from about 25 mg/m$^2$ to about 50 mg/m$^2$ once per week. In specific examples, the effective amount of the alvocidib is about 25 mg/m$^2$ or about 50 mg/m$^2$ once per week.

In some examples, the alvocidib may be administered to the subject at a dose of from about 20 mg/m$^2$ to about 100 mg/m$^2$, preferably, from about 20 mg/m$^2$ to about 80 mg/m$^2$, more preferably, from about 25 mg/m$^2$ to about 50 mg/m$^2$, as an intravenous bolus in about 15 minutes to about an hour once every week. In some examples, the alvocidib may be administered to the subject at a dose of from about 20 mg/m$^2$ to about 100 mg/m$^2$, preferably, from about 20 mg/m$^2$ to about 80 mg/m$^2$, more preferably, from about 25 mg/m$^2$ to about 50 mg/m$^2$, as an intravenous bolus in about 15 minutes to about 45 minutes once every week. For example, the alvocidib may be administered to the subject at a dose of from about 25 mg/m$^2$ to about 50 mg/m$^2$ as intravenous bolus in about 30 minutes. In one specific example, the alvocidib may be administered to the subject at a dose of about 25 mg/m$^2$ or about 50 mg/m$^2$.

In any of the methods described herein, the alvocidib can be administered to the subject once every week for about 1-4 consecutive weeks, preferably, for about 3 consecutive weeks, followed by a drug holiday period of about 1-3 weeks, preferably, about 1 week, as a treatment cycle. Thus, a treatment cycle can be from about 14 days to about 49 days (e.g., 49 days, 42 days, 35 days, 28 days, 21 days, 14 days). In one specific example, the alvocidib is administered to the subject once every week for 3 consecutive weeks followed by a drug holiday period of 1 week as a treatment cycle. In other words, the alvocidib is administered once every week for three consecutive weeks on a 28-day treatment cycle.

In some embodiments, any of the methods described herein may comprise one or more treatment cycles (e.g., from one to eight, such as from four to eight, two to six or three to five treatment cycles). Treatment may continue indefinitely (e.g., on an established treatment cycle) if clinically indicated (e.g., until the treatment shows substantially no benefit to a subject, provided there is no evidence of toxicity, such as an NCI CTCAE Grade 4).

In some embodiments, each treatment cycle of the method described herein may comprise: (i) administering alvocidib to the subject at a dose of from about 15 mg/m$^2$ to about 40 mg/m$^2$ as an intravenous bolus in about 15 minutes to an hour, and (ii) about one week after step (i), administering alvocidib to the subject at a dose of about 40-80 mg/m$^2$ as intravenous bolus in about 15 minutes to an hour once every week for 2-4 weeks, followed by a drug holiday period of about 2-4 weeks. In one example, each treatment cycle consists of 4 weeks, and comprises: (i) administering alvocidib to the subject at a dose of about 25 mg/m$^2$ as an intravenous bolus in about 30 minutes on the first day of the first week, and (ii) administering alvocidib to the subject at a dose of about 50 mg/m$^2$ as an intravenous bolus in about 30 minutes on the first day of the second week and the first day of the third week, followed by a drug holiday period of about 1 week.

In some embodiments, administration of alvocidib is terminated in the subject who fails to achieve at least about a 20-30% reduction, preferably about a 25% reduction, in leukemia blast count.

Any of the methods described herein may further comprise (a) administering to the subject acyclovir, trimethoprim, sulfamethoxazole, or a combination thereof (e.g., an effective amount of acyclovir, trimethoprim, sulfamethoxazole, or a combination thereof); and/or (b) administering ciprofloxacin (e.g., an effective amount of ciprofloxacin) to the subject who has neutropenia. Alternatively or in addition, the subject is free of a treatment comprising a granulocyte colony stimulating factor.

In another aspect, the present disclosure features a method for treating AML in a subject in need thereof, the method comprising, in the absence of venetoclax: (i) administering to the subject an effective amount of alvocidib in a first course of treatment; (ii) administering to the subject an effective amount of cytarabine in a second course of treatment; and (iii) administering to the subject an effective amount of alvocidib in a third course of treatment. The subject may have refractory, resistant, or relapsed AML after one or more prior therapies, at least one of which comprises venetoclax. The one or more prior therapies may further comprise one or more additional anti-AML agents, for example, azacitidine, decitabine, or a combination thereof. In some embodiments, step (ii) is performed after step (i), and step (iii) is performed after step (ii). In other embodiments, step (iii) is performed after step (i), and step (ii) is performed after step (iii). In any of the methods disclosed herein, steps (i)-(iii) may be separated by one or more drug holiday periods.

In some embodiments, the effective amount of the alvocidib in the first course of treatment may differ from the effective amount of the alvocidib in the third course of treatment. For example, the effective amount of the alvocidib in the third course of treatment may be higher than that in the first course of treatment, or visa versa.

In some instances, the effective amount of the alvocidib in the first course of treatment can be from about 10 mg/m$^2$ to about 50 mg/m$^2$ per day, e.g., about 25 mg/m$^2$ per day. In some instances, the first course of treatment may consist of 1-4 days, for example, one day or two days.

In some instances, the effective amount of the cytarabine in the second course of treatment can be from about 10 mg/m$^2$ to about 100 mg/m$^2$ per day, preferably, from about 15 mg/m$^2$ to about 40 mg/m$^2$ per day. In one example, the effective amount of the cytarabine in the second course of treatment can be about 20 mg/m$^2$ per day. In some examples, the second course of treatment consists of 8-12 days, for example, about 10 days.

In some instances, the effective amount of the alvocidib in the third course of treatment may be from about 25 mg/m$^2$ to about 100 mg/m$^2$ per day, for example, about 50 mg/m$^2$ per day. In some examples, the third course of treatment may consist of 1-3 days, for example, 1 day or 2 days.

In some examples, the first course of treatment may consist of 1 day and can be followed by a first drug holiday period of 1 day, prior to the commencement of the second course of treatment. Alternatively or in addition, the second course of treatment may consist of 10 days and can be followed by a second drug holiday period of 2 days, prior to the commencement of the third course of treatment. Further, the third course of treatment may consist of 1 day and can be followed by a third drug holiday period of about 13 days.

In embodiments comprising first, second and third courses of treatment administered on a treatment cycle, each treatment cycle comprises the first course of treatment, the second course of treatment, and the third course of treatment as described herein. In some examples, each treatment cycle is repeated every 28 days.

In some examples, each treatment cycle comprises: (i) administering the alvocidib to the subject at a daily dose of from about 10 mg/m$^2$ to about 50 mg/m$^2$ as an intravenous bolus in about 15 minutes to about one hour for about 1 to about 3 days, followed by a first drug-period of about 1 to about 3 days; (ii) administering the cytarabine to the subject by subcutaneous injection at a daily dose of from about 15 mg/m$^2$ to about 40 mg/m$^2$ for 8-12 days, followed by a second drug holiday period of 1-3 days, and (iii) administering the alvocidib to the subject at a daily dose of about 25 mg/m$^2$ to about 100 mg/m$^2$ as an intravenous bolus in about 15 minutes to about one hour for about 1 to about 3 days, followed by a third drug holiday period of about 12 to about 14 days.

In specific examples, each treatment cycle may comprise: (i) administering the alvocidib to the subject at a daily dose of about 25 mg/m$^2$ as an intravenous bolus in about 30 minutes for one day in the first course of treatment, followed by a first drug-period of one day; (ii) administering the cytarabine to the subject by subcutaneous injection at a daily dose of about 20 mg/m$^2$ for 10 days in the second course of treatment, followed by a second drug holiday period of 2 days, and (iii) administering the alvocidib to the subject at a daily dose of about 50 mg/m$^2$ as intravenous bolus in about 30 minutes for 1 day in the third course of treatment, followed by a third drug holiday period of about 13 days.

In additional examples, each treatment cycle may consist of 28 days, and comprises: (i) administering the alvocidib to the subject at a daily dose of about 25 mg/m$^2$ as an intravenous bolus in about 30 minutes one Day 1, followed by a first drug holiday period on Day 2; (ii) administering the cytarabine to the subject by subcutaneous injection at a daily dose of about 20 mg/m$^2$ on Days 3-12, followed by a second drug holiday period on Days 13-14, and (iii) administering the alvocidib to the subject at a daily dose of about 50 mg/m$^2$ as intravenous bolus in about 30 minutes on Day 15, followed by a third drug holiday period on Days 16-28.

In some embodiments, the third course of treatment (step (iii)), is performed after the first course of treatment (step (i)), and the second course of treatment (step (ii)) is performed after the third course of treatment (step (iii)). Steps (i), (ii), and (iii) may be separated by one or more drug holiday periods.

In some examples, the effective amount of the alvocidib in the first course of treatment may be from about 10 mg/m$^2$ to about 50 mg/m$^2$ per day, for example, about 25 mg/m$^2$ per day. The first course of treatment may consist of about 1 to about 4 days, for example, 1 day or 2 days. Alternatively or in addition, the effective amount of the alvocidib in the third course of treatment may be from about 25 mg/m$^2$ to about 100 mg/m$^2$ per day, for example, about 50 mg/m$^2$ per day. The third course of treatment may consist of 1-3 days, for example, 1 day or 2 days. In specific examples, the first course of treatment may consist of 1 day, and the third course of treatment may consist of 2 days. Alternatively, the first course of treatment may consist of 2 days, and the third course of treatment may consist of 1 day.

In some examples, the effective amount of the cytarabine in the second course of treatment may be from about 10 mg/m$^2$ to about 100 mg/m$^2$ per day, preferably from about 15 mg/m$^2$ to about 40 mg/m$^2$ per day. In one example, the effective amount of the cytarabine in the second course of treatment may be about 20 mg/m$^2$ per day. The second course of treatment may consist of 8-12 days, for example, 10 days. In specific examples, (a) the cytarabine in the second course of treatment is 20 mg/m$^2$, administered once or twice daily for 10 days; (b) the effective amount of cytarabine in the second course of treatment is 20 mg/m$^2$ daily, divided into two doses, administered for 4 days, wherein the two doses are administered to the subject 12 hours apart; (c) the cytarabine is administered to the subject for 2 days per week; (d) the effective amount of the cytarabine in the second course of treatment is 20 mg/m$^2$ twice daily for 10 days; and/or (e) the effective amount of cytarabine in the second course of treatment is 40 mg/m$^2$ once daily or 20 mg/m$^2$ twice daily for 10 days.

In any of the methods described herein, the alvocidib in the first course of treatment, in the third course of treatment, or both, is administered by intravenous infusion. For example, the alvocidib in the first course of treatment, in the third course of treatment, or both, is administered as a 15-minute to one-hour intravenous bolus. In one specific example, the alvocidib in the first course of treatment, in the third course of treatment, or both, is administered as a 30-minute intravenous bolus.

Alternatively or in addition, the cytarabine in the second course of treatment is administered by injection. The cytarabine in the second course of treatment may be administered by subcutaneous injection.

The methods described herein may further comprise (a) administering to the subject an intravenous hydration fluid, allopurinol, a phosphate binder, or a combination thereof (e.g., an effective amount of an intravenous hydration fluid, allopurinol, a phosphate binder, or a combination thereof) at least prior to the first dose of the alvocidib; and/or (b) administering to the subject an antibiotic, an anti-viral agent, an anti-fungal agent, or a combination thereof (e.g., an effective amount of an antibiotic, an anti-viral agent, an anti-fungal agent, or a combination thereof).

In another aspect, the present disclosure provides a method for treating refractory, resistant or relapsed AML, in a subject in need thereof, comprising administering to the subject an effective amount of alvocidib in the absence of an additional chemotherapeutic agent (e.g., an additional chemotherapeutic agent for AML), wherein the subject has refractory, resistant or relapsed AML after an induction therapy comprising venetoclax (e.g., venetoclax and a HMA). In some embodiments, from about 15 mg/m$^2$ to about 40 mg/m$^2$ (e.g., 25 mg/m$^2$) of the alvocidib is administered by intravenous bolus (e.g., of from about 30 minutes to about 60 minutes) on day 1 of a 28-day treatment cycle, and from about 40 mg/m$^2$ to about 80 mg/m$^2$ (e.g., 50 mg/m$^2$) of the alvocidib is administered by intravenous bolus (e.g., of from about 30 minutes to about 60 minutes) on days 8 and 15 of the 28-day treatment cycle.

In another aspect, the present disclosure provides a method for treating refractory, resistant or relapsed AML in a subject in need thereof, comprising administering to the subject an effective amount of a chemotherapy for AML consisting essentially of (e.g., consisting of) alvocidib, wherein the subject has refractory, resistant or relapsed AML after an induction therapy comprising venetoclax (e.g., venetoclax and a HMA). In some embodiments, from about 15 mg/m$^2$ to about 40 mg/m$^2$ (e.g., 25 mg/m$^2$) of the alvocidib is administered by intravenous bolus (e.g., of from about 30 minutes to about 60 minutes) on day 1 of a 28-day treatment cycle, and from about 40 mg/m$^2$ to about 80 mg/m$^2$ (e.g., 50 mg/m$^2$) of the alvocidib is administered by intravenous bolus (e.g., of from about 30 minutes to about 60 minutes) on days 8 and 15 of the 28-day treatment cycle.

Another aspect of the present disclosure provides a method for treating refractory, resistant or relapsed AML in a subject in need thereof, comprising administering to the subject an effective amount of alvocidib and cytarabine in the absence of an additional chemotherapeutic agent (e.g., an additional chemotherapeutic agent for AML), wherein the subject has refractory, resistant or relapsed AML after an induction therapy comprising venetoclax (e.g., venetoclax and a HMA). In some embodiments, from about 15 mg/m$^2$ to about 40 mg/m$^2$ (e.g., 25 mg/m$^2$) of the alvocidib is administered by intravenous bolus (e.g., of from about 30 minutes to about 60 minutes) on day 1 of a 28-day treatment cycle, and from about 40 mg/m$^2$ to about 80 mg/m$^2$ (e.g., 50 mg/m$^2$) of the alvocidib is administered by intravenous bolus (e.g., of from about 30 minutes to about 60 minutes) on day 15 of the 28-day treatment cycle. In some embodiments, the from about 10 mg/m$^2$ to about 100 mg/m$^2$ (e.g., about 20 mg/m$^2$) cytarabine is administered per day by injection (e.g., subcutaneous injection) on days 3, 4, 5, 6, 7, 8, 9, 10, 11 and 12 of a 28-day treatment cycle.

Another aspect of the present disclosure provides a method for treating refractory, resistant or relapsed AML in a subject in need thereof, comprising administering to the subject an effective amount of a chemotherapy for AML consisting essentially of (e.g., consisting of) alvocidib and cytarabine, wherein the subject has refractory, resistant or relapsed AML after an induction therapy comprising venetoclax (e.g., venetoclax and a HMA). In some embodiments, from about 15 mg/m$^2$ to about 40 mg/m$^2$ (e.g., 25 mg/m$^2$) of the alvocidib is administered by intravenous bolus (e.g., of from about 30 minutes to about 60 minutes) on day 1 of a 28-day treatment cycle, and from about 40 mg/m$^2$ to about 80 mg/m$^2$ (e.g., 50 mg/m$^2$) of the alvocidib is administered by intravenous bolus (e.g., of from about 30 minutes to about 60 minutes) on day 15 of the 28-day treatment cycle. In some embodiments, the from about 10 mg/m$^2$ to about 100 mg/m$^2$ (e.g., about 20 mg/m$^2$) cytarabine is administered per day by injection (e.g., subcutaneous injection) on days 3, 4, 5, 6, 7, 8, 9, 10, 11 and 12 of a 28-day treatment cycle.

In yet another aspect, the present disclosure features a method for treating AML in a subject in need thereof, the method comprising, in the absence of venetoclax: (i) administering to the subject an effective amount of decitabine or azacitidine in a first course of treatment; and (ii) administering to the subject an effective amount of alvocidib in a second course of treatment. The subject may have refractory, resistant, or relapsed AML after one or more prior therapies, at least one of which comprises venetoclax. The one or more prior therapies may further comprise one or more additional anti-AML agents, for example, azacitibine, decitabine, or a combination thereof.

In some embodiments, the effective amount of the alvocidib can be from about 20 mg/m² to about 150 mg/m² once per day, preferably, from about 20 mg/m² to about 100 mg/m² once per day. In some examples, the alvocidib can be administered to the subject as a 15-minute to one-hour intravenous bolus, preferably, an about 30-minute intravenous bolus. Alternatively, a portion of the alvocidib can be administered to the subject as a 15-minute to one-hour intravenous bolus, preferably, an about 30-minute intravenous bolus, and the remaining alvocidib can be administered to the subject by intravenous infusion in about 3 to about 6 hours, preferably, about 4 hours.

Alternatively or in addition, the effective amount of the decitabine is from about 15 mg/m² to about 40 mg/m², preferably, about 20 mg/m² once every day. In some examples, the decitabine is administered to the subject by intravenous infusion, optionally, in about 30 minutes to about 2 hours, preferably, in about 1 hour.

In some examples, the effective amount of azacitidine is from about 50 m/m² to about 100 mg/m², preferably, about 75 mg/m² once every day. The azacitidine may be administered to the subject by intravenous injection or subcutaneous injection.

In specific examples, the method may comprise one or more treatment cycles, each treatment cycle comprising: (i) administering to the subject (a) the decitabine at from about 15 mg/m² to about 40 mg/m², preferably, about 20 mg/m² once every day for 3-10 days, preferably, for 5 days, or (b) the azacitidine at from about 50 mg/m² to about 100 mg/m², preferably, 75 mg/m² once every day for 3-10 days, preferably, for 5 days; followed by a drug holiday period of about 1 to about 4 days, preferably, about 2 days; and (ii) administering to the subject the alvocidib at a dose of from about 20 mg/m² to about 100 mg/m², preferably, from about 20 mg/m² to about 90 mg/m², once per day for 1-3 days, preferably, 1 day.

For example, each treatment cycle may consist of 28 days, and comprise: (i) administering to the subject the decitabine at about 20 mg/m² once every day on Days 1-5; followed by a first drug holiday period on Days 6 and 7; and (ii) administering to the subject the alvocidib at a dose of from about 20 mg/m² to about 100 mg/m² on Day 8; followed by a second drug holiday period on Days 9-28.

In another example, each treatment cycle consists of 28 days, and comprises: (i) administering to the subject the azacitidine at about 75 mg/m² once every day on Days 1-5; followed by a first drug holiday period on Days 6 and 7; and (ii) administering to the subject the alvocidib at a dose of from about 20 mg/m² to about 100 mg/m² on Day 8; followed by a second drug holiday period on Days 9-28.

Also provided herein are the following exemplary methods:
- (i) A method for inhibiting development of tumor lysis syndrome (TLS) in a subject (e.g., patient having a hematological cancer), the method comprising administering to the subject alvocidib (e.g., at a first dose of less than or equal to about 50 mg/m², from about 15 mg/m² to about 40 mg/m² or about 25 mg/m²) and, optionally, cytarabine, in the absence of venetoclax, following any of the treatment regimens disclosed herein, wherein the subject has refractory, resistant, or relapsed hematological cancer after one or more prior therapies, at least one of which comprises venetoclax.
- (ii) A method of reducing the severity of TLS in a subject (e.g., hematological cancer subject being treated with alvocidib), the method comprising administering to the subject an effective amount of alvocidib (e.g., at a first dose of less than or equal to about 50 mg/m², from about 15 mg/m² to about 40 mg/m² or about 25 mg/m²) and, optionally, cytarabine, in the absence of venetoclax, following any of the treatment regimens disclosed herein, wherein the subject has refractory, resistant, or relapsed hematological cancer after one or more prior therapies, at least one of which comprises venetoclax.
- (iii) A method of treating TLS in a subject (e.g., hematological cancer subject being treated with alvocidib), the method comprising administering to the subject an effective amount of alvocidib (e.g., at a first dose of less than or equal to about 50 mg/m², from about 15 mg/m² to about 40 mg/m² or about 25 mg/m²) and, optionally, cytarabine, in the absence of venetoclax, following any of the treatment regimens disclosed herein, wherein the subject has refractory, resistant, or relapsed hematological cancer after one or more prior therapies, at least one of which comprises venetoclax.
- (iv) A method of decreasing mortality from TLS in subjects (e.g., hematological cancer subjects being treated with alvocidib), the method comprising administering to the subject an effective amount of alvocidib (e.g., at a first dose of less than or equal to about 50 mg/m², from about 15 mg/m² to about 40 mg/m² or about 25 mg/m²) and, optionally, cytarabine, in the absence of venetoclax, following any of the treatment regimens disclosed herein, wherein the subject has refractory, resistant, or relapsed hematological cancer after one or more prior therapies, at least one of which comprises venetoclax.
- (v) A method of reducing the incidence of TLS in subjects (e.g., hematological cancer subjects being treated with alvocidib), the method comprising administering to the subject an effective amount of alvocidib (e.g., at a first dose of less than or equal to about 50 mg/m², from about 15 mg/m² to about 40 mg/m² or about 25 mg/m²) and, optionally, cytarabine, in the absence of venetoclax, following any of the treatment regimens disclosed herein, wherein the subject has refractory, resistant, or relapsed hematological cancer after one or more prior therapies, at least one of which comprises venetoclax.
- (vi) A method of preventing TLS in a subject (e.g., hematological cancer subject being treated with alvocidib), the method comprising administering to the subject an effective amount of alvocidib (e.g., at a first dose of less than or equal to about 50 mg/m², from about 15 mg/m² to about 40 mg/m² or about 25 mg/m²) and, optionally, cytarabine, in the absence of venetoclax, following any of the treatment regimens disclosed herein, wherein the subject has refractory, resistant, or relapsed hematological cancer after one or more prior therapies, at least one of which comprises venetoclax.
- (vii) A method of treating a hematological cancer in a subject without high risk for developing TLS, the method comprising administering to the subject an effective amount of alvocidib (e.g., at a first dose of less than or equal to about 50 mg/m², from about 15 mg/m² to about 40 mg/m² or about 25 mg/m²) and, optionally, cytarabine, in the absence of venetoclax, following any of the treatment regimens disclosed herein, wherein the subject has refractory, resistant, or relapsed hematological cancer after one or more prior therapies, at least one of which comprises venetoclax.

In any of the above methods, the hematological cancer may be AML. The patient can be identified as at risk for developing TLS.

The instant disclosure provides further treatment regimens for treating AML with venetoclax failure. For example, provided herein is a method for treating AML in a subject in need thereof, the method comprising, in the absence of venetoclax: (i) administering to the subject an effective amount of alvocidib in a first course of treatment; (ii) administering to the subject cytarabine at a daily dose of from about 500 mg/m$^2$ to about 3 g/m$^2$ in a second course of treatment; and (iii) administering to the subject an effective amount of alvocidib in a third course of treatment. The subject may have refractory, resistant, or relapsed AML after one or more prior therapies, at least one of which comprises venetoclax; and optionally further comprises decitabine, azacitidine, or a combination thereof. In some embodiments, the effective amount of the cytarabine in the second course of treatment can be about 1 g/m$^2$ per day for about 3 to about 8 days (e.g., 5 days). Step (i) and/or step (iii) may be performed following the conditions described herein in connection with alvocidib treatment.

In another example, provided herein is a method for treating AML in a subject in need thereof, the method comprising, in the absence of venetoclax and mitoxantrone: (i) administering to the subject an effective amount of alvocidib in a first course of treatment; and (ii) administering to the subject an effective amount of cytarabine in a second course of treatment. The subject may have refractory, resistant, or relapsed AML after one or more prior therapies, at least one of which comprises venetoclax.

In some embodiments, step (i) can be performed following step (ii). The effective amount of cytarabine in the second course of treatment may be from about 10 mg/m$^2$ to about 100 mg/m$^2$ per day, preferably, from about 15 mg/m$^2$ to about 40 mg/m$^2$ per day. In one example, the effective amount of cytarabine in the second course of treatment may be about 20 mg/m$^2$ per day. The second course of treatment may consist of 8-12 days, preferably, 10 days. Alternatively or in addition, step (i) may comprise administering to the subject alvocidib at a dose of from about 25 mg/m$^2$ to about 100 mg/m$^2$ per day, preferably, about 50 mg/m$^2$ per day, for about 1-4 days. For example, the alvocidib can be administered to the subject at a dose of 50 mg/m$^2$ per day as an intravenous bolus in about 30 minutes once every day for 3 days.

In some embodiments, step (i) can be performed before step (ii). In some examples, step (i) may comprise administering the alvocidib to the subject at a daily dose of about 80-120 mg/m$^2$, preferably about 90 mg/m$^2$. For example, alvocidib can be administered to the subject once per day for three consecutive days, followed by a drug holiday period of 2 days. Alternatively or in addition, step (ii) may comprise administering to the subject cytarabine at a dose of from about 1 g/m$^2$ to about 3 g/m$^2$, preferably, 2 g/m$^2$, by intravenous injection in about 72 hours.

In any of the methods described herein, the subject may be MCL-1 dependent. A subject can be identified as MCL-1 dependent, for example, by examining a bone marrow sample of the subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

a) DETAILED DESCRIPTION

MCL-1 is a member of the antiapoptotic BCL-2 family of proteins. Cancer cells typically rely on MCL-1 or an alternative family member (e.g., BCL-2, BCL-xL, etc.) to resist the induction of apoptosis. Venetoclax is a BCL-2 inhibitor having the following structure:

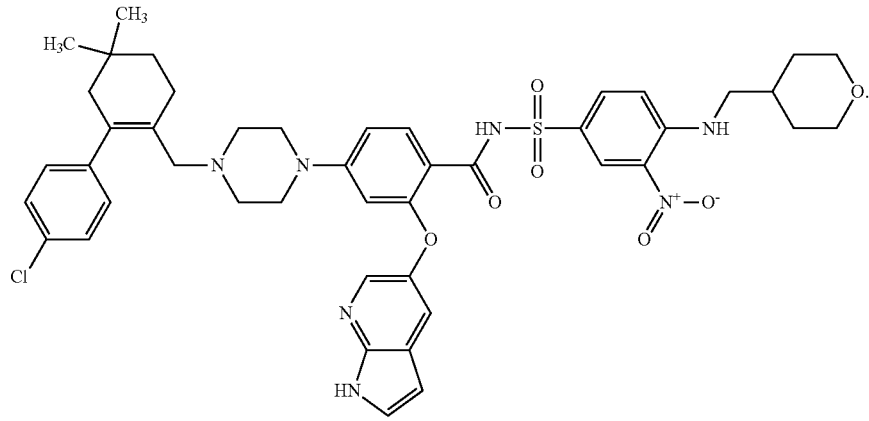 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

It is used as a frontline medication for treating AML.

It is known that cells can acquire resistance to a therapy that targets a particular BCL-2 family member by switching dependence to a different family member. For example, the BCL-2 inhibitor, venetoclax, loses activity when cancer cells switch from a BCL-2 dependency to MCL-1, leading to venetoclax failure wherein an AML patient fails in venetoclax treatment, e.g., has refractory, resistant or relapsed AML after prior therapies that include venetoclax, either as a sole agent or in combination with one or more other therapeutic agents for AML treatment, such as decitabine or azacitidine.

Both decitabine and azacitidine are hypomethylating agents (HMAs) that inhibit the activity of DNA methylation enzymes. Hypomethylating agents inhibit DNA methylation (e.g., by inhibiting the activity of a DNA methyltransferase), and can induce re-expression of the NOXA gene, which is a natural inhibitor of MCL-1. In keeping with this mechanism of action, the HMA azacitidine has been shown to reduce MCL-1 protein levels in blasts. See Konopleva and Letai, *Blood* 132(10):1007-1012. Thus, hypomethylating agents, such as azacitidine or decitabine, are often added to venetoclax to increase the therapeutic efficacy of venetoclax.

However, even combination therapies comprising venetoclax and a hypomethylating agent are associated with significant rates of failure. Alvocidib is capable of inhibiting the CDK9/MCL-1 signaling pathway and targeting the survival of MCL-1 dependent AML cells. Without wishing to be bound by any particular theory, it is believed that alvocidib, a MCL-1 inhibitor, could overcome failure associated with combination therapies comprising venetoclax and a hypomethylating agent, even when inhibition of MCL-1 (e.g., mediated by the HMA) is already included in a prior therapy. The treatment regimens disclosed herein, involving specific dosages of alvocidib and dosing schedules, either as a monotherapy or in combination with the other therapeutic agents disclosed herein (e.g., cytarabine), are expected to not only target venetoclax-resistant AML cells, but also reduce the risk of (e.g., prevent) occurrence of tumor lysis syndrome (TLS), and thus reduce mortality caused by TLS in AML patients.

Accordingly, provided herein are methods for treating AML in a subject, whose disease progressed after treatment with a BCL-2 inhibitor (e.g., venetoclax), as well as associated compositions, treatment regimens, and kits. The treatment methods disclosed herein target AML patients who have undergone one or more prior anti-AML therapies, at least one of which involves venetoclax, and are not responsive to the prior treatments, developed refractory AML after the treatment, or have the disease relapse after the treatment. In some instances, the methods described herein do not involve combination therapy of alvocidib with venetoclax.
Drug Substances and Pharmaceutical Compositions Comprising Such The methods for treating AML with venetoclax failure include the use of alvocidib, either alone or in combination with another therapeutic agent except venetoclax (e.g., cytarabine or a hypomethylating agent (HMA), such as decitabine or azacytidine). All of the therapeutic agents, as well as pharmaceutical compositions comprising such, are within the scope of the present disclosure.

(i) Therapeutic Agents

Used herein, "chemotherapeutic agent" and "chemotherapy" refer to agents and therapies, respectively, that inhibit (e.g., arrest) the growth of cancer cells as, for example, by killing the cells or inhibiting cell division. "Chemotherapeutic agent for AML" and "chemotherapy for AML" refer to chemotherapeutic agents and chemotherapies, respectively, administered to a subject with the purpose of treating AML in the subject. It will be appreciated that "chemotherapeutic agent," "chemotherapy," "chemotherapeutic agent for AML" and "chemotherapy for AML" do not include agents or therapies given primarily for supportive care. Representative examples of chemotherapeutic agents for AML include alvocidib, cytarabine, mitoxantrone, daunorubicin, venetoclax, azacitine and decitabine.

"Supportive care," as used herein, refers to treatment (e.g., therapeutic agents, therapies) given to treat or prevent symptoms of a disease and/or side effects caused by treatment of a disease (e.g., tumor lysis syndrome for AML). Examples of supportive care include hydration (e.g., IV hydration), allopurinol, phosphate binder, sodium polystyrene sulfonate, dialysis, insulin, dextrose, calcium supplementation, steroid therapy (e.g., dexamethasone), anti-diarrheal therapy (e.g., loperamide), antiemetics (e.g., 5-hydroxytryptamine receptor inhibitors), antibiotics (e.g., levofloxacin, valacyclovir), azole antifungals (e.g., fluconazole, posaconazole, voriconazole, isavuconazole) and growth factor support.

Alvocidib is an inhibitor of the CDK9-mediated expression of MCL-1. As used herein, alvocidib refers to a compound of Formula (I):

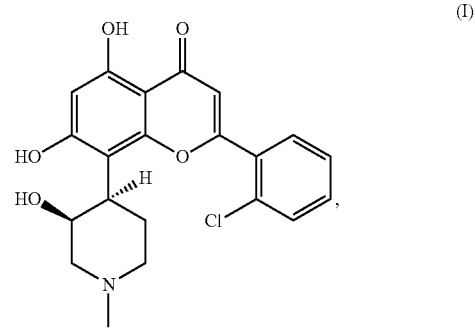 [SMILES: CN1CC[C@H](c2c(O)cc(O)c3c(=O)cc(-c4ccccc4Cl)oc23)[C@H](O)C1]

(I)

or a prodrug or a pharmaceutically acceptable salt thereof. In certain embodiments, the alvocidib is the compound of Formula (I), or a pharmaceutically acceptable salt thereof (e.g., the hydrochloride salt thereof). The compound of Formula (I) can also be referred to as 2-(2-chlorophenyl)-5,7-dihydroxy-8-[(3 S,4R)-3-hydroxy-1-methylpiperidin-4-yl]chromen-4-one. Unless indicated otherwise, when a dose or effective amount of alvocidib is quantified herein, the dose or effective amount quantified refers to the dose or effective amount of alvocidib if given as the free base of the compound of Formula (I).

In certain embodiments, the alvocidib may be a prodrug of the compound of Formula (I), or a pharmaceutically acceptable salt thereof. Even if not specifically described in each instance, all embodiments which include alvocidib optionally comprise use of a prodrug of the compound of Formula (I), or a pharmaceutically acceptable salt thereof, instead of, or in addition to (typically, instead of), the compound of Formula (I), or a pharmaceutically acceptable salt thereof. Such prodrugs are described in International Publication Nos. WO 2016/187316 and WO 2018/094275, which are incorporated herein by reference in their entireties for their teachings regarding the same. In embodiments, the prodrug of a compound of Formula (I) is a phosphate prodrug of the compound of Formula (I). In some instances, the prodrug of the compound of Formula (I) is a compound of Formula (I-a):

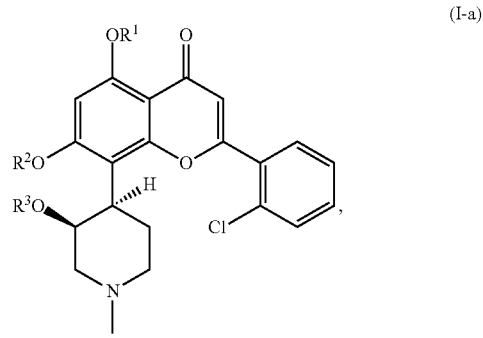

(I-a)

or a pharmaceutically acceptable salt thereof, wherein one of $R^1$, $R^2$ and $R^3$ is —P(=O)(OH)$_2$, and the other two of $R^1$, $R^2$ and $R^3$ are each —H. In some cases, the prodrug of the compound of Formula (I) is the compound of Formula (I-b):

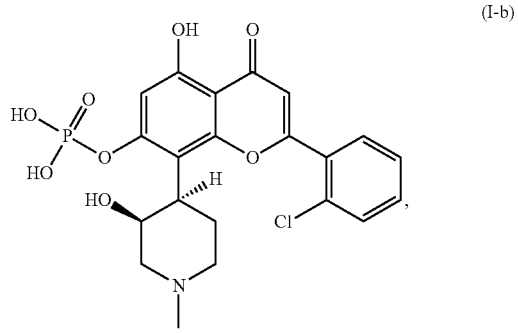 [SMILES: CN1CC[C@H](c2c(OP(=O)(O)O)cc(O)c3c(=O)cc(-c4ccccc4Cl)oc23)[C@H](O)C1]

(I-b)

or a pharmaceutically acceptable salt thereof. The compounds of Formulas (I-a) and (I-b), and their pharmaceutically acceptable salts, are orally bioavailable. Thus, the compounds of Structural Formulas I-a and I-b, or a pharmaceutically acceptable salt of the foregoing, can be administered orally, and compositions comprising a compound of Structural Formula I-a or I-b, or a pharmaceutically acceptable salt thereof, can be formulated for oral administration.

In some embodiments, therefore, the prodrug of alvocidib (e.g., a compound of Structural Formula I-a or I-b), or a pharmaceutically acceptable salt thereof, is administered to the subject orally, for example, in an amount of from about 0.5 mg to about 5 mg per day. In some embodiments, about 1 mg or about 2 mg of a prodrug of alvocidib (e.g., a compound of Structural Formula I-a or I-b), or a pharmaceutically acceptable salt thereof, is administered to a subject twice a day, or about 1 mg or about 2 mg of a prodrug of alvocidib (e.g., a compound of Structural Formula I-a or I-b), or a pharmaceutically acceptable salt thereof, is administered to a subject once a day. An effective amount of a prodrug of alvocidib can be administered to a subject for one day, two days, three days, four days, five days, six days, seven days, two weeks, three weeks, four weeks, two months, three months, four months, five months, six months, one year, two years, etc.

Cytarabine is an anti-metabolic agent that interferes with DNA synthesis. Cytarabine as used herein, refers to a compound of Formula (II):

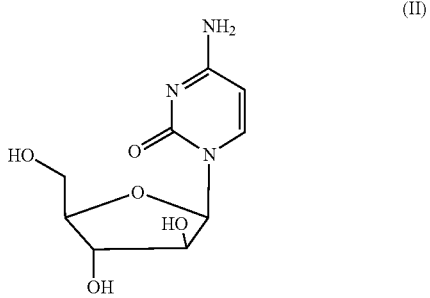

(II)

a prodrug thereof, a pharmaceutically acceptable salt thereof, or a stereoisomer thereof. In some embodiments, cytarabine is the active agent used in therapeutic applications, as known in the art. In some embodiments, the cytarabine is a compound of Formula (II), or a pharmaceutically acceptable salt thereof, (e.g., the compound of Formula (II)). Unless indicated otherwise, when a dose or effective amount of cytarabine is quantified herein, the dose or effective amount quantified refers to the dose or effective amount of cytarabine if given as the free base of the compound of Formula (II).

As used herein, decitabine refers to a compound of Formula (III):

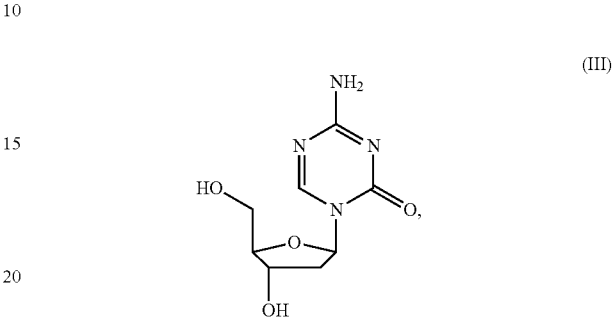

(III)

a prodrug thereof, a pharmaceutically acceptable salt thereof, or a stereoisomer thereof. In some embodiments, decitabine is the active agent used in therapeutic applications, as known in the art. In some embodiments, the decitabine is a compound of Formula (III), or a pharmaceutically acceptable salt thereof (e.g., the compound of Formula (III)).

As used herein, azacitidine refers to a compound of Formula (IV):

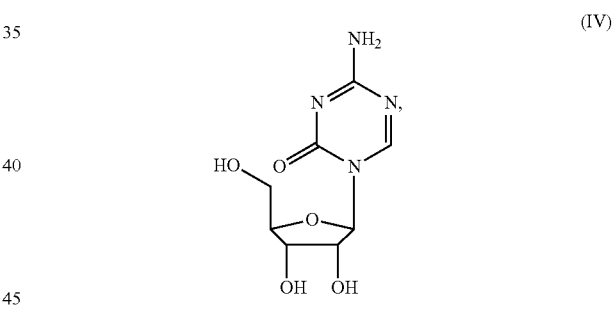

(IV)

or a prodrug thereof, a pharmaceutically acceptable salt thereof, or a stereoisomer thereof. In some embodiments, azacitidine is the active agent used in therapeutic applications, as known in the art. In some embodiments, the azacitidine is a compound of Formula (IV), or a pharmaceutically acceptable salt thereof (e.g., the compound of Formula (IV)).

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a compound is described herein as being "substantially free" of another compound(s) (e.g., enantiomer, another diastereomer(s)), the compound contains less than 10%, preferably less than 5%, more preferably less than 3%, most preferably less than 1% by weight of the other compound(s).

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

It should be understood that the compounds described herein may also be provided as homologs, analogs, derivatives, enantiomers, diastereomers, tautomers, cis- and trans-isomers, and functionally equivalent compositions of compounds described herein. "Functionally equivalent" generally refers to a composition capable of treatment of patients having cancer, or of patients susceptible to cancers.

As used herein, the term "prodrug" may refer to a derivative of a compound, which has cleavable group(s) and becomes, by solvolysis or under physiological conditions, pharmaceutically active in vivo. Such examples include, but are not limited to, ester derivatives and the like. Other derivatives of the compounds described herein have activity in both their acid and acid derivative forms, but in the acid sensitive form often offer advantages of solubility, tissue compatibility, and/or delayed release in the mammalian organism (see, Bundgard, H., *Design of Prodrugs*, pp. 7-9, 21-24, Elsevier, Amsterdam 1985). Prodrugs include acid derivatives well known to those skilled in the art, such as esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of the invention are exemplary prodrugs. In certain embodiments, the prodrug is an ester type prodrug. In certain embodiments, the prodrug is an ester type prodrug including one cleavable ester group. In certain embodiments, the prodrug is an ester type prodrug including two cleavable ester groups. In certain embodiments, the prodrug is a double ester type prodrug, such as an (acyloxy)alkyl ester or ((alkoxycarbonyl)oxy)alkyl ester. In certain embodiments, the prodrug is a phosphate, $C_{1-8}$ alkyl ester, $C_{2-8}$ alkenyl ester, $C_{2-8}$ alkynyl ester, aryl ester, $C_{7-12}$ substituted aryl ester, or $C_{7-12}$ arylalkyl ester of a compound described herein.

As used herein, the term "pharmaceutically acceptable salt" refers to those salts that are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences* (1977) 66:1-19. Pharmaceutically acceptable salts of the compounds described herein include those derived from suitable inorganic and organic acids and bases.

Examples of pharmaceutically acceptable salts derived from appropriate acids are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid, or by using other methods used in the art, such as ion exchange. Other pharmaceutically acceptable salts derived from appropriate acids include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

(ii) Pharmaceutical Compositions

Any of the therapeutic agents described herein, including alvocidib, cytarabine, decitabine, and azacitidine, may be mixed with one or more pharmaceutically acceptable excipients and/or carriers to form pharmaceutical compositions. As used herein, the term "pharmaceutically acceptable excipient" or "pharmaceutically acceptable carrier" means a non-toxic, inert solid, semi-solid or liquid filler, diluent, encapsulating material or formulation auxiliary of any type. Some examples of materials which can serve as pharmaceutically acceptable excipients are sugars such as lactose, glucose, and sucrose; starches such as corn starch and potato starch; cellulose and its derivatives such as sodium carboxymethyl cellulose, methylcellulose, hydroxypropylmethylcellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen free water; isotonic saline; citric acid; acetate salts; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants. The pharmaceutical compositions of this invention can be administered to humans and/or to animals, orally, rectally, parenterally (e.g., by injection, such as subcutaneous injection; intravenously, such as be intravenous bolus), intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, ethanol, U.S.P., and isotonic sodium chloride solution. In addition, sterile, fixed oils are conventionally employed as a solvent or suspending medium. For this purpose any bland fixed oil can be employed including synthetic mono or diglycerides. In addition, fatty acids such as oleic acid are used in the preparation of injectables.

The injectable formulations can be sterilized, for example, by filtration through a bacteria retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the therapeutic agents described herein with suitable non-irritating excipients or carriers such as cocoa butter, polyethylene glycol, or a suppository wax which are solid at ambient temperature but liquid at body temperature and, therefore, melt in the rectum or vaginal cavity and release the compound.

Solid dosage forms for oral administration include capsules, tablets, pills, powders, and granules. In such solid dosage forms, the particles are mixed with at least one inert, pharmaceutically acceptable excipient or carrier, such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers, as may be required. Ophthalmic formulation, ear drops, and eye drops are also contemplated as being within the scope of this invention.

The ointments, pastes, creams, and gels may contain, in addition to the therapeutic agents described herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the therapeutic agents described herein, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a therapeutic agent to the body. Such dosage forms can be made by dissolving or dispensing a therapeutic agent(s) in a proper medium. Absorption enhancers can also be used to increase the flux of the agent(s) across the skin. The rate can be controlled by either providing a rate controlling membrane or by dispersing the agent(s) in a polymer matrix or gel.

The pharmaceutical compositions described herein may comprise only one therapeutic agent as described herein, for example, one of alvocidib, cytarabine, decitabine, and azacitidine. Alternatively, two or more of the therapeutic agents may be formulated in one pharmaceutically acceptable composition, e.g., if they are to be co-used in any of the treatment methods described herein.

AML Subjects

The subject to be treated by any of the treatment methods described herein has undergone one or more prior therapies involving venetoclax, either as a sole therapeutic agent, or in combination with one or more other anti-AML agents (e.g., a HMA). Such a subject is either not responsive to the venetoclax treatment (resistant to veneclax), or developed refractory or relapsed AML after a treatment including venetoclax, either alone or in combination with one or more anti-AML agents (e.g., azacitidine and/or decitabine).

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or non-human animals, for example, mammals (e.g., primates (e.g., cynomolgus monkeys, rhesus monkeys)); commercially relevant mammals, such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is fish. In preferred embodiments, the subject is a human (e.g., patient). A "patient" refers to a human subject in need of treatment of a disease.

In some embodiments, the subject of the treatment regimens described herein has disease progression after the prior therapy(ies) involving venetoclax. As used herein, the phrases "disease progression", "disease progressed", "disease is progressed" or equivalents thereof have their ordinary meaning in the art, and may refer to a disease (e.g., cancer) that has worsened or spread in the body in a clinically significant manner relative to a previous time period. A healthcare professional (e.g., physician) can readily determine whether disease progression has occurred. In some embodiments, the number of normal blood cells, size and number of leukemia cells, changes that appear in the chromosomes of the leukemia cells, and genetic abnormalities that have occurred may be used to assess disease progression.

As used herein, the term "resistant" has its ordinary meaning in the art, and may refer to AML that does not respond to treatment. AML may be resistant at the beginning of treatment or it may become resistant during treatment. For instance, the AML, may become resistant after one or more treatments (e.g., including up to two treatment cycles comprising a BCL-2 inhibitor) or after one or more treatment cycles.

As used herein, the term "refractory" with respect to a subject having AML has its ordinary meaning in the art, and may refer to a subject that has residual leukemic cells in their marrow after treatment. In some embodiments, "refractory" means a subject failed to achieve CR (e.g., CR wherein less than 5% of the cells in the bone marrow are blasts, and there is an absence of blasts with Auer rods in the bone marrow, an absence of extramedullary disease, and full hematologic recovery (e.g., absolute neutrophil count (ANC)≥1,000/µL and platelet count≥100,000/µL), and/or $CR_1$) following treatment for a disease, or achieved a CR (e.g., CR wherein less than 5% of the cells in the bone marrow are blasts, and there is an absence of blasts with Auer rods in the bone marrow, an absence of extramedullary disease, and full hematologic recovery (e.g., absolute neutrophil count (ANC)≥1,000/µL and platelet count≥100,000/µL), and/or $CR_1$) lasting less than 90 days following treatment for the disease.

As used herein, the term "relapse" or "relapsed" has its ordinary meaning in the art, and may refer to the return of AML or the signs and symptoms of AML after a period of complete remission (e.g., initial complete remission) due to treatment. In some embodiments, relapse may refer to the recurrence of disease after complete remission meeting one or more of the following criteria (i)≥5% blasts in the marrow or peripheral blood, and/or (ii) extramedullary disease, and/or disease presence determined by a physician upon clinical assessment. In some embodiments, "relapse" refers to reoccurrence of a disease following a CR (e.g., CR wherein less than 5% of the cells in the bone marrow are blasts, and there is an absence of blasts with Auer rods in the bone marrow, an absence of extramedullary disease, and full hematologic recovery (e.g., absolute neutrophil count (ANC)≥1,000/µL and platelet count≥100,000/µL), and/or $CR_1$) lasting 90 days or longer.

As used herein, the term "remission" has its ordinary meaning in the art, and may refer to a decrease in or disappearance of signs and symptoms of cancer. In partial remission, some, but not all, signs and symptoms of cancer have disappeared. In complete remission (CR), all signs and symptoms of cancer have disappeared, although cancer still may be in the body. "Complete remission," as used herein, means less than 5% of the cells in the bone marrow are blasts (leukemic cells), and includes CR, $CR_i$ and $CR_h$, as those terms are used in Example 4 herein. In some embodiments, complete remission of AML means the disease has been treated, and the following are true: (i) the complete blood count is normal; (ii) less than 5% of the cells in the bone marrow are blasts (leukemia cells); and (iii) there are no signs or symptoms of leukemia in the brain and spinal cord or elsewhere in the body. In some embodiments, complete remission of AML means less than 5% of the cells in the bone marrow are blasts, and there is an absence of blasts with Auer rods in the bone marrow, an absence of extramedullary disease, and full hematologic recovery (e.g., absolute neutrophil count (ANC)≥1,000/µL and platelet count≥100,000/µL). "$CR_i$", as used herein, means less than 5% of the cells in the bone marrow are blasts, and there is an absence of blasts with Auer rods in the bone marrow, an absence of extramedullary disease, and full hematologic recovery of one peripheral blood cell type (e.g., ANC≥1,000/µL or platelet count≥100,000/µL). "$CR_h$," as used herein, means less than 5% of the cells in the bone marrow are blasts, and there is an absence of blasts with Auer rods in the bone marrow, an absence of extramedullary disease, and partial hematologic recovery of both peripheral blood cell types (e.g., ANC≥500/4, and platelet count≥50,000/µL). "Partial remission," as used herein, means greater than or equal to 5% to less than or equal to 25% of the cells in the bone marrow are blasts, and a decrease of at least 50% in the percentage of blasts. In some embodiments, partial remission of AML means (i) greater than or equal to 5% to less than or equal to 25% of the cells in the bone marrow are blasts; (ii) a decrease of at least 50% in the percentage of blasts; and (iii) the complete blood count is normal. In some embodiments, CR, $CR_i$ and $CR_h$ are as described in Example 4 herein.

In some embodiments, the subject may be resistant to venetoclax (e.g., venetoclax and a HMA), refractory, and/or have relapsed after one or more treatments including venetoclax (e.g., venetoclax and a HMA). For instance, a subject may be resistant to venetoclax, refractory, and/or have relapsed after one or more treatments comprising no more than two treatment cycles including venetoclax (e.g., venetoclax and a HMA). In some embodiments, the subject may be resistant to venetoclax (e.g., venetoclax and a HMA). For example, the subject may have primary AML (a.k.a., de novo AML) that is resistant to the BCL-2 inhibitor (e.g., venetoclax and a HMA). In some cases, the subject may have secondary AML that is resistant to venetoclax (e.g., venetoclax and a HMA). In some embodiments, the subject may have AML (e.g., primary or secondary) that is refractory after one or more treatments including venetoclax (e.g., venetoclax and a HMA). In some embodiments, the subject may have relapsed after a treatment including venetoclax (e.g., venetoclax and a HMA). For example, the subject's AML (e.g., primary AML and secondary AML) may have returned after a period of complete remission (e.g., of between about 90 days and 18 months).

In some embodiments, the subject has primary AML or secondary AML that is resistant, refractory, and/or has relapsed after a treatment including venetoclax (e.g., venetoclax and a HMA). As used herein, the term "primary," with respect to a cancer, has its ordinary meaning in the art, and may refer to the original, or first, cancer in the body. As used herein, the term "secondary," with respect to a cancer, has its ordinary meaning in the art, and may refer to a non-primary cancer. Secondary AML may arise from a previous clonal disorder of hematopoiesis, such as myelodysplastic syndrome (MDS) or chronic myeloproliferative neoplasia (cMPN), or after exposure to a leukemogenic agent (e.g., chemotherapy, radiotherapy, immunosuppressive drug, environmental leukemogenic agents).

"Induction therapy," as used herein, refers to the first therapy administered for a particular disease, such as AML. In some embodiments, the one or more prior therapies comprising venetoclax (e.g., venetoclax and a HMA) is an induction therapy.

There are other factors that can affect treatment outcomes in subjects being treated for a hematologic cancer, such as AML. For example, age, fitness for chemotherapy and MCL-1 dependence have all been linked to treatment outcomes in subjects being treated for AML.

Accordingly, in some embodiments of the methods disclosed herein, the subject is young (i.e., aged less than 60 years). In some embodiments, the subject is elderly (i.e., aged 60 years or more).

In some embodiments, the subject having resistant, refractory, and/or relapsed AML after a treatment including venetoclax, may be elderly and/or unfit.

As used herein, the term "unfit" has its ordinary meaning in the art, and may refer to having one or more physiological impairments that render a subject ineligible for a certain treatment (e.g., standard-of-care chemotherapy, intensive induction chemotherapy). Some have taken a consensus-based approach to determining fitness of a subject. See, for example, Ferrara, F., et al., *Leukemia* (2013) 27, 997-999, the relevant teachings of which are incorporated herein by reference in their entireties. In some embodiments, fitness may be determined by the consensus approach put forth in Ferrara, F., et al. In such embodiments, unfitness to intensive chemotherapy means fulfillment of at least one of nine criteria identified in Ferrara, F., et al., and unfitness to non-intensive chemotherapy means fulfillment of at least one of six criteria identified in Ferrara, F., et al. The Eastern Cooperative Oncology Group (ECOG) has put forth the ECOG Performance Status, which is a tool used to quantify the functional status of cancer patients on a scale of 0-5. In some embodiments, fitness may be determined by the ECOG Performance Status. In some embodiments, an ECOG score of greater than or equal to 2 (e.g., greater than 2, 3, greater than 3, 4, 5) renders a subject "unfit."

A "fit" subject is a subject that is not unfit.

In some embodiments, the subject is young and/or fit. In some embodiments, the subject is elderly and/or unfit.

In some embodiments, the subject has AML (e.g., resistant, relapsed, refractory), and an age of greater than 60 years (e.g., greater than 70 years, greater than 75 years). For instance, the subject may have AML (e.g., resistant, relapsed, refractory), and an age of greater than 70 years. In some instances, the subject may have AML (e.g., resistant, relapsed, refractory), an age of greater than 60 years, and an ECOG score of less than or equal to 2. In some embodiments, the subject has AML (e.g., resistant, relapsed, refractory) and is unfit. For instance, the subject may have AML and an ECOG score of greater than or equal to 2. In some embodiments, the subject has AML (e.g., resistant, relapsed, refractory), an age of greater than 60 years (e.g., greater than 70 years, greater than 75 years), and is unfit. For instance, the subject may have AML, an age of greater than 60 years, and an ECOG score of greater than or equal to 2.

In some embodiments, the subject is not undergoing treatment with a BCL-2 inhibitor. For instance, the subject may have stopped the treatment that resulted in resistance, a refractory state, and/or relapse. In such cases, the subject may have a relatively low plasma concentration of the previous anti-AML agent(s) (e.g., BCL-2 inhibitor) immediately prior to, during, and/or immediately after treatment with the methods described herein. In some embodiments, the plasma concentration of the previous anti-AML agent(s) may be about 0 ng/ml. That is, the subject may be substantially free of the previous anti-AML agent(s) (e.g., venetoclax). In general, the methods described herein may be effective in treating primary AML, secondary AML, resistant AML, refractory AML, and/or relapsed AML.

In some embodiments, the subject is MCL-1 dependent. In certain embodiments, a method may comprise treating a subject who is MCL-1 dependent.

As used herein, "MCL-1 dependent AML" refers to the subset of AML wherein myeloid cell leukemia 1 (MCL-1) is the primary driver of suppressing apoptosis. "MCL-1 dependent," with respect to a subject having AML, refers to the subset of AML subjects (e.g., patients) wherein MCL-1 is the primary driver of suppressing apoptosis of the subject's AML blasts. Typically, MCL-1 dependency promotes AML blast survival, and is associated with treatment resistance and relapse. MCL-1 dependency can be determined based on methods known in the art, such as BH3 profiling, as described in U.S. Pat. Nos. 7,868,133; 8,221,966; and 8,168,755, and U.S. Patent Appln. Publication Nos. 2011/0130309, 2016/0303101, and 2018/0172673, the relevant contents of all of which are hereby incorporated by reference in their entireties.

In some embodiments, the subject has a MCL-1 dependency percentage of greater than or equal to about 5%, greater than or equal to about 10%, greater than or equal to about 15%, greater than or equal to about 20%, greater than or equal to about 25%, greater than or equal to about 30%, greater than or equal to about 35%, or greater than or equal to about 40%. In some instances, the subject has an MCL-1 dependency percentage of less than or equal to about 80%, less than or equal to about 70%, less than or equal to about 60%, less than or equal to about 50%, less than or equal to about 40%, less than or equal to about 30%, less than or equal to about 20%, less than or equal to about 15%, or less than or equal to about 10%. All combinations of the above-referenced ranges are possible (e.g., greater than or equal to about 40% and less than or equal to about 80%).

In some embodiments, the methods described herein may further comprise identifying a subject who has an MCL-1 dependent AML. In some instances, MCL-1 dependent AML is identified by examining a bone marrow sample of the subject. Suitable methods for determining MCL-1 dependency and MCL-1 dependency percentage are described in U.S. Pat. Nos. 9,901,574, 10,132,797, and International Publication No. WO 2019/055579, the relevant disclosures of each of which are incorporated herein by reference for this particular purpose in their entireties.

Although not wishing to be bound by any particular theory, it is thought that MCL-1 dependence is found in both MRD cells and leukemia stem cells (LSCs), those cells thought to be responsible for relapse in subjects and to play a role in refractory disease. Research shows that knockout of MCL-1 in mice results in loss of early bone marrow progenitor cell populations, suggesting that MCL-1 is the primary survival signal in hematopoietic stem cells. Opferman, J. T., et al., "Obligate Role of Anti-Apoptotic MCL-1 in the Survival of Hematopoietic Stem Cells," *Science*, vol. 307, 18 Feb. 2005, the relevant contents of which are incorporated herein in their entireties. MCL-1 has also been identified as the main survival mechanism in LSCs from FLT3 positive AML. Yoshimoto, G., et al., "FLT3-ITD up-regulates MCL-1 to promote survival of stem cells in acute myeloid leukemia via FLT3-ITD-specific STAT5 activation," *Blood*, vol. 114, no. 24, 3 Dec. 2009, the relevant contents of which are incorporated herein in their entireties. It is likely that all LSCs, including non-FLT3-positive LSCs, use a similar MCL-1-dependent survival mechanism as that observed in both hematopoietic stem cells generally and FLT3-positive LSCs.

Leukemia stem cells and MRD cells are not completely synonymous with one another. However, the MRD cells that ultimately lead to relapsed disease are leukemia stem cells. See Al-Malawi, A., "Leukemic Stem Cells Shows the Way for Novel Target of Acute Myeloid Leukemia Therapy," *J. Stem Cell Res. Ther.*, vol. 3, issue 4; Yanagisawa, B., et al., "Translating leukemia stem cells into the clinical setting: Harmonizing the heterogeneity," *Experimental Hematology* 2016; 44: 1130-1137; and Gerber, J. M., et al., "A clinically relevant population of leukemic CD34+CD38− cells in acute myeloid leukemia," *Blood*, 12 Apr. 2012, vol. 119, no. 15, the relevant contents of which are incorporated herein in their entireties. Without wishing to be bound by any particular theory, it is thus thought that MCL-1 regulation may be a rational therapeutic strategy for cancer (e.g., a hematologic cancer, such as AML).

Cyclin-dependent kinases, or CDKs, are a family of proteins that form complexes involved in either cell cycle progression or transcription regulation. CDK9 is a transcription-regulating CDK that promotes the expression of MCL-1 by phosphorylating the carboxyl-terminal domain of the largest subunit of RNA polymerase II, allowing transcriptional elongation of MCL-1 mRNA. Inhibition of CDK9, as by a CDK9 inhibitor such as alvocidib, is thus thought to provide the MCL-1 regulation that, either alone as a monotherapy or in combination with one or more additional therapeutic agents, could be used to eliminate or substantially eliminate MCL-1-dependent cells, such as MRD cells and LSCs, thereby converting a subject from MRD-positive status to MRD-negative status, for example, to treat a cancer (e.g., a hematologic cancer, such as AML) and/or reduce risk of relapse in a subject having a cancer (e.g., a hematologic cancer, such as AML).

In some embodiments, the subject in need of treatment is measurable residual disease (MRD)-positive after the one or more prior therapies and prior to being administered a treatment regimen described herein (e.g., alvocidib, either alone as a monotherapy, or in combination with another therapeutic agent, for example, cytarabine or a hypomethylating agent, such as azacytidine or decitabine). In some embodiments, the subject is MRD-negative after being administered a treatment regimen described herein (e.g., alvocidib, either alone as a monotherapy, or in combination with another therapeutic agent, for example, cytarabine or a hypomethylating agent, such as azacytidine or decitabine).

In hematological cancers, such as AML, measurable residual disease, minimal residual disease and MRD refer to the post-therapy persistence of leukemic cells at levels below morphologic detection. Although not wishing to be bound by any particular theory, MRD is thought to be a strong prognostic indicator of increased risk of relapse or shorter survival in patients with hematologic cancers, such as AML. MRD testing for AML is typically conducted using one of three techniques: immunophenotypic detection by multiparameter flow cytometry (MFC), real-time quantitative PCR (RT-qPCR) and next-generation sequencing technology. MFC uses panels of fluorochrome-labeled monoclonal antibodies to identify aberrantly expressed antigens of leukemic cells. RT-qPCR can be used to amplify leukemia-associated genetic abnormalities. Next-generation sequencing technology can be used to evaluate a few genes or an entire genome. Together, RT-qPCR and next-generation sequencing technology represent molecular approaches to MRD testing. Each of the foregoing methods of detecting MRD status in a subject is described in Ravandi, F., et al., *Blood Advances* 12 Jun. 2018, vol. 2, no. 11, and Schuurhuis, G. J., et al., *Blood* 2018 Mar. 22, 131(12): 1275-1291, the relevant contents of which are incorporated herein by reference in their entireties.

To guide the development of a standardized approach to MRD testing, the European LeukemiaNet (ELN) has issued consensus recommendations for the measurement of MRD in AML. According to the ELN, a percentage of cancer (e.g., AML) cells to leukocytes of 0.1% or greater in a subject's bone marrow, measured by MFC according to the ELN's recommendations for MRD testing by MFC, indicates the subject is MRD positive (MRD+) by MFC according to the ELN's recommendations for MRD testing by MFC. A percentage of cancer cells to leukocytes of less than 0.1% in a subject's bone marrow, measured by MFC according to the ELN's recommendations for MRD testing by MFC, indicates the subject is MRD negative (MRD−) by MFC according to the ELN's recommendations for MRD testing by MFC.

The ELN has also issued guidelines for molecular MRD testing in AML. The ELN defines complete molecular remission as complete morphologic remission plus two successive negative MRD samples obtained within an interval of ≥4 weeks at a sensitivity level of at least 1 in 1,000, wherein the samples are collected and measured according to the ELN guidelines for molecular MRD testing. The ELN defines molecular persistence at low copy numbers, which is associated with a low risk of relapse, as MRD with low copy numbers (<100-200 copies/$10^4$ ABL copies corresponding to <1-2% of target to reference gene or allele burden) in patients with morphologic CR, and a copy number or relative increase<1 log between any two positive samples collected at the end of treatment, wherein the samples are collected and measured according to the ELN guidelines for molecular MRD testing. The ELN defines molecular progression in patients with molecular persistence as an increase of MRD copy numbers≥1 log 10 between any two positive samples collected and measured according to the ELN guidelines for molecular MRD testing. The ELN defines molecular relapse as an increase of the MRD level of ≥1 log 10 between two positive samples in a patient who previously tested negative, wherein the samples are collected and measured according to the ELN guidelines for molecular MRD testing. Both molecular persistence and molecular relapse are indicators of an MRD-positive subject by RT-qPCR conducted according to the ELN guidelines for MRD testing by RT-qPCR. Thus, patients in complete molecular remission and patients labelled as having molecular persistence at low copy numbers are MRD-negative by RT-qPCR conducted according to the ELN guidelines for MRD testing by RT-qPCR. RT-qPCR is the recommended molecular approach to MRD testing, as discussed in Ravandi, F., et al. and Schuurhuis, G. J., et al. Specific recommendations for collecting and measuring samples (e.g., bone marrow samples) for MRD testing are described in Ravandi, F., et al., *Blood Advances* 12 Jun. 2018, vol. 2, no. 11 and Schuurhuis, G. J., et al., *Blood* 2018 Mar. 22, 131(12): 1275-1291, the relevant contents of which are incorporated herein by reference in their entireties.

When a subject having a hematologic cancer, such as AML, is described herein as being "measurable residual disease negative," "minimal residual disease negative," "MRD-negative" or "MRD⁻" without a further modifier, such as by MFC or by RT-qPCR, the subject is MRD negative according to at least one of the ELN's criteria described herein (e.g., MFC, molecular biology). In some embodiments, the subject is MRD-negative by MFC conducted according to ELN guidelines for MRD testing. In some embodiments, the subject is MRD-negative by RT-qPCR conducted according to ELN guidelines for MRD testing. In some embodiments, the subject is MRD-negative by both MFC and RT-qPCR conducted according to ELN guidelines for MRD testing. In some embodiments, the subject is MRD-negative by MFC conducted according to ELN guidelines for MRD testing, and is MRD-positive by RT-qPCR conducted according to ELN guidelines for MRD testing. In some embodiments, the subject is MRD-positive by MFC conducted according to ELN guidelines for MRD testing, and is MRD-negative by RT-qPCR conducted according to ELN guidelines for MRD testing. When a subject is MRD-negative according to one of the ELN's criterion described herein (e.g., the criterion for MFC), but MRD-positive according to another of the ELN's criterion described herein (e.g., the criterion for RT-qPCR), that subject can still be described as MRD-negative according to the use of that term herein because the subject is MRD negative according to at least one of the ELN's criteria described herein.

When a subject having a hematological cancer, such as AML, is described herein as being "measurable residual disease positive," "minimal residual disease positive," "MRD-positive" or "MRD+," the subject is MRD positive by the ELN's criteria for MFC and RT-qPCR described herein. For example, a subject that is MRD positive for AML can be MRD-positive by MFC conducted according to ELN guidelines for MRD testing in AML, and MRD-positive by RT-qPCR conducted according to ELN guidelines for MRD testing in AML.

Thus, in some embodiments of the methods described herein, the method further comprises detecting the MRD status of a subject (e.g., after the one or more prior therapies, prior to administering a treatment regimen described herein, and/or after administering a treatment regimen described herein). In some embodiments, the method further comprises detecting the MRD status of a subject prior to and after administering a treatment regimen described herein. In some embodiments, administration of at least one agent in the treatment regimen (e.g., the alvocidib) is terminated if the subject is determined to be MRD-negative.

Methods of Treating AML with Venetoclax Failure

Provided herein are methods of treating AML subjects (e.g., patients) who failed in prior venetoclax treatment. Any AML subject (e.g., patient) described herein (e.g., in the section titled "AML Subjects") can be treated by any of the treatment regimens disclosed herein.

The term "treating," as used herein, refers to the application or administration of a composition including one or more active agents to a subject who has AML, a symptom of AML, or a predisposition toward AML, with the purpose to cure, heal, alleviate, relieve, alter, remedy, ameliorate, improve, or affect the disease, the symptoms of the disease, or the predisposition toward the disease.

Any of the therapeutic agents disclosed herein, including alvocidib, cytarabine, or a hypomethylating agent (HMA), such as decitabine and azacytidine, can be administered to an AML subject (e.g., patient) via a suitable route at a suitable dosing schedule. Exemplary treatment regimens involving the use of alvocidib for treatment of AML subjects with venetoclax failure are described below. In some embodiments, the treatment regimens disclosed herein do not involve the use of venetoclax.

(i) Treatment Regimens Involving Alvocidib Monotherapy

In some embodiments, provided herein is alvocidib monotherapy for treating AML patients who failed in prior venetoclax treatment (e.g., a patient described herein). Such a monotherapy may comprise the step(s) of administering an effective amount of alvocidib to a subject in the absence of venetoclax. Such a monotherapy may also comprise the step(s) of administering an effective amount of alvocidib to the subject in the absence of an additional chemotherapeutic agent (e.g., in the absence of an additional chemotherapeutic agent for AML, in the absence of venetoclax). The subject can be a human patient having refractory, resistant, or relapsed AML after one or more prior therapies, at least one of which comprises venetoclax (e.g., venetoclax and an HMA).

"In the absence of venetoclax," as used herein, means that the therapy does not involve combination therapy of alvocidib with venetoclax. A subject (e.g., AML patient) of the treatment regimens disclosed herein (e.g., the monotherapy) may be free of venetoclax treatment after the prior therapy(ies) involving venetoclax (either taken alone or in combination with other anti-AML therapies) terminates before commencement of the treatment regimens disclosed herein. A subject (e.g., AML patient) of the treatment regimens disclosed herein (e.g., the monotherapy) may also or alternatively be free of venetoclax treatment after the prior therapy(ies) involving venetoclax (either taken alone or in combination with other anti-AML therapies) after a suitable washout period for venetoclax before commencement of the treatment regimens disclosed herein. A typical washout period for venetoclax is greater than about 38 hours, for example, greater than about 57 hours, about 57 hours, about 72 hours or from about 90 to about 95 hours. Accordingly, in some embodiments, administration of a treatment regimen disclosed herein commences about 57 hours or more (e.g., at least 3 days, at least 4 days, at least 5 days, at least six days, at least seven days, at least eight days, etc.) after receiving the venetoclax of the prior therapy(ies). In other words, any of the treatment regimens described herein, including the monotherapy, excludes combination therapy of alvocidib with venetoclax (the administration of alvocidib is not in combination with venetoclax).

"In the absence of an additional chemotherapeutic agent," as used herein, means that the therapy does not involve combination therapy of alvocidib and an additional chemotherapeutic agent (e.g., cytarabine, azacitidine, decitabine). A subject (e.g., AML patient) of the treatment regimens disclosed herein (e.g., the monotherapy, alvocidib in combination with low-dose cytarabine) may be free of treatment with an additional chemotherapeutic agent after prior therapy(ies) involving the additional chemotherapeutic agent (either taken alone or in combination with other chemotherapies) terminates before commencement of the treatment regimen excluding additional chemotherapeutic agents. A subject (e.g., AML patient) of the treatment regimens disclosed herein (e.g., the monotherapy, alvocidib in combination with low-dose cytarabine) may also or alternatively be free of treatment with an additional chemotherapeutic agent after prior therapy(ies) involving the additional chemotherapeutic agent (either taken alone or in combination with other chemotherapies) after a suitable washout period for the additional chemotherapeutic agent before commencement of the treatment regimens disclosed herein. It will be understood that a subject (e.g., AML patient) of the monotherapy disclosed herein may be free of treatment with an additional chemotherapeutic agent but still be receiving non-chemotherapeutic agents, e.g., receiving supportive care.

The term "combination therapy" refers to the administration of two or more therapeutic agents to treat a disease, disorder or condition described herein. Such administration encompasses co-administration of the therapeutic agents in a substantially simultaneous manner, such as in a pharmaceutical combination. Alternatively, such administration encompasses co-administration in multiple containers, or separate containers (e.g., capsules, powders, and liquids) for each active ingredient, such as in a kit. Such administration also encompasses use of each type of therapeutic agent in a sequential manner, either at approximately the same time or at different times. A therapeutic agent and an additional therapeutic agent(s) can be administered via the same administration route or via different administration routes.

In combination therapies, the therapeutic agents may be manufactured and/or formulated by the same or different manufacturers. Moreover, the therapeutic agents may be brought together into a combination therapy, e.g.: (i) prior to release of the combination product to physicians (e.g., in the case of a kit or pharmaceutical combination comprising the therapeutic agents); (ii) by the physician (or under the guidance of a physician) shortly before administration; (iii) in the subjects, e.g., during sequential administration of the therapeutic agents.

In some embodiments, the method comprises administering to the subject an effective amount of a chemotherapy for AML, consisting essentially of (e.g., consisting of) alvocidib.

An AML subject (e.g., patient) with venetoclax failure may be subject to the alvocidib monotherapy described herein. In some instances, the AML subject (e.g., patient) may have been treated by venetoclax (e.g., venetoclax and a HMA) for up to two cycles and developed refractory AML. In other instances, the AML subject (e.g., patient) may show first complete remission (CR1) for a certain period (e.g., about 90 days to 18 months) after prior therapy(ies) involving venetoclax, and show disease relapse afterwards.

In some embodiments, the monotherapy may involve alvocidib as the sole anti-AML agent, which may be given to the subject at a specific dosing schedule (e.g., once every day, once every other day, or once every week) at a suitable dose(s). In some instances, the monotherapy may include one or more treatment cycles (for example, 4-8 cycles, such as 6 cycles). As used herein, the term "treatment cycle" has its ordinary meaning in the art, and may refer to one or more courses of treatments that are repeated on a regular schedule, including periods of rest. In other instances, the subject may stay on the treatment, e.g., having an indefinite number of the treatment cycles, if clinically indicated (e.g., until the treatment shows substantially no benefit to a subject, provided there is no evidence of toxicity, such as an NCI CTCAE Grade 4), which can be determined by a medical practitioner. In some instances, lack of substantial treatment benefit may be represented by disease progression when a subject is on the treatment. In other instances, lack of treatment benefit may be represented by developing side effects which outweigh therapeutic effects.

Each treatment cycle may comprise one or more administrations of alvocidib at the same or different doses and one or more drug holiday periods. As used herein, a "drug holiday period" refers to a period during which the subject is not given the anti-AML chemotherapeutic agent recited in the AML treatment regimen. In some embodiments, the subject may not be given any therapeutic agent during a drug holiday period.

To perform the monotherapy described herein, an effective amount of alvocidib can be administered to the subject by a suitable route, e.g., those described herein. The terms "administer," "administering," or "administration" in connection with any of the therapeutic agents described herein (e.g., alvocidib, cytarabine, decitabine, and azacitidine) refer to implanting, absorbing, ingesting, injecting, inhaling, or otherwise introducing the therapeutic agent(s), or a composition thereof, in, on or to a subject.

"An effective amount," as used herein, refers to the amount of each active agent described herein (e.g., alvocidib, cytarabine, decitabine, and azacitidine) required to confer therapeutic effect on the subject, either alone or in combination with one or more other active agents. Effective amounts vary, as recognized by those skilled in the art, depending on, for example, route of administration, excipient usage, and co-usage with other active agents. In the case of treating a particular disease or condition, the desired therapeutic effect is inhibiting the progression of the disease. This may involve only slowing the progression of the disease temporarily, although more preferably, it involves halting the progression of the disease permanently. This can be monitored by routine methods or can be monitored according to diagnostic methods discussed herein. The desired response to treatment of the disease or condition also can be delaying the onset or even preventing the onset of the disease or condition.

An effective amount of a particular therapeutic agent will depend, for example, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reason.

In some embodiments, the monotherapy dosage of alvocidib (e.g., a compound of Formula (I)) may be greater than or equal to about 15 mg/m$^2$, greater than or equal to about 20 mg/m$^2$, greater than or equal to about 30 mg/m$^2$, greater than or equal to about 40 mg/m$^2$, greater than or equal to about 50 mg/m$^2$, greater than or equal to about 60 mg/m$^2$, greater than or equal to about 70 mg/m$^2$, greater than or equal to about 80 mg/m$^2$, greater than or equal to about 90 mg/m$^2$, greater than or equal to about 100 mg/m$^2$, greater than or equal to about 110 mg/m$^2$, greater than or equal to about 120 mg/m$^2$, greater than or equal to about 130 mg/m$^2$, greater than or equal to about 140 mg/m$^2$, or greater than or equal to about 150 mg/m$^2$.

In some embodiments, a monotherapy dose of alvocidib (e.g., a compound of Formula (I)) may be between about 15 mg/m² and about 75 mg/m², about 15 mg/m² and about 50 mg/m², about 20 mg/m² and about 160 mg/m², between about 20 mg/m² and about 140 mg/m², between about 20 mg/m² and about 120 mg/m², between about 20 mg/m² and about 100 mg/m², between about 20 mg/m² and about 80 mg/m², between about 40 mg/m² and about 160 mg/m², between about 40 mg/m² and about 140 mg/m², between about 40 mg/m² and about 120 mg/m², between about 40 mg/m² and about 100 mg/m², between about 40 mg/m² and about 80 mg/m², between about 60 mg/m² and about 160 mg/m², between about 60 mg/m² and about 120 mg/m², between about 60 mg/m² and about 100 mg/m², or between about 60 mg/m² and about 80 mg/m².

The term "about" or "approximately" means within an acceptable error range for the particular value as determined by one of ordinary skill in the art, which will depend, in part, on how the value is measured or determined, i.e., the limitations of the measurement system. For example, "about" can mean within an acceptable standard deviation, per the practice in the art. Alternatively, "about" can mean a range of up to ±20%, preferably, up to ±10%, more preferably, up to ±5% and, more preferably still, up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In some embodiments, a suitable AML, subject (e.g., patient) may be given a suitable dose of alvocidib (e.g., those noted above) once every day for a suitable period (e.g., 2-5 days). Optionally, the patient may have a suitable drug holiday period, for example, 2-4 days (e.g., 2 days). When needed, the treatment period and drug holiday period (which, together, may constitute a treatment cycle) can be repeated multiple times, for example, 4-8 times (e.g., 6 times).

In other embodiments, a suitable AML subject (e.g., patient) may be given a suitable dose of alvocidib (e.g., from about 15 mg/m² to about 75 mg/m², from about 15 mg/m² to about 50 mg/m², from about 20 mg/m² to about 100 mg/m², from about 20 mg/m² to about 80 mg/m², from about 25 mg/m² to about 50 mg/m², about 19 mg/m², about 25 mg/m² or about 50 mg/m²) once every week for a suitable period (e.g., 2-6 weeks, such as 4 weeks). Optionally, the patient may have a suitable drug holiday period, for example, 2-4 weeks (e.g., 2 weeks). When needed, the treatment period and drug holiday period (which, together, may constitute a treatment cycle) can be repeated multiple times, for example, 4-8 times (e.g., 6 times). The treatment may terminate if no longer clinically indicated (e.g., when no substantial treatment benefit is observed, there is evidence of toxicity, such as an NCI CTCAE Grade 4).

In some embodiments, the alvocidib monotherapy may include 4-8 treatment cycles (e.g., 6 cycles), each of which may include (e.g., consist of, consist essentially of) 3-6 weeks, for example, 4 weeks. In some examples, each cycle may include (e.g., consist of, consist essentially of) 28 days (4 weeks). Each cycle may comprise (i) administration of alvocidib to a suitable AML subject (e.g., patient) at a first dose, and (ii) administration of alvocidib to the subject (e.g., patient) at a second dose about one week after (i), the second dose being given to the patient once every week for 1-4 consecutive weeks (e.g., 2 weeks); and a drug holiday period, which may consist of 1-4 weeks, for example, 1 week. In some example, the first dose is a low dose of alvocidib, which can range from about 10 mg/m² to about 50 mg/m², e.g., from about 15 mg/m² to about 40 mg/m² or from about 20 mg/m² to about 30 mg/m²). In one example, the low dose of alvocidib is about 25 mg/m². In one example, the low dose of alvocidib is about 19 mg/m². Alternatively, or in addition, the second dose of alvocidib is a high dose of alvocidib (which is higher than the first, low dose of alvocidib). A high dose of alvocidib may range from about 40 mg/m² to about 100 mg/m², for example, from about 40 mg/m² to about 80 mg/m², or from about 40 mg/m² to about 60 mg/m². In one example, the high dose is about 50 mg/m².

In general, alvocidib may be administered by any suitable method, e.g., those described herein. For example, alvocidib (e.g., a compound of Formula (I), or a pharmaceutically acceptable salt thereof) may be administered intravenously (e.g., bolus, infusion). In some embodiments, one dose of alvocidib may be administered as an intravenous bolus in about 15 minutes to about 1 hour, for example, about 30 minutes to about one hour or about 30 minutes. In other examples, a portion of one dose of alvocidib may be administered as an intravenous bolus in about 15 minutes to about 1 hour, for example, about 30 minutes to about one hour or about 30 minutes, and the remaining portion may be administered by intravenous infusion in, e.g., 4-6 hours.

In some embodiments, alvocidib monotherapy may be in combination with other therapeutic agents (which do not include venetoclax). Such additional therapeutic agents may be additional anti-cancer agents. Alternatively, the additional pharmaceutically active agents by themselves may have no anti-AML effects but enhance the anti-AML effects of alvocidib or reduce potential side effects of alvocidib. Such additional therapeutic agents include, but are not limited to, an intravenous hydration fluid, allopurinol, a phosphate binder, or a combination thereof. In certain embodiments, the method may further comprise administering an antibiotic, an anti-viral agent, an anti-fungal agent, or a combination thereof (e.g., an effective amount of an antibiotic, an anti-viral agent, an anti-fungal agent, or a combination thereof) to the subject.

(ii) Treatment Regimens Involving Alvocidib in Combination with Low Dose of Cytarabine Also provided herein are treatment regimens comprising alvocidib in combination with low dose cytarabine. Such a treatment regimen comprises one or more treatment cycles (e.g., 4-8 cycles, such as 6 cycles), each may contain 28 days.

Some embodiments provide a method for treating AML (e.g., refractory, resistant or relapsed AML) in a subject in need thereof (e.g., a subject described herein), comprising administering an effective amount of alvocidib to the subject in the absence of venetoclax and further comprising administering cytarabine (e.g., an effective amount of cytarabine) to the subject. In some embodiments, the subject has AML (e.g., refractory, resistant or relapsed AML) after one or more prior therapies, at least one of which comprises venetoclax (e.g., venetoclax and a HMA).

Some embodiments provide a method for treating AML (e.g., refractory, resistant or relapsed AML) in a subject in need thereof (e.g., a subject described herein), comprising administering an effective amount of alvocidib and (e.g., an effective amount of) cytarabine (e.g., low-dose cytarabine) to the subject in the absence of an additional chemotherapeutic agent (e.g., an additional chemotherapeutic agent for AML). In some embodiments, the subject has AML (e.g., refractory, resistant or relapsed AML) after one or more prior therapies, at least one of which comprises venetoclax (e.g., venetoclax and a HMA).

Some embodiments provide a method for treating AML (e.g., refractory, resistant or relapsed AML) in a subject in need thereof (e.g., a subject described herein), comprising administering an effective amount of a chemotherapy for AML consisting essentially of (e.g., consisting of) alvocidib and cytarabine (e.g., low dose cytarabine) to the subject. In some embodiments, the subject has AML (e.g., refractory, resistant or relapsed AML) after one or more prior therapies, at least one of which comprises venetoclax (e.g., venetoclax and a HMA).

As used herein, the term "low dose" or "low-dose" or "low dosage," with respect to cytarabine, has its ordinary meeting in the art. In some embodiments, a low dose of cytarabine may be less than or equal to about 100 mg/m$^2$, less than or equal to about 90 mg/m$^2$, less than or equal to about 80 mg/m$^2$, less than or equal to about 70 mg/m$^2$, less than or equal to about 60 mg/m$^2$, less than or equal to about 50 mg/m$^2$, less than or equal to about 40 mg/m$^2$, less than or equal to about 30 mg/m$^2$, less than or equal to about 25 mg/m$^2$, less than or equal to about 20 mg/m$^2$, or less than or equal to about 15 mg/m$^2$. In certain embodiments, a low dose of cytarabine may be between about 10 mg/m$^2$ and about 100 mg/m$^2$, between about 10 mg/m$^2$ and about 90 mg/m$^2$, between about 10 mg/m$^2$ and about 80 mg/m$^2$, between about 10 mg/m$^2$ and about 70 mg/m$^2$, between about 10 mg/m$^2$ and about 60 mg/m$^2$, between about 10 mg/m$^2$ and about 50 mg/m$^2$, between about 10 mg/m$^2$ and about 40 mg/m$^2$, between about 10 mg/m$^2$ and about 30 mg/m$^2$, between about 15 mg/m$^2$ and about 100 mg/m$^2$, between about 15 mg/m$^2$ and about 90 mg/m$^2$, between about 15 mg/m$^2$ and about 80 mg/m$^2$, between about 15 mg/m$^2$ and about 70 mg/m$^2$, between about 15 mg/m$^2$ and about 60 mg/m$^2$, between about 15 mg/m$^2$ and about 50 mg/m$^2$, between about 15 mg/m$^2$ and about 40 mg/m$^2$, or between about 15 mg/m$^2$ and about 20 mg/m$^2$. In some embodiments, the low dose of cytarabine is between about 10 mg/m$^2$ and about 100 mg/m$^2$ (e.g., between about 15 mg/m$^2$ and about 40 mg/m$^2$). In some embodiments, the low dose of cytarabine is about 20 mg/m$^2$.

In some embodiments, each treatment cycle comprises a first course of treatment involving a low dose of alvocidib, a second course of treatment involving a low dose of cytarabine, and a third course of treatment involving a high dose of alvocidib. The first to three courses of treatment can be performed in any order. In one example, each cycle comprises the order of low dose alvocidib (first course)-cytarabine (second course)-high dose alvocidib (third course). In other examples, each cycle comprises the order of low dose alvocidib (first course)-high dose alvocidib (third course)-cytarabine (second course), or high dose alvocidib (third course)-cytarabine (second course)-low dose alvocidib (first course).

In some examples, a low dose of alvocidib may range from about 10 mg/m$^2$ to about 50 mg/m$^2$, e.g., from about 15 mg/m$^2$ to about 40 mg/m$^2$ or from about 20 mg/m$^2$ to about 30 mg/m$^2$). In one example, the low dose of alvocidib is about 25 mg/m$^2$. In one example, the low dose of alvocidib is about 19 mg/m$^2$. Alternatively or in addition, a high dose of alvocidib may range from about 40 mg/m$^2$ to about 100 mg/m$^2$, for example, from about 40 mg/m$^2$ to about 80 mg/m$^2$, or from about 40 mg/m$^2$ to about 60 mg/m$^2$. In one example, the high dose is about 50 mg/m$^2$.

In some embodiments, a low dosage of cytarabine may range from about 10 mg/m$^2$ to about 100 mg/m$^2$, for example, from about 10 mg/m$^2$ to about 80 mg/m$^2$, from about 10 mg/m$^2$ to about 60 mg/m$^2$, from about 10 mg/m$^2$ to about 40 mg/m$^2$, or from about 10 mg/m$^2$ to about 30 mg/m$^2$. In one example, the low dose of cytarabine is about 20 mg/m$^2$.

In general, alvocidib and cytarabine may be administered by any suitable method, e.g., those described herein. For example, alvocidib may be administered intravenously (e.g., bolus, infusion). In some examples, one dose of alvocidib may be administered as an intravenous bolus in about 15 minutes to about 1 hour, for example, about 30 minutes to about one hour or about 30 minutes. In other examples, a portion of one dose of alvocidib may be administered as an intravenous bolus in about 15 minutes to about 1 hour, for example, about 30 minutes to about one hour or about 30 minutes, and the remaining portion may be administered by intravenous infusion in, e.g., 4-6 hours. Alternatively or in addition, cytarabine may be administered by injection (e.g., subcutaneous injection).

In some examples, a treatment cycle of this treatment regimen comprises (i) a first course of treatment including alvocidib that lasts for 1-4 days (e.g., 1 day); which may be followed by a first drug holiday period of, for example, 1-4 days (e.g., 1 day); (ii) a second course of treatment including cytarabine that lasts for 8-12 days (e.g., 10 days), which may be followed by a second drug holiday period of about 2-4 days (e.g., 2 days); and (iii) a third course of treatment including alvocidib that lasts for about 1-4 days (e.g., for 1 day), which may be followed by a drug holiday period that lasts for 10-14 days (e.g., for 13 days). The treatment cycle may contain 28 days, which may be repeated multiple times as needed, for example, 4-8 times (e.g., 6 times). In some instances, the subject may stay on the treatment, e.g., having an indefinite number of the treatment cycles, until the treatment is no longer clinically indicated (e.g., the treatment confers no substantial treatment benefits, there is evidence of toxicity, such as an NCI CTCAE Grade 4), which can be determined by a medical practitioner.

The first course of treatment may consist of one alvocidib administration on Day 1 of a treatment cycle as described herein, e.g., intravenously (e.g., by bolus) at a low dose as described herein (e.g., about 25 mg/m$^2$). The second course of treatment may consist of one cytarabine administration on each day for a 10-day period (e.g., on Days 3-12 of a treatment cycle), e.g., subcutaneously at a low dose as described herein (e.g., about 20 mg/m$^2$). Alternatively, cytarabine may be given to the subject twice per day for the 10-day period. The third course of treatment may consist of one alvocidib administration on Day 15 of a treatment cycle at a high dose as described herein (e.g., about 50 mg/m$^2$), e.g., intravenously (e.g., by bolus).

In some examples, a treatment cycle of this regimen comprises (i) a first course of treatment including alvocidib that lasts for 2 days; (ii) a second course of treatment including cytarabine that lasts for 10 days (e.g., followed by a 2-day drug holiday period), and (iii) a third course of treatment including alvocidib that lasts for 1 day, followed by a drug holiday period that lasts for 12 days. The treatment cycle may contain 28 days, which may be repeated 4-8 times, for example, 6 times. The first course of treatment may consist of one alvocidib administration on day 1 and day 2, e.g., intravenously (e.g., bolus) at a low dose as described herein (e.g., about 25 mg/m$^2$). The second course of treatment may consist of one cytarabine administration on each day (e.g., on days 3-12), e.g., subcutaneously at a low dose as described herein (e.g., about 20 mg/m$^2$). The third course of treatment may consist of one alvocidib administration on day 15 at a high dose as described herein (e.g., about 50 mg/m$^2$), e.g., intravenously (e.g., bolus).

In some examples, a treatment cycle of this regimen comprises (i) a first course of treatment including alvocidib that lasts for one day; (ii) a second course of treatment including cytarabine that lasts for 10 days (e.g., followed by a 2-day drug holiday period), and (iii) a third course of treatment including alvocidib that lasts for 2 days, followed by a drug holiday period that lasts for 12 days. The treatment cycle may contain 28 days, which may be repeated 4-8 times, for example, 6 times. The first course of treatment may consist of one alvocidib administration on day 1, e.g., intravenously (e.g., bolus) at a low dose as described herein (e.g., about 25 mg/m$^2$). The second course of treatment may consist of one cytarabine administration on each day (e.g., on days 3-12), e.g., subcutaneously at a low dose as described herein (e.g., about 20 mg/m$^2$). The third course of treatment may consist of one alvocidib administration on day 14 and day 15 at a high dose as described herein (e.g., about 50 mg/m$^2$), e.g., intravenously (e.g., bolus).

In some examples, a treatment cycle of this regimen comprises (i) a course of treatment including alvocidib at a low dose that lasts for one day; (ii) a course of treatment including alvocidib at a high dose that lasts for two days, and (iii) a course of treatment including cytarabine at a low dose for 10 days, followed by a drug holiday period. The treatment cycle may contain 28 days, which may be repeated 4-8 times, for example, 6 times. The low-dose alvocidib treatment may consist of one alvocidib administration on day 1, e.g., intravenously (e.g., bolus) at a low dose as described herein (e.g., about 25 mg/m$^2$). The high-dose treatment of alvocidib may consist of alvocidib administrations on two consecutive days at a high dose as described herein (e.g., about 50 mg/m$^2$), e.g., intravenously (e.g., bolus). The low-dose treatment of cytarabine may consists of one cytarabine administration on each day (e.g., on days 3-12), e.g., subcutaneously at a low dose as described herein (e.g., about 20 mg/m$^2$).

In some examples, a treatment cycle of this regimen comprises (i) a course of treatment including alvocidib at a low dose that lasts for two days; (ii) a course of treatment including alvocidib at a high dose that lasts for one day, and (iii) a course of treatment including cytarabine at a low dose for 10 days, followed by a drug holiday period. The treatment cycle may contain 28 days, which may be repeated 4-8 times, for example, 6 times. The low-dose alvocidib treatment may consist of one alvocidib administration on day 1 and day 2, e.g., intravenously (e.g., bolus) at a low dose as described herein (e.g., about 25 mg/m$^2$). The high-dose treatment of alvocidib may consist of alvocidib one administration on one day at a high dose as described herein (e.g., about 50 mg/m$^2$), e.g., intravenously (e.g., bolus). The low-dose treatment of cytarabine may consist of one cytarabine administration on each day (e.g., on days 3-12), e.g., subcutaneously at a low dose as described herein (e.g., about 20 mg/m$^2$).

As used herein, the terms "low dose" or "low dosage," with respect to alvocidib (e.g., a compound of Formula (I), or a pharmaceutically acceptable salt thereof), has its ordinary meaning in the art. In some embodiments, a low dose of alvocidib may be less than or equal to about 50 mg/m$^2$, less than or equal to about 45 mg/m$^2$, less than or equal to about 40 mg/m$^2$, less than or equal to about 35 mg/m$^2$, less than or equal to about 30 mg/m$^2$, less than or equal to about 25 mg/m$^2$, less than or equal to about 20 mg/m$^2$, less than or equal to about 15 mg/m$^2$, or less than or equal to about 10 mg/m$^2$. In certain embodiments, a low dose of alvocidib may be between about 10 mg/m$^2$ and about 50 mg/m$^2$, between about 10 mg/m$^2$ and about 45 mg/m$^2$, between about 10 mg/m$^2$ and about 40 mg/m$^2$, between about 10 mg/m$^2$ and about 35 mg/m$^2$, between about 10 mg/m$^2$ and about 30 mg/m$^2$, between about 15 mg/m$^2$ and about 50 mg/m$^2$, between about 15 mg/m$^2$ and about 45 mg/m$^2$, between about 15 mg/m$^2$ and about 40 mg/m$^2$, between about 15 mg/m$^2$ and about 35 mg/m$^2$, between about 15 mg/m$^2$ and about 30 mg/m$^2$, between about 20 mg/m$^2$ and about 50 mg/m$^2$, between about 20 mg/m$^2$ and about 45 mg/m$^2$, between about 20 mg/m$^2$ and about 40 mg/m$^2$, between about 20 mg/m$^2$ and about 35 mg/m$^2$, or between about 20 mg/m$^2$ and about 30 mg/m$^2$. In some embodiments, the low dose of alvocidib is between about 10 mg/m$^2$ and about 50 mg/m$^2$ (e.g., 25 mg/m$^2$, 19 mg/m$^2$).

As used herein, the terms "high dose" or "high dosage," with respect to alvocidib (e.g., a compound of Formula (I), or a pharmaceutically acceptable salt thereof), has its ordinary meaning in the art. In some embodiments, a high dose of alvocidib may be greater than or equal to about 25 mg/m$^2$, greater than or equal to about 30 mg/m$^2$, greater than or equal to about 35 mg/m$^2$, greater than or equal to about 40 mg/m$^2$, greater than or equal to about 45 mg/m$^2$, greater than or equal to about 50 mg/m$^2$, greater than or equal to about 55 mg/m$^2$, greater than or equal to about 60 mg/m$^2$, greater than or equal to about 65 mg/m$^2$, greater than or equal to about 70 mg/m$^2$, greater than or equal to about 75 mg/m$^2$, greater than or equal to about 80 mg/m$^2$, greater than or equal to about 85 mg/m$^2$, greater than or equal to about 90 mg/m$^2$, or greater than or equal to about 95 mg/m$^2$. In some instances, a high dose of alvocidib is less than or equal to about 100 mg/m$^2$. In some embodiments, a high dose of alvocidib may be between about 25 mg/m$^2$ and about 100 mg/m$^2$, between about 30 mg/m$^2$ and about 100 mg/m$^2$, between about 35 mg/m$^2$ and about 100 mg/m$^2$, between about 40 mg/m$^2$ and about 100 mg/m$^2$, between about 45 mg/m$^2$ and about 100 mg/m$^2$, between about 50 mg/m$^2$ and about 100 mg/m$^2$, between about 30 mg/m$^2$ and about 90 mg/m$^2$, between about 30 mg/m$^2$ and about 80 mg/m$^2$, between about 30 mg/m$^2$ and about 70 mg/m$^2$, between about 30 mg/m$^2$ and about 60 mg/m$^2$, between about 40 mg/m$^2$ and about 90 mg/m$^2$, between about 40 mg/m$^2$ and about 80 mg/m$^2$, between about 40 mg/m$^2$ and about 70 mg/m$^2$, or between about 40 mg/m$^2$ and about 60 mg/m$^2$. In some embodiments, the high dose of alvocidib is between about 25 mg/m$^2$ and about 100 mg/m$^2$ (e.g., about 50 mg/m$^2$).

In some embodiments, the alvocidib in combination with low dose cytarabine regimen may comprise one or more cycles, each comprising two courses of treatment, which may include intervals of one or more drug holiday periods. One course of the treatment may involve a high dose of alvocidib as described herein for 2-5 consecutive days (e.g., 3 consecutive days), following by any of the low dose cytarabine treatments described herein. In some instances, the high dose alvocidib course of treatment is performed before the low dose cytarabine course of treatment.

In some embodiments, the alvocidib in combination with low dose cytarabine regimen may be performed in combination with other therapeutic agents (which do not include venetoclax). Such additional therapeutic agents may be additional anti-cancer agents. Alternatively, the additional therapeutic agents by themselves may have no anti-AML effects but enhance the anti-AML effects of alvocidib or reduce potential side effects of alvocidib. Such additional therapeutic agents include, but are not limited to, an intravenous hydration fluid, allopurinol, a phosphate binder, or a combination thereof. In certain embodiments, the method may further comprise administering an antibiotic, an anti-viral agent, an anti-fungal agent, or a combination thereof (e.g., an effective amount of an antibiotic, an anti-viral agent, an anti-fungal agent, or a combination thereof) to the subject.

Alternative low dose cytarabine treatment may be scheduled into the treatment regimens disclosed herein. Examples include:

Cytarabine at 20 mg/m$^2$ once or twice daily (according to physician's choice) by SC injection for 10 consecutive days. This dosage may be given to AML patients greater than 70 years old.

Cytarabine at 20 mg/m$^2$ in two divided doses 12 hours apart by SC injection for 4 days every week for 4 weeks (in case of CR or partial remission (PR) patients, cytarabine may be given 2 days/week as a maintenance treatment). This dosage may be given to AML patients greater than 60 years old.

First cycle of modified LDAC (mLDAC) cytarabine (20 mg/m$^2$ SC BID) and oral etoposide (50 mg PO BID) for 14 days. This dosing condition may be applied to unfit AML patients greater than 60 years old (e.g., ECOG 2 or greater).

Cytarabine at 20 mg/m$^2$ twice daily (BID) SC on Days 1 through 10 alone IV over 1 hour on days 1+15. This dosing condition may be applied to AML patients having ECOG≤2.

Cytarabine on days 1 to 10 at 40 mg/m$^2$ once daily or 20 mg/m$^2$ twice a day SC, cycle frequency every 28 to 42 days. This dosing condition may be applied to unfit AML patients.

Cytarabine at 20 mg/m$^2$ SC twice daily on Days 1 to 10 (optionally in combination with glasdegib 100 mg orally once daily). This dosing condition may be applied to AML patients greater than 75 years old.

(iii) Treatment Regimens Involving Alvocidib in Combination with Hypomethylating Agents In some embodiments, provided herein are treatment regimens involving alvocidib in combination with a hypomethylating agent, such as decitabine or azacitidine. This regimen may comprise one or more treatment cycles, each of which may contain 28 days.

In some examples, each treatment cycle may comprise a first course of treatment involving one or more administrations of an effective amount of alvocidib to a suitable AML subject (e.g., a patient, such as a patient described herein), and a second course of treatment involving one or more administrations of an effective amount of decitabine or azacitidine to the subject (e.g., patient), either before the alvocidib treatment or after the alvocidib treatment. The first and second course of treatments may be linked immediately. Alternatively, there may be a drug holiday period between the two courses of treatment.

In some embodiments, the effective amount of alvocidib may be from about 20 mg/m$^2$ to about 150 mg/m$^2$ once per day, preferably, from about 20 mg/m$^2$ to about 100 mg/m$^2$ once per day and, more preferably, from about 20 mg/m$^2$ to about 90 mg/m$^2$ once per day. Alvocidib may be given to the patient via a suitable route (e.g., those described herein, such as oral or intravenous injection) once per day for a suitable period, for example, 1-4 consecutive days. In some examples, alvocidib is given to the patient once per day for 1 day. Alternatively, alvocidib may be given to a subject (e.g., patient) once per week for 1-4 consecutive weeks, for example, 2 or 3 weeks.

Alternatively or in addition, the effective amount of decitabine can follow the routine practice of using this compound in cancer therapy. In some examples, it can be given to the AML patient at from about 15 mg/m$^2$ to about 40 mg/m$^2$, preferably, about 20 mg/m$^2$, once every day for 3-10 days. In some examples, decitabine is given to the subject on a daily basis for 5 days. In other instances, decitabine is given to the subject on a daily basis for 10 days.

Similarly, azacitidine can be given to the AML patient following routine practice. In some examples, the effective amount of azacitidine can be from about 50 mg/m$^2$ to about 100 mg/m$^2$, preferably, about 75 mg/m$^2$, once every day for 5-10 days, preferably, for 5 days or 7 days.

In general, alvocidib, decitabine, and azacitidine may be administered by any suitable method, e.g., those described herein. For example, alvocidib (e.g., a compound of Formula (I), or a pharmaceutically acceptable salt thereof) may be administered intravenously (e.g., bolus, infusion). In some examples, one dose of alvodicib may be administered as an intravenous bolus in about 15 minutes to about 1 hour, for example, about 30 minutes to about one hour or about 30 minutes. In other examples, a portion of one dose of alvocidib may be administered as an intravenous bolus in about 15 minutes to about 1 hour, for example, about 30 minutes to about one hour or about 30 minutes, and the remaining portion may be administered by intravenous infusion in, e.g., 4-6 hours. Alternatively or in addition, decitabine may be administered by intravenous injection; and/or azacitidine may be administered by intravenous injection or subcutaneous injection.

In some specific examples, the alvocidib in combination with HMA agent regimen as described herein may include multiple treatment cycles as needed, for example, 4-8 treatment cycles such as 6 cycles. In some instances, the subject may stay on the treatment, e.g., having an indefinite number of the treatment cycles, until the treatment is no longer clinically indicated (e.g., the treatment confers no substantial treatment benefits, there is evidence of toxicity, such as an NCI CTCAE Grade 4), which can be determined by a medical practitioner.

Each cycle, which may contain 28 days, may comprise: (i) administering to the subject (a) decitabine at from about 15 mg/m$^2$ to about 40 mg/m$^2$, preferably, about 20 mg/m$^2$ once every day for 3-10 days (e.g., 5 days or 10 days), or (b) azacitidine at from about 50 mg/m$^2$ to about 100 mg/m$^2$, preferably, about 75 mg/m$^2$, once every day for 5-10 days, preferably, for 5 days or 7 days; and (ii) administering to the subject alvocidib at a dose of from about 20 mg/m$^2$ to about 100 mg/m$^2$ once per day, preferably, from about 20 mg/m$^2$ to about 90 mg/m$^2$ once per day, for about 1 to about 4 days (e.g., for one day). When needed, a first drug holiday period (e.g., 2-4 days, such as 2 days) can be applied between (i) and (ii); and/or a second drug holiday period (e.g., 15-25 days, such as 20 days) may be applied following step (ii).

In one particular example, a 28-day cycle may comprise: (i) administering to the subject decitabine at about 20 mg/m$^2$ once every day on Days 1-5, followed by a first drug holiday period on Days 6 and 7, and (ii) administering to the subject alvocidib at a dose of 20-90 mg/m$^2$ on Day 8, followed by a second drug holiday period on Days 9-28.

In another particular example, a 28-day cycle may comprise: (i) administering to the subject azacitidine at about 75 mg/m$^2$ once every day on Days 1-5, followed by a first drug holiday period on Days 6 and 7, and (ii) administering to the subject alvocidib at a dose of from about 20 mg/m$^2$ to about 90 mg/m$^2$ on Day 8, followed by a second drug holiday period on Days 9-28.

Any of the additional therapeutic agents described herein (which do not comprise venetoclax) can be co-used with a treatment regimen involving alvocidib in combination with an HMA agent described herein.

(iv) Other Treatment Regimens Involving Alvocidib

Alternative treatment regimens involving alvocidib for treatment of AML, subjects with venetoclax failure are also within the scope of the present disclosure.

In some embodiments, provided herein are alvocidib in combination with intermediate dose cytarabine for treating AML with venetoclax failure. Such regimens are essentially similar to the regimens involving alvocidib in combination with low dose cytarabine except that the low dose cytarabine is replaced with intermediate dose cytarabine.

As used herein, the terms "intermediate dose" or "intermediate dosage" with respect to cytarabine has its ordinary meeting in the art. In some embodiments, an intermediate dose of cytarabine may be greater than or equal to about 500 mg/m$^2$, greater than or equal to about 600 mg/m$^2$, greater than or equal to about 700 mg/m$^2$, greater than or equal to about 800 mg/m$^2$, greater than or equal to about 900 mg/m$^2$, greater than or equal to about 1 g/m$^2$, greater than or equal to about 1.2 g/m$^2$, greater than or equal to about 1.4 g/m$^2$, greater than or equal to about 1.5 g/m$^2$, greater than or equal to about 1.6 g/m$^2$, greater than or equal to about 1.8 g/m$^2$, greater than or equal to about 2 g/m$^2$, greater than or equal to about 2.2 mg/m$^2$, greater than or equal to about 2.4 g/m$^2$, greater than or equal to about 2.5 mg/m$^2$, greater than or equal to about 2.6 g/m$^2$, or greater than or equal to about 2.8 mg/m$^2$. In some instances, an intermediate dose of cytarabine is less than or equal to 3 g/m$^2$. In some embodiments, an intermediate dose of cytarabine may be between about 500 mg/m$^2$ and about 3 g/m$^2$, between about 600 mg/m$^2$ and about 3 g/m$^2$, between about 700 mg/m$^2$ and about 3 g/m$^2$, between about 800 mg/m$^2$ and about 3 g/m$^2$, between about 900 mg/m$^2$ and about 3 g/m$^2$, between about 500 mg/m$^2$ and about 2.5 g/m$^2$, between about 600 mg/m$^2$ and about 2.5 mg/m$^2$, between about 700 mg/m$^2$ and about 2.5 g/m$^2$, between about 800 mg/m$^2$ and about 2.5 g/m$^2$, between about 900 mg/m$^2$ and about 2.5 g/m$^2$, between about 500 mg/m$^2$ and about 2 g/m$^2$, between about 600 mg/m$^2$ and about 2 g/m$^2$, between about 700 mg/m$^2$ and about 2 mg/m$^2$, between about 800 mg/m$^2$ and about 2 g/m$^2$, between about 900 mg/m$^2$ and about 2 g/m$^2$, between about 500 mg/m$^2$ and about 1.5 g/m$^2$, between about 600 mg/m$^2$ and about 1.5 g/m$^2$, between about 700 mg/m$^2$ and about 1.5 mg/m$^2$, between about 800 mg/m$^2$ and about 1.5 g/m$^2$, between about 900 mg/m$^2$ and about 1.5 g/m$^2$, between about 500 mg/m$^2$ and about 1.2 g/m$^2$, between about 600 mg/m$^2$ and about 1.2 g/m$^2$, between about 700 mg/m$^2$ and about 1.2 mg/m$^2$, between about 800 mg/m$^2$ and about 1.2 mg/m$^2$, or between about 900 mg/m$^2$ and about 1.2 g/m$^2$. In some embodiments, the intermediate dose of cytarabine is between about 500 mg/m$^2$ and about 3 g/m$^2$. In some embodiments, the intermediate dose of cytarabine is about 1 g/m$^2$.

An intermediate dose of cytarabine may range from about 500 mg/m$^2$ to about 3 g/m$^2$, for example, about 800 mg/m$^2$ to about 3 g/m$^2$, about 1 g/m$^2$ to about 3 g/m$^2$, about 1 g/m$^2$ to about 2 g/m$^2$, about 500 mg/m$^2$ to about 2 g/m$^2$, or about 800 mg/m$^2$ to about 1.5 g/m$^2$. In one example, the intermediate dose of cytarabine is about 1 g/m$^2$. The intermediate dose of cytarabine may be given to a patient for 3-8 consecutive days, preferably, for 5 days.

In other embodiments, alternative regimens involve a combination of alvocidib and cytarabine, which may involve one course treatment of alvocidib and one course treatment of cytarabine in each treatment cycle without a second course of alvocidib treatment. Such a treatment regimen may also be free of mitoxantrone. For example, this regimen may contain one or multiple treatment cycles (e.g., 4-8, such as 6), each of which may contain 28 days. In each cycle, an effective amount of alvocidib may be given to a patient in a first course of treatment, and an effective amount of cytarabine may be given to the patient in a second course of treatment. In some examples, the first course of treatment is performed prior to the second course of treatment. In other examples, the second course of treatment is performed prior to the first course of treatment. The two courses of treatment may be performed immediately one after another. Alternatively, they may be separated by a drug holiday period.

In some embodiments, the effective amount of cytarabine in the second course of treatment is from about 50 mg/m$^2$ to about 500 mg/m$^2$ per day, preferably, from about 100 mg/m$^2$ to about 1 g/m$^2$ per day. In one example, the effective amount of cytarabine in the second course of treatment is from about 1 g/m$^2$ to about 3 g/m$^2$ per day. Cytarabine may be given to the patient on a daily basis for 8-12 days, preferably, for 10 days.

Alternatively or in combination, the effective amount of alvocidib in the first course of treatment may be from about 25 mg/m$^2$ to about 100 mg/m$^2$ per day, preferably, about 50 mg/m$^2$ per day, for about 1 to about 4 days. In some examples, alvocidib is given to the patient on a daily basis at a dose of from about 80 mg/m$^2$ to about 120 mg/m$^2$, preferably, about 90 mg/m$^2$.

In some examples, alvocidib is first given to a patient at any of the doses described herein for three consecutive days, followed by a 2-day drug holiday period. Cytarabine is then given to the patient at a dose of from about 1 g/m$^2$ to about 3 g/m$^2$, preferably, 2 g/m$^2$, by intravenous injection in about 72 hours.

In general, alvocidib and cytarabine may be administered by any suitable method, e.g., those described herein. For example, alvocidib (e.g., a compound of Formula (I), or a pharmaceutically acceptable salt thereof) may be administered intravenously (e.g., bolus, infusion). In some examples, one dose of alvocidib may be administered as an intravenous bolus in about 15 minutes to about 1 hour, for example, about 30 minutes to about one hour or about 30 minutes. In other examples, a portion of one dose of alvocidib may be administered as an intravenous bolus in about 15 minutes to about 1 hour, for example, about 30 minutes to about one hour or about 30 minutes, and the remaining portion may be administered by intravenous infusion in, e.g., 4-6 hours. Alternatively or in addition, cytarabine may be administered via intravenous infusion or subcutaneous injection.

Methods for Reducing Tumor Lysis Syndrome (TLS)

Tumor lysis syndrome (TLS) is a metabolic syndrome that is caused by the sudden killing of tumor cells with chemotherapy, radiotherapy, etc., or spontaneous lysis of tumors. When tumor cells die rapidly, they release their cellular contents, including large amounts of potassium, phosphate, and nucleic acids, into the systemic circulation. TLS causes hyperkalemia, hyperphosphatemia, hypocalcemia, hyperuricemia, and higher than normal levels of blood urea nitrogen (BUN) and other nitrogen-containing compounds (azotemia). Hyperuricemia and hyperphosphatemia, for example, lead to acute kidney injury and acute renal failure. In some cases, TLS leads to a reduction in the amount of chemotherapeutic agent being delivered, or cessation of the treatment until the patient recovers, which may be detrimental to the overall treatment of the cancer.

Any of the treatment regimens can be used to reduce the risk of TLS occurrence and/or prevent TLS occurrence in a subject having a hematological cancer (e.g., an AML, patient) subject to such treatment regimens. Thus, also provided herein are methods of reducing the risk of TLS occurrence, preventing TLS occurrence, and/or reducing mortality caused by TLS in AML patients who failed prior venetoclax treatment. Such methods would involve administering to the subject alvocidib, either alone or in combination with cytarabine, decitabine, or azacitidine following the dosages and dosing schedules described herein.

Hematological cancers are cancers that begin in blood-forming tissue or cells of the immune system. Hematological cancers include, but are not limited to, multiple myeloma, myelodysplastic syndrome (MDS), acute myeloid leukemia (AML), acute lymphoblastic leukemia (ALL), acute lymphocytic leukemia, chronic lymphogenous leukemia, chronic lymphocytic leukemia (CLL), mantle cell lymphoma, diffuse large B-cell lymphoma, follicular lymphoma, or non-Hodgkin's lymphoma. In specific embodiments, the hematological cancer is multiple myeloma, AML, acute lymphocytic leukemia, chronic lymphogenous leukemia, mantle cell lymphoma, diffuse large B-cell lymphoma, and non-Hodgkin's lymphoma. In some embodiments, the hematological cancer is AML. In some embodiments, the hematological cancer is CLL. In some embodiments, the hematological cancer is multiple myeloma.

Also described herein are methods for reducing the severity of TLS (e.g., from grade 5 to grade 3 or 4, from grade 4 or 5 to grade 3, eliminating grade 3, 4 or 5 TLS, according to the CTCAE 5.0 grading scale for TLS; reducing the severity of the symptoms of TLS) in a hematological cancer subject(s), reducing the incidence of TLS (e.g., grade 3 TLS, grade 4 TLS, grade 5 TLS, grade 4 or grade 5 TLS, grade 3, 4 or 5 TLS, according to the CTCAE 5.0 grading scale for TLS) in a hematological cancer subject(s) being treated with alvocidib, monitoring for TLS while treating a hematological cancer subject(s) with alvocidib, decreasing mortality from TLS in a hematological subject(s) being treated with alvocidib, increasing survival time of a hematological cancer subject(s) being treated with alvocidib, preventing TLS (e.g., grade 3 TLS, grade 4 TLS, grade 5 TLS, grade 4 or grade 5 TLS, grade 3, 4 or 5 TLS, according to the CTCAE 5.0 grading scale for TLS) in a hematological cancer subject(s) being treated with alvocidib, and/or diagnosing and/or treating TLS in a hematological cancer subject(s) being treated with alvocidib. In one aspect, the methods comprise (e.g., for each subject, if more than one subject is implicated) treating the subject in accordance with any of the treatment regimens described herein. It will be appreciated that when more than one subject is implicated by a particular preamble, the recited administering step(s) should be carried out with respect to each subject individually.

"Reducing the severity of TLS," as used herein, includes improving a condition, symptom, disorder, or parameter associated with TLS, e.g., to a clinically meaningful extent. Reducing the severity of TLS can be evidenced by reducing TLS from grade 5 to grade 3 or 4, from grade 4 or 5 to grade 3, and/or eliminating grade 3, 4 or 5 TLS altogether, according to the CTCAE 5.0 TLS grading scale. Reducing the severity of TLS can also be evidenced by a reduction in the severity of a symptom associated with TLS.

"Reducing the incidence of TLS," as used herein, includes preventing TLS (e.g., grade 3, grade 4 and/or grade 5 TLS, according to CTCAE 5.0 TLS grading), e.g., the occurrence or re-occurrence of TLS, in an individual subject, and reducing the occurrence, rate or frequency of TLS in a population of subjects.

"Decreasing mortality from TLS," as used herein, includes preventing death from TLS, or a sequela thereof, in an individual subject, and reducing the occurrence, rate or frequency of death from TLS, or a sequela thereof, in a population of subjects. It is understood that a death may not always be solely or definitively attributable to particular cause(s), particularly not in the context of cancer treatment. "From TLS" thus includes mortalities for which TLS, or a sequela thereof, is a substantial and/or likely contributing factor in addition to mortalities for which TLS, or a sequela thereof, is the sole and/or definitive cause of the mortality.

"Increasing survival time," as used herein, includes prolonging the life of an individual subject, e.g., beyond the mean and/or median survival time associated with a particular cancer and/or therapeutic regimen, and extending the mean and/or median survival time of a population of subjects, e.g., beyond the mean and/or median survival time associated with a particular cancer and/or therapeutic regimen.

While reducing the severity of TLS in, reducing the incidence of TLS in, monitoring for the development of TLS while treating, decreasing mortality from TLS in, increasing survival time of, and/or preventing TLS in a hematological cancer subject being treated with alvocidib can be done at the level of an individual subject, such methods can also be applied to populations of subjects, and assessed at a population-wide level, for example, as is commonly done in the context of a clinical trial. Assessment of these methods at the individual and the population-wide level, including selection of and comparison to appropriate controls and/or comparators, is within the abilities of a person of ordinary skill in the relevant art.

Any of the methods for reducing TLS described herein may comprise administering low-dose alvocidib (e.g., at a first dose of less than or about 50 mg/m$^2$, from about 10 mg/m$^2$ to about 50 mg/m$^2$, from about 15 mg/m$^2$ to about 40 mg/m$^2$ or about 25 mg/m$^2$) to a subject (e.g., a subject described herein) in the absence of venetoclax. In some embodiments, the methods further comprise administering high-dose alvocidib (e.g., at a second dose of greater than or equal to about 25 mg/m$^2$, from about 40 mg/m$^2$ to about 100 mg/m$^2$ or about 50 mg/m$^2$) to the subject in the absence of venetoclax.

The methods of the present disclosure (e.g., the methods for reducing TLS described herein) can include one or more TLS therapies.

As used herein, the term "TLS therapy" refers to a treatment for hyperkalemia, hyperuricemia, hyperphosphatemia, coagulopathy, increased serum creatinine, cytokine release syndrome, oliguric renal failure (e.g., urine output less than 800 mL/day), cardiac arrhythmia, tetany and/or seizures. Such treatments are administered to a patient prophylactically or in response to the development of one or more of the aforementioned conditions or disorders, and such treatments can be administered once, or multiple times to a subject. TLS therapies include, but are not limited to, prophylactic administration of pretreatment IV hydration, oral allopurinol, and oral phosphate binder, as well as diligent monitoring of urine output to ensure that it equals fluid input. If input is greater than output by 10%, administration of diuretics is recommended. Replacement of excessive fluid losses, including from diarrhea is also recommended, unless otherwise clinically indicated, along with the following treatments related to laboratory abnormalities:

If potassium levels are increasing to >4.0 mEq/L, patients should receive a 30-gm dose of sodium polystyrene sulfonate, unless there are other likely causes of hyperkalemia other than TLS, or a contraindication to its use.

If potassium levels rise to >5.0 mEq/L, in addition to the 30-gm dose of sodium polystyrene sulfonate, patients should also receive 10 units of IV rapid-acting insulin and 25 gm (one ampoule) of IV dextrose 50%, unless there are other likely causes of hyperkalemia other than TLS, or a contraindication to its use.

If potassium levels rise to >5.5 mEq/L, patients should be considered for emergent intermittent or continuous dialysis.

Calcium supplementation should only be given for symptomatic hypocalcemia in this setting to avoid renal precipitation of calcium phosphate crystals.

Patients who develop clinical evidence of cytokine release syndrome or who have hyperkalemia requiring dialysis will receive immediate steroid therapy with an equivalent of at least 20 mg of IV dexamethasone.

As used herein, a "prophylactically effective amount" is an amount that achieves prevention of a disease or condition (e.g., TLS). In some embodiments, a prophylactically effective amount of one or more TLS therapies (e.g., IV hydration, allopurinol, an oral phosphate binder) is administered to a subject. It will be understood by the skilled clinician that the effective amount and the prophylactically effective amount of an agent need not be different in the context of this invention, though they can be.

In one embodiment, the methods further comprise administering to the subject (e.g., a prophylactically effective amount of) intravenous (IV) hydration (e.g., at a rate of from about 50 to about 750 cc/hour, from about 100 to about 500 cc/hour, from about 250 to about 500 cc/hour, about 100 cc/hour, 200 cc/hour, 250 cc/hour, 300 cc/hour, 350 cc/hour, 400 cc/hour, 450 cc/hour or 500 cc/hour), e.g., beginning about 24 hours, about 12 hours, about 6 hours, about 2 hours or about 1 hour prior to the administration of alvocidib. In one embodiment, the methods further comprise administering to the subject continuous IV hydration. As used herein, the term "IV hydration" means 0.45% NaCl aqueous solution, or similar hydration fluid.

In some embodiments, IV hydration is administered prior to the start of the alvocidib administration (e.g., during the time period leading up to the alvocidib administration, such that, for example, alvocidib administration commences immediately or almost immediately, e.g., within 30 minutes, of completion of IV hydration). In some embodiments, IV hydration is administered beginning at least two hours (e.g., about one to about two hours, about one hour, about two hours) prior to the start of the alvocidib administration, and continues for at least two hours (e.g., the at least two hours, from about one hour to about two hours, about one hour, about two hours). In some embodiments, IV hydration is also or alternatively administered for from about one to about two hours, beginning at the end of the alvocidib administration.

Certain embodiments of a method for reducing TLS further comprise administering to a subject an effective amount and/or a prophylactically effective amount (e.g., a prophylactically effective amount) of allopurinol (e.g., from about 300 mg to about 600 mg per day) and/or an effective amount and/or prophylactically effective amount (e.g., a prophylactically effective amount) of an oral phosphate binder. Concurrent with the administration of continuous IV hydration, in certain embodiments, the subject is also administered a prophylactically effective amount of allopurinol, at the start of the administration of IV hydration and, optionally, a prophylactically effective amount of an oral phosphate binder (e.g., at the start of the administration of IV hydration). In certain embodiments, the subject is administered an effective amount of allopurinol, beginning at the start of the administration of IV hydration and/or an effective amount of an oral phosphate binder, beginning at the start of the administration of IV hydration. In certain embodiments, the subject is administered an effective amount of allopurinol beginning at least or about 72 hours, at least or about 48 hours, at least or about 36 hours, at least or about 24 hours, at least or about 12 hours, at least or about 6 hours prior to the start of the alvocidib administration, or at the start of the alvocidib administration and/or an effective amount of an oral phosphate binder, beginning at the start of the administration of continuous IV hydration. Typically, administration of allopurinol and/or the oral phosphate binder will continue throughout the first cycle of treatment (e.g., to day 28 of a 28-day treatment cycle), although in some embodiments, administration of allopurinol and/or an oral phosphate binder will independently continue for one, two, three, four, five, six, seven, eight, nine, 10, 11, 12, 13, 14 or 15 days, for the first cycle of treatment, or for each day of dosing, e.g., of alvocidib of the alvocidib-containing treatment regimen. In some embodiments, administration of allopurinol continues throughout the first cycle of treatment, and administration of the oral phosphate binder continues for seven days. Effective amounts and prophylactically effective amounts of allopurinol and/or an oral phosphate binder are well-known in the art, and/or can be readily determined by a skilled artisan.

Examples of oral phosphate binders include, but are not limited to, calcium acetate, sevelamer, ferric citrate, lanthanum carbonate, sucroferric oxyhydroxide and aluminum hydroxide.

The methods of the present disclosure (e.g., the methods for reducing TLS described herein) can further include monitoring the subject for TLS. In some embodiments, monitoring the subject for TLS includes performing a serum potassium assay on the subject at the end of the alvocidib administration and about two hours after the end of the alvocidib administration, and performing a serum laboratory TLS panel on the subject about four hours after the end of the alvocidib administration. In some embodiments, monitoring the subject for TLS further includes performing a serum laboratory TLS panel on the subject prior to the alvocidib administration. In some embodiments, monitoring the subject for TLS further includes performing an additional serum laboratory TLS panel on the subject weekly after the first week following the alvocidib administration.

As used herein, the term "laboratory TLS panel" means at least two diagnostic tests that are utilized alone or in combination to diagnose a subject for the presence of TLS, or provide evidence of clinically meaningful TLS in a subject. The specific diagnostic tests that comprise a laboratory TLS panel can vary from institution to institution, but typically include one or more of the following diagnostic assays: serum phosphate assay for detecting hyperphosphatemia; serum uric acid assay for detecting hyperuricemia; serum electrolyte assays including serum sodium for detecting hypernatremia, serum potassium for detecting hyperkalemia, serum chloride for detecting hyperchloremia, and carbon dioxide for detecting acidosis or alkalosis; serum calcium assay for detecting hyper- or hypocalcemia; serum creatinine assay for detecting renal injury or failure; and lactate dehydrogenase (LDH) assay for detecting tissue damage. In one embodiment, the laboratory TLS panel comprises a serum potassium assay. In one embodiment, the laboratory TLS panel comprises a serum potassium assay, a serum uric acid assay, a serum chloride assay, a serum sodium assay, a serum creatinine assay, a serum phosphate assay, a serum calcium assay, a serum LDH assay, and a serum carbon dioxide assay. In another embodiment, the laboratory TLS panel comprises a serum potassium assay, a serum uric acid assay, a serum phosphate assay, and a serum calcium assay. In another embodiment, a laboratory TLS panel comprises a serum potassium assay. In yet another embodiment, a laboratory TLS panel comprises a serum phosphate assay for detecting hyperphosphatemia; serum uric acid assay for detecting hyperuricemia; serum electrolyte assays including serum sodium for detecting hypernatremia, serum potassium for detecting hyperkalemia, serum chloride for detecting hyperchloremia, and carbon dioxide for detecting acidosis or alkalosis; serum calcium assay for detecting hyper- or hypocalcemia and serum creatinine assay for detecting renal injury or failure. In yet other embodiments, a laboratory TLS panel comprises a serum calcium assay; serum phosphate assay; serum potassium assay; serum uric acid assay; serum LDH assay; and serum creatinine assay.

The methods of the present disclosure (e.g., the methods for reducing TLS described herein) can also further comprise administering to the subject an effective amount of one or more TLS therapies if the subject has an elevated serum potassium level or an abnormal laboratory TLS panel.

As used herein, the term "abnormal laboratory TLS panel" means (i) at least two of the results from the diagnostic tests of potassium, uric acid, phosphate and calcium show greater than 25% change from baseline values or above the normal laboratory values, or (ii) at least one of the diagnostic tests of potassium, uric acid, phosphate and calcium is above normal limits and serum creatinine levels are above 1.4 mg/dL. Normal limits can vary among institutions, however, the skilled artisan can readily recognize normal laboratory values or above normal laboratory values. For example, a serum level of potassium greater than 5 mEq/L, uric acid greater than 7.5 mg/dL, phosphate greater than 5 mg/dL and/or calcium less than 8 mg/dL can all be indicative of serum levels above normal limits.

In some embodiments, the methods further comprise administering a prophylactically effective amount of each of: IV hydration (e.g., continuous IV hydration), allopurinol and an oral phosphate binder to the subject; and monitoring the subject for TLS by performing a serum potassium assay on the subject at the end of the alvocidib administration and about two hours after the end of the alvocidib administration, and performing a serum laboratory TLS panel on the subject about four hours (e.g., four hours±30 minutes) after the end of the alvocidib administration. In some embodiments, the methods further comprise administering to the subject a therapeutically effective amount of one or more TLS therapies if the subject has an elevated serum potassium level or an abnormal laboratory TLS panel.

The methods described herein may also comprise identifying AML patients who are at risk for developing TLS in AML treatment, and/or monitoring TLS occurrence during the treatments described herein. Methods for identifying such AML patients and/or monitoring TLS occurrence can be found in U.S. Provisional Patent Application Nos. 62/745,269 and 62/871,799, and in International Application No. PCT/US2019/055986, the relevant disclosures of which are incorporated by reference in their entireties for this particular purpose.

Kits for Use in Treating AML with Venetoclax Failure

The present disclosure also provides kits for use in treating AML with venetoclax failure. Such kits can include one or more containers comprising alvocidib, and one of the other therapeutic agents described herein, including cytarabine, decitabine, and azacitidine, or pharmaceutical compositions comprising such.

In some embodiments, the kit can comprise instructions for use in accordance with any of the methods described herein. For example, the included instructions can comprise a description of administration of the composition that comprises alvocidib or other therapeutic agents to treat, delay the onset, or alleviate a target disease described herein. The kit may further comprise a description of selecting an individual suitable for treatment based on identifying whether that individual has the target disease and/or failed in prior venetoclax treatment. In still other embodiments, the instructions comprise a description of administering the composition comprising alvocidib and/or other therapeutic agents described herein to an individual having the target disease with venetoclax failure.

The instructions relating to the use of any of the pharmaceutical compositions described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert can indicate that the composition(s) is used for treating, delaying the onset and/or alleviating a disease or disorder associated with cancer, such as those described herein (e.g., AML). Instructions may be provided for practicing any of the methods described herein.

The kits as described herein are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example, the container may be an intravenous solution bag or a vial having a stopper pierceable by a hypodermic injection needle). The container may also have a sterile access port (for example, the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introuction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLE EMBODIMENTS

A1. A method for treating acute myeloid leukemia (AML) in a subject in need thereof, the method comprising: administering an effective amount of alvocidib, to the subject in the absence of venetoclax, wherein the subject has refractory, resistant, or relapsed AML after one or more prior therapies, at least one of which comprises venetoclax.

A2. The method of claim A1, wherein the one or more prior therapies further comprise one or more other therapeutic agents for treating AML.

A3. The method of claim A2, wherein the one or more other therapeutic agents for treating AML is azacitidine, decitabine, or a combination thereof.

A4. The method of any one of claims A1-A3, wherein the method comprises the alvocidib as a sole treatment agent for AML.

A5. The method of any one of claims A1-A4, wherein the alvocidib is a compound having the structure of Formula (I):

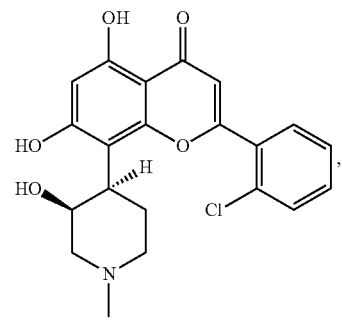

or a pharmaceutically acceptable salt thereof.

A6. The method of any one of claims A1-A4, wherein the alvocidib is a compound having the structure of Formula (I-b):

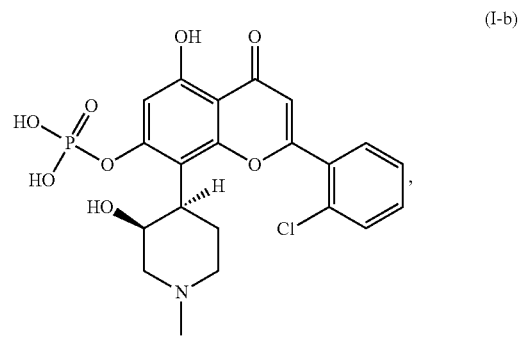 [SMILES: CN1CC[C@H](c2c(OP(=O)(O)O)cc(O)c3c(=O)cc(-c4ccccc4Cl)oc23)[C@H](O)C1]

or a pharmaceutically acceptable salt thereof.

A7. The method of any one of claims A1-A6, wherein the subject has refractory AML, and the one or more prior therapies comprise up to 2 cycles of venetoclax treatment.

A8. The method of any one of claims A1-A6, wherein the subject has relapsed AML after the one or more prior therapies.

A9. The method of claim A8, wherein the subject has relapsed AML, after a first complete remission (CR1) period of about 90 days to about 18 months.

A10. The method of any one of claims A1-A9, wherein the effective amount of the alvocidib is from about 20 mg/m$^2$ to about 100 mg/m$^2$ once per week.

A11. The method of any one of claims A1-A10, wherein the effective amount of the alvocidib is about 25 mg/m$^2$ or about 50 mg/m$^2$ once per week.

A12. The method of any one of claims A1-A11, wherein the alvocidib is administered to the subject at a dose of from about 20 mg/m$^2$ to about 100 mg/m$^2$ as an intravenous bolus in about 15 minutes to about an hour once every week.

A13. The method of any one of claims A1-A10, wherein the alvocidib is administered to the subject at a dose of from about 25 mg/m$^2$ to about 50 mg/m$^2$ as an intravenous bolus in about 30 minutes.

A14. The method of claim A13, wherein the alvocidib is administered to the subject at a dose of about 25 mg/m$^2$ or about 50 mg/m$^2$.

A15. The method of any one of claims A1-A14, wherein alvocidib is administered to the subject once every week for about 1 to about 4 consecutive weeks, followed by a drug holiday period of about 1 to about 3 weeks as a treatment cycle.

A16. The method of claim A15, wherein the alvocidib is administered to the subject once every week for 3 consecutive weeks followed by a drug holiday period of 1 week as a treatment cycle.

A17. The method of any one of claims A1-A16, wherein the method comprises 1-8 of the treatment cycles.

A18. The method of any one of claims A1-A16, wherein the method comprises a plurality of the treatment cycles until the treatment shows substantially no benefit on the subject.

A19. The method of any one of claims A15-A18, wherein each treatment cycle comprises: (i) administering alvocidib to the subject at a dose of from about 15 mg/m$^2$ to about 40 mg/m$^2$ as an intravenous bolus in about 15 minutes to about an hour, and (ii) about one week after step (i), administering alvocidib to the subject at a dose of from about 40 mg/m$^2$ to about 80 mg/m$^2$ as an intravenous bolus in about 15 minutes to about an hour once every week for 2-4 weeks, followed by a drug holiday period of about 2 to about 4 weeks.

A20. The method of any one of claims A15-A19, wherein each treatment cycle consists of 4 weeks, and comprises: (i) administering alvocidib to the subject at a dose of about 25 mg/m$^2$ as an intravenous bolus in about 30 minutes on the first day of the first week, and (ii) administering alvocidib to the subject at a dose of about 50 mg/m$^2$ as an intravenous bolus in about 30 minutes on the first day of the second week and the first day of the third week, followed by a drug holiday period of about 1 week.

A21. The method of any one of claims A15-A20, wherein the method comprises 2-6 treatment cycles.

A22. The method of claim A21, wherein the method comprises 3-5 treatment cycles.

A23. The method of any one of claims A1-A22, further comprising terminating administration of alvocidib in a subject who fails to achieve at least about a 20% reduction in leukemia blast count.

A24. The method of any one of claims A1-A23, further comprising administering to the subject an effective amount of acyclovir, trimethoprim, sulfamethoxazole, or a combination thereof.

A25. The method of any one of claims A1-A24, further comprising administering an effective amount of ciprofloxacin to the subject who has neutropenia.

A26. The method of any one of claims A1-A25, wherein the subject is free of a treatment comprising a granulocyte colony stimulating factor.

A27. The method of any one of claims A1-A26, wherein the subject is MCL-1 dependent.

A28. The method of any one of claims A1-A27, wherein the subject is identified as MCL-1 dependent.

A29. The method of claim A28, wherein the subject is identified as MCL-1 dependent by examining a bone marrow sample of the subject.

A30. The method of claim A6, wherein the compound of Formula (I-b), or pharmaceutically acceptable salt thereof, is administered to the subject orally.

A31. The method of any one of claims A1-A30, wherein the subject is measurable residual disease (MRD)-positive prior to being administered the alvocidib.

A32. The method of any one of claims A1-A31, wherein the subject is measurable residual disease (MRD)-negative after being administered the alvocidib.

A33. The method of any one of claims A1-A32, further comprising detecting the measurable residual disease (MRD) status of the subject.

A34. The method of claim A33, wherein the MRD status of the subject is detected prior to administering the alvocidib to the subject.

A35. The method of claim A33, wherein the MRD status of the subject is detected after administering the alvocidib to the subject.

A36. The method of any one of claims A33-A35, wherein the MRD status of the subject is detected prior to and after administering the alvocidib to the subject.

A37. The method of any one of claims A1-A36, further comprising terminating administration of the alvocidib to the subject if the subject is determined to be measurable residual disease (MRD)-negative.

B1. A method for treating acute myeloid leukemia (AML) in a subject in need thereof, the method comprising, in the absence of venetoclax:

(i) administering to the subject an effective amount of alvocidib in a first course of treatment;

(ii) administering to the subject an effective amount of cytarabine in a second course of treatment; and (iii) administering to the subject an effective amount of alvocidib in a third course of treatment;

wherein the subject has refractory, resistant, or relapsed AML after one or more prior therapies, at least one of which comprises venetoclax.

B2. The method of claim B1, wherein the one or more prior therapies further comprise one or more other therapeutic agents for treating AML.

B3. The method of claim B2, wherein the one or more other therapeutic agents comprise azacitidine, decitabine, or a combination thereof.

B4. The method of any one of claims B1-B3, wherein the alvocidib is a compound having the structure of Formula (I):

(I)

or a pharmaceutically acceptable salt thereof.

B5. The method of any one of claims B1-B3, wherein the alvocidib is a compound having the structure of Formula (I-b):

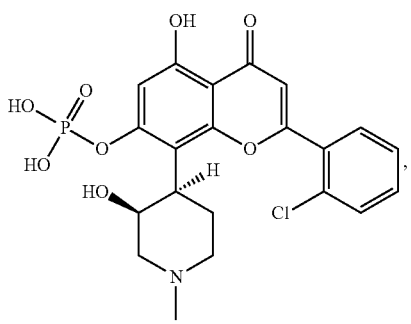

or a pharmaceutically acceptable salt thereof.

B6. The method of any one of claims B1-B5, wherein step (ii) is performed after step (i), and step (iii) is performed after step (ii).

B7. The method of any one of claims B1-B6, wherein the effective amount of the alvocidib in the first course of treatment differs from the effective amount of the alvocidib in the third course of treatment.

B8. The method of any one of claims B1-B7, wherein the effective amount of the alvocidib in the first course of treatment is from about 10 mg/m$^2$ to about 50 mg/m$^2$ per day.

B9. The method of claim B8, wherein the effective amount of the alvocidib in the first course of treatment is about 25 mg/m$^2$ per day.

B10. The method of any one of claims B1-B9, wherein the first course of treatment consists of about 1 to about 4 days.

B11. The method of claim B10, wherein the first course of treatment consists of one day or two days.

B12. The method of any one of claims B1-B11, where the effective amount of the cytarabine in the second course of treatment is from about 10 mg/m$^2$ to about 100 mg/m$^2$ per day.

B13. The method of claim B12, wherein the effective amount of the cytarabine in the second course of treatment is about 20 mg/m$^2$ per day.

B14. The method of any one of claims B1-B13, wherein the second course of treatment consists of 8-12 days.

B15. The method of claim B14, wherein the second course of treatment consists of 10 days.

B16. The method of any one of claims B1-B15, wherein the effective amount of the alvocidib in the third course of treatment is from about 25 mg/m$^2$ to about 100 mg/m$^2$ per day.

B17. The method of claim B16, wherein the effective amount of the alvocidib in the third course of treatment is about 50 mg/m$^2$ per day.

B18. The method of any one of claims B1-B17, wherein the third course of treatment consists of 1-3 days.

B19. The method of claim B18, wherein the third course of treatment consists of 1 day or 2 days.

B20. The method of any one of claims B1-B19, wherein the first course of treatment consists of 1 day and is followed by a first drug holiday period of 1 day, prior to the commencement of the second course of treatment.

B21. The method of any one of claims B1-B20, wherein the second course of treatment consists of 10 days and is followed by a second drug holiday period of 2 days, prior to the commencement of the third course of treatment.

B22. The method of any one of claims B1-B21, wherein the third course of treatment consists of 1 day and is followed by a third drug holiday period of about 13 days.

B23. The method of any one of claims B1-B22, wherein the method comprises multiple treatment cycles, and each treatment cycle comprises the first course of treatment, the second course of treatment, and the third course of treatment, and is repeated every 28 days.

B24. The method of claim B23, wherein each treatment cycle comprises:
(i) administering the alvocidib to the subject at a daily dose of from about 10 mg/m$^2$ to about 50 mg/m$^2$ as an intravenous bolus in about 15 minutes to about one hour for about 1 to about 3 days, followed by a first drug holiday period of about 1 to about 3 days;
(ii) administering the cytarabine to the subject by subcutaneous injection at a daily dose of from about 15 mg/m$^2$ to about 40 mg/m$^2$ for 8-12 days, followed by a second drug holiday period of 1-3 days, and
(iii) administering the alvocidib to the subject at a daily dose of from about 25 mg/m$^2$ to about 100 mg/m$^2$ as an intravenous bolus in about 15 minutes to about one hour for about 1 to about 3 days, followed by a third drug holiday period of about 12 to about 14 days.

B25. The method of claim B24, wherein each treatment cycle comprises:
(i) administering the alvocidib to the subject at a daily dose of about 25 mg/m$^2$ as an intravenous bolus in about 30 minutes for one day in the first course of treatment, followed by the first drug holiday period of one day;
(ii) administering the cytarabine to the subject by subcutaneous injection at a daily dose of about 20 mg/m$^2$ for 10 days in the second course of treatment, followed by a second drug holiday period of 2 days; and
(iii) administering the alvocidib to the subject at a daily dose of about 50 mg/m$^2$ as intravenous bolus in about 30 minutes for 1 day in the third course of treatment, followed by the third drug holiday period of about 13 days.

B26. The method of claim B24 or B25, wherein each treatment cycle consists of 28 days, and comprises:
(i) administering the alvocidib to the subject at a daily dose of about 25 mg/m$^2$ as an intravenous bolus in about 30 minutes on Day 1, followed by the first drug holiday period on Day 2;
(ii) administering the cytarabine to the subject by subcutaneous injection at a daily dose of about 20 mg/m$^2$ on Days 3-12, followed by the second drug holiday period on Days 13-14; and
(iii) administering the alvocidib to the subject at a daily dose of about 50 mg/m$^2$ as an intravenous bolus in about 30 minutes on Day 15, followed by the third drug holiday period on Days 16-28.

B27. The method of any one of claims B1-B5, wherein step (iii) is performed after step (i), and step (ii) is performed after step (iii).

B28. The method of claim B27, wherein steps (i), (ii), and (iii) are separated by one or more drug holiday periods.

B29. The method of claim B27 or claim B28, wherein the effective amount of alvocidib in the first course of treatment is from about 10 mg/m$^2$ to about 50 mg/m$^2$ per day.

B30. The method of claim B29, wherein the effective amount of alvocidib in the first course of treatment is about 25 mg/m$^2$.

B31. The method of any one of claims B27-B29, wherein the first course of treatment consists of about 1-4 days.

B32. The method of claim B31, wherein the first course of treatment consists of one day or two days.

B33. The method of any one of claims B27-B32, wherein the effective amount of the alvocidib in the third course of treatment is from about 25 mg/m$^2$ to about 100 mg/m$^2$ per day.

B34. The method of claim B33, wherein the effective amount of the alvocidib in the third course of treatment is about 50 mg/m$^2$ per day.

B35. The method of any one of claims B27-B34, wherein the third course of treatment consists of 1-3 days.

B36. The method of claim B35, wherein the third course of treatment consists of 1 day or 2 days.

B37. The method of any one of claims B27-B36, wherein the first course of treatment consists of 1 day and the third course of treatment consists of 2 days, or wherein the first course of treatment consists of 2 days and the third course of treatment consists of 1 day.

B38. The method of any one of claims B27-B37, wherein the effective amount of the cytarabine in the second course of treatment is from about 10 mg/m$^2$ to about 100 mg/m$^2$ per day.

B39. The method of claim B38, wherein the effective amount of the cytarabine in the second course of treatment is about 20 mg/m$^2$ per day.

B40. The method of claim B38 or B39, wherein the second course of treatment consists of 8-12 days.

B41. The method of claim B40, wherein the second course of treatment consists of 10 days.

B42. The method of any one of claims B1-B41, wherein the effective amount of cytarabine in the second course of treatment is 20 mg/m$^2$ once or twice daily for 10 days.

B43. The method of any one of claims B1-B42, wherein the effective amount of cytarabine in the second course of treatment is 20 mg/m$^2$ daily, which is divided into two doses, for 4 days, and wherein the two doses are administered to the subject 12 hours apart.

B44. The method of claim B43, wherein the cytarabine is administered to the subject 2 days per week.

B45. The method of any one of claims B1-B42, wherein the effective amount of the cytarabine in the second course of treatment is 20 mg/m$^2$ twice daily for 10 days.

B46. The method of any one of claims B1-B41, wherein the effective amount of cytarabine in the second course of treatment is 40 mg/m$^2$ once daily or 20 mg/m$^2$ twice daily for 10 days.

B47. The method of any one of claims B1-B46, wherein the alvocidib in the first course of treatment, in the third course of treatment, or both is administered by intravenous infusion.

B48. The method of claim B47, wherein the alvocidib in the first course of treatment, in the third course of treatment, or both is administered as a 15-minute to one-hour intravenous bolus.

B49. The method of claim B48, wherein the alvocidib in the first course of treatment, in the third course of treatment, or both is administered as a 30-minute intravenous bolus.

B50. The method of any one of claims B1-B49, wherein the cytarabine in the second course of treatment is administered by injection.

B51. The method of claim B50, wherein the cytarabine in the second course of treatment is administered by subcutaneous injection.

B52. The method of any one of claims B1-B51, further comprising administering to the subject an effective amount of an intravenous hydration fluid, allopurinol, a phosphate binder, or a combination thereof, at least prior to the first dose of alvocidib.

B53. The method of any one of claims B1-B52, further comprising administering to the subject an effective amount of an antibiotic, an anti-viral agent, an anti-fungal agent, or a combination thereof.

B54. The method of any one of claims B1-B53, wherein the subject is MCL-1 dependent.

B55. The method of any one of claims B1-B54, wherein the subject is identified as MCL-1 dependent.

B56. The method of claim B55, wherein the subject is identified as MCL-1 dependent by examining a bone marrow sample of the subject.

B57. The method of claim B5, wherein the compound of Formula (I-b), or pharmaceutically acceptable salt thereof, is administered to the subject orally.

B58. The method of any one of claims B1-B57, wherein the subject is measurable residual disease (MRD)-positive prior to being administered the first, second and third courses of treatment.

B59. The method of any one of claims B1-B58, wherein the subject is measurable residual disease (MRD)-negative after being administered the first, second and third courses of treatment.

B60. The method of any one of claims B1-B59, further comprising detecting the measurable residual disease (MRD) status of the subject.

B61. The method of claim B60, wherein the MRD status of the subject is detected prior to administering the first, second and third courses of treatment to the subject.

B62. The method of claim B60, wherein the MRD status of the subject is detected after administering the first, second and third courses of treatment to the subject.

B63. The method of any one of claims B60-B62, wherein the MRD status of the subject is detected prior to and after administering the first, second and third courses of treatment to the subject.

B64. The method of any one of claims B1-B63, further comprising terminating administration of at least the first and third courses of treatment to the subject if the subject is determined to be measurable residual disease (MRD)-negative.

C1. A method for treating acute myeloid leukemia (AML) in a subject in need thereof, the method comprising, in the absence of venetoclax:

(i) administering to the subject an effective amount of decitabine or azacitidine in a first course of treatment; and (ii) administering to the subject an effective amount of alvocidib in a second course of treatment;

wherein the subject has refractory, resistant, or relapsed AML after one or more prior therapies, at least one of which comprises venetoclax.

C2. The method of claim C1, wherein the one or more prior therapies further comprise one or more other therapeutic agents for treating AML.

C3. The method of claim C2, wherein the one or more other therapeutic agents comprise azacitibine, decitabine, or a combination thereof.

C4. The method of any one of claims C1-C3, wherein the alvocidib is a compound having the structure of Formula (I):

(I)

[Chemical structure of Formula (I): a chromone with OH, O, HO, HO substituents, an H-bearing stereocenter connected to a piperidine ring with N-methyl, and a 2-chlorophenyl group attached via oxygen]

or a pharmaceutically acceptable salt thereof.

C5. The method of any one of claims C1-C4, wherein the alvocidib is a compound having the structure of Formula (I-b):

(I-b)

[Chemical structure of Formula (I-b): similar to Formula (I) but with a phosphate group (HO)(HO)P(=O)O- on the chromone ring]

or a pharmaceutically acceptable salt thereof.

C6. The method of any one of claims C1-C5, wherein the effective amount of the alvocidib is from about 20 mg/m$^2$ to about 150 mg/m$^2$ once per day.

C7. The method of claim C6, wherein the alvocidib is administered to the subject as a 15-minute to one-hour intravenous bolus.

C8. The method of claim C6, wherein a portion of the alvocidib is administered to the subject as a 15-minute to one-hour intravenous bolus, and the remaining alvocidib is administered to the subject by intravenous infusion in about 3 to about 6 hours.

C9. The method of any one of claims C1-C8, wherein the effective amount of the decitabine is about 15 mg/m$^2$ to about 40 mg/m$^2$ once every day.

C10 The method of any one of claims C1-C9, wherein the decitabine is administered to the subject by intravenous infusion.

C11. The method of any one of claims C1-C10, wherein the effective amount of azacitidine is from about 50 mg/m$^2$ to about 100 mg/m$^2$ once every day.

C12. The method of any one of claims C1-C11, wherein the azacitidine is administered to the subject by intravenous injection or subcutaneous injection.

C13. The method of any one of claims C1-C12, wherein the method comprises one or more treatment cycles, each treatment cycle comprising:
(i) administering to the subject (a) the decitabine at from about 15 mg/m$^2$ to about 40 mg/m$^2$ once every day for 3-10 days, or (b) the azacitidine at from about 50 mg/m$^2$ to about 100 mg/m$^2$ once every day for 3-10 days; followed by a drug holiday period of about 1 to about 4 days; and
(ii) administering to the subject the alvocidib at a dose of about 20 mg/m$^2$ to about 100 mg/m$^2$ once per day for 1-3 days.

C14. The method of claim C13, wherein each treatment cycle consists of 28 days, and comprises:
(i) administering to the subject the decitabine at about 20 mg/m$^2$ once every day on Days 1-5; followed by a first drug holiday period on Days 6 and 7; and
(ii) administering to the subject the alvocidib at a dose of from about 20 mg/m$^2$ to about 100 mg/m$^2$ on Day 8; followed by a second drug holiday period on Days 9-28.

C15. The method of claim C13, wherein each treatment cycle consists of 28 days, and comprises:
(i) administering to the subject the azacitidine at about 75 mg/m$^2$ once every day on Days 1-5; followed by a first drug holiday period on Days 6 and 7; and
(ii) administering to the subject the alvocidib at a dose of from about 20 mg/m$^2$ to about 100 mg/m$^2$ on Day 8; followed by a second drug holiday period on Days 9-28.

C16. The method of any one of claims C1-C15, wherein the subject is MCL-1 dependent.

C17. The method of any one of claims C1-C16, wherein the subject is identified as MCL-1 dependent.

C18. The method of claim C17, wherein the subject is identified as MCL-1 dependent by examining a bone marrow sample of the subject.

C19. The method of claim C5, wherein the compound of Formula (I-b), or pharmaceutically acceptable salt thereof, is administered to the subject orally.

C20. The method of any one of claims C1-C19, wherein the subject is measurable residual disease (MRD)-positive prior to being administered the second course of treatment.

C21. The method of any one of claims C1-C20, wherein the subject is measurable residual disease (MRD)-negative after being administered the second course of treatment.

C22. The method of any one of claims C1-C21, further comprising detecting the measurable residual disease (MRD) status of the subject.

C23. The method of claim C22, wherein the MRD status of the subject is detected prior to administering the second course of treatment to the subject.

C24. The method of claim C22, wherein the MRD status of the subject is detected after administering the second course of treatment to the subject.

C25. The method of any one of claims C22-C24, wherein the MRD status of the subject is detected prior to and after administering the second course of treatment to the subject.

C26. The method of any one of claims C1-C25, further comprising terminating administration of at least the second course of treatment to the subject if the subject is determined to be measurable residual disease (MRD)-negative.

D1. A method for inhibiting development of tumor lysis syndrome (TLS) in a subject having a hematological cancer, the method comprising administering to the subject alvocidib and, optionally, cytarabine, in the absence of venetoclax, following the conditions set forth in any one of the preceding claims, wherein the subject has refractory, resistant, or relapsed hematological cancer after one or more prior therapies, at least one of which comprises venetoclax.

D2. A method of reducing the severity of tumor lysis syndrome (TLS) in a subject having a hematological cancer and being treated with alvocidib, the method comprising administering to the subject an effective amount of alvocidib and, optionally, cytarabine, in the absence of venetoclax, following the conditions set forth in any one of the preceding claims, wherein the subject has refractory, resistant, or relapsed hematological cancer after one or more prior therapies, at least one of which comprises venetoclax.

D3. A method of treating tumor lysis syndrome (TLS) in a subject having a hematological cancer and being treated with alvocidib, the method comprising administering to the subject an effective amount of alvocidib and, optionally, cytarabine, in the absence of venetoclax, following the conditions set forth in any one of the preceding claims, wherein the subject has refractory, resistant, or relapsed hematological cancer after one or more prior therapies, at least one of which comprises venetoclax.

D4. A method of decreasing mortality from tumor lysis syndrome (TLS) in a subject having a hematological cancer and being treated with alvocidib, the method comprising administering to the subject an effective amount of alvocidib and, optionally, cytarabine, in the absence of venetoclax, following the conditions set forth in any one of the preceding claims, wherein the subject has refractory, resistant, or relapsed hematological cancer after one or more prior therapies, at least one of which comprises venetoclax.

D5. A method of reducing the incidence of tumor lysis syndrome (TLS) in a subject having a hematological cancer and being treated with alvocidib, the method comprising administering to the subject an effective amount of alvocidib and, optionally, cytarabine, in the absence of venetoclax, following the conditions set forth in any one of the preceding claims, wherein the subject has refractory, resistant, or relapsed hematological cancer after one or more prior therapies, at least one of which comprises venetoclax.

D6. A method of preventing tumor lysis syndrome (TLS) in a subject having a hematological cancer and being treated with alvocidib, the method comprising administering to the subject an effective amount of alvocidib and, optionally, cytarabine, in the absence of venetoclax, following the conditions set forth in any one of the preceding claims, wherein the subject has refractory, resistant, or relapsed hematological cancer after one or more prior therapies, at least one of which comprises venetoclax.

D7. A method of treating a hematological cancer in a subject without high risk for developing tumor lysis syndrome (TLS), the method comprising administering to the subject an effective amount of alvocidib and, optionally, cytarabine, in the absence of venetoclax, following the conditions set forth in any one of the preceding claims, wherein the subject has refractory, resistant, or relapsed hematological cancer after one or more prior therapies, at least one of which comprises venetoclax.

D8. The method of any one of claims D1-D7, wherein the hematological cancer is acute myeloid leukemia (AML).

D9. The method of any one of claims D1-D8, wherein the subject is identified as at risk for developing TLS.

D10. The method of any one of claims D1-D9, wherein the one or more prior therapies further comprise one or more other therapeutic agents for treating AML.

D11. The method of claim D10, wherein the one or more other therapeutic agents comprise azacitidine, decitabine, or a combination thereof.

E1. A method for treating acute myeloid leukemia (AML) in a subject in need thereof, the method comprising, in the absence of venetoclax:
  (i) administering to the subject an effective amount of alvocidib in a first course of treatment;
  (ii) administering to the subject cytarabine at a daily dose of about 500 mg/m² to about 3 g/m² in a second course of treatment; and
  (iii) administering to the subject an effective amount of alvocidib in a third course of treatment;
wherein the subject has refractory, resistant, or relapsed AML after one or more prior therapies, at least one of which comprises venetoclax.

E2. The method of claim E1, wherein the one or more prior therapies further comprise one or more other therapeutic agents.

E3. The method of claim E2, wherein the one or more other therapeutic agents comprise decitabine, azacitidine, or a combination thereof.

E4. The method of any one of claims E1-E3, wherein the effective amount of the cytarabine in the second course of treatment is about 1 g/m² per day.

E5. The method of any one of claims E1-E4, wherein the second course of treatment consists of 3-8 days.

E6. The method of claim E5, wherein the second course of treatment consists of 5 days.

E7. The method of any one of claims E1-E6, wherein step (i) and step (iii) are performed as set forth in any one of claims B7-B11, B17-B22, B29-B36, and B46-B48.

E8. The method of any one of claims E1-E7, wherein the subject is MCL-1 dependent.

E9. The method of any one of claims E1-E8, wherein the subject is identified as MCL-1 dependent.

E10. The method of claim E9, wherein the subject is identified as MCL-1 dependent by examining a bone marrow sample of the subject.

E11. The method of any one of claims E1-E10, wherein the subject is measurable residual disease (MRD)-positive prior to being administered the first, second and third courses of treatment.

E12. The method of any one of claims E1-11, wherein the subject is measurable residual disease (MRD)-negative after being administered the first, second and third courses of treatment.

E13. The method of any one of claims E1-E12, further comprising detecting the measurable residual disease (MRD) status of the subject.

E14. The method of claim E13, wherein the MRD status of the subject is detected prior to administering the first, second and third courses of treatment to the subject.

E15. The method of claim E13, wherein the MRD status of the subject is detected after administering the first, second and third courses of treatment to the subject.

E16. The method of any one of claims E13-E15, wherein the MRD status of the subject is detected prior to and after administering the first, second and third courses of treatment to the subject.

E17. The method of any one of claims E1-E16, further comprising terminating administration of at least the first and third courses of treatment to the subject if the subject is determined to be measurable residual disease (MRD)-negative.

F1. A method for treating acute myeloid leukemia (AML) in a subject in need thereof, the method comprising, in the absence of venetoclax and mitoxantrone:
  (i) administering to the subject an effective amount of alvocidib in a first course of treatment; and
  (ii) administering to the subject an effective amount of cytarabine in a second course of treatment;
wherein the subject has refractory, resistant, or relapsed AML after one or more prior therapies, at least one of which comprises venetoclax.

F2. The method of claim F1, wherein the one or more prior therapies further comprise one or more other therapeutic agents for treating AML.

F3. The method of claim F2, wherein the one or more other therapeutic agents comprise azacitidine, decitabine, or a combination thereof.

F4. The method of any one of claims F1-F3, wherein step (i) is performed following step (ii).

F5. The method of any one of claims F1-F4, wherein the effective amount of cytarabine in the second course of treatment is from about 10 mg/m$^2$ to about 100 mg/m$^2$ per day.

F6. The method of claim F5, wherein the effective amount of cytarabine in the second course of treatment is about 20 mg/m$^2$ per day.

F7. The method of any one of claims F1-F6, wherein the second course of treatment consists of 8-12 days.

F8. The method of any one of claims F1-F7, wherein step (i) comprises administering to the subject the alvocidib at a dose of from about 25 mg/m$^2$ to about 100 mg/m$^2$ per day for about 1-4 days.

F9. The method of claim F8, wherein alvocidib is administered to the subject at a dose of 50 mg/m$^2$ per day as an intravenous bolus in about 30 minutes once every day for 3 days.

F10. The method of any one of claims F1-F3, wherein step (i) is performed before step (ii).

F11. The method of claim F10, wherein step (i) comprises administering the alvocidib to the subject at a daily dose of from about 80 mg/m$^2$ to about 120 mg/m$^2$.

F12. The method of claim F11, wherein in step (i), alvocidib is administered to the subject once per day for three consecutive days, followed by a drug holiday period of 2 days.

F13. The method of any one of claims F10-F12, wherein step (ii) comprises administering to the subject cytarabine at a dose of about 1 g/m$^2$ to about 3 g/m$^2$ by intravenous injection in about 72 hours.

F14. The method of any one of claims F1-F13, wherein the subject is MCL-1 dependent.

F15. The method of any one of claims F1-F14, wherein the subject is identified as MCL-1 dependent.

F16. The method of claim F15, wherein the subject is identified as MCL-1 dependent by examining a bone marrow sample of the subject.

F17. The method of any one of claims F1-F16, wherein the subject is measurable residual disease (MRD)-positive prior to being administered the first and second courses of treatment.

F18. The method of any one of claims F1-F17, wherein the subject is measurable residual disease (MRD)-negative after being administered the first and second courses of treatment.

F19. The method of any one of claims F1-F18, further comprising detecting the measurable residual disease (MRD) status of the subject.

F20. The method of claim F19, wherein the MRD status of the subject is detected prior to administering the first and second courses of treatment to the subject.

F21. The method of claim F19, wherein the MRD status of the subject is detected after administering the first and second courses of treatment to the subject.

F22. The method of any one of claims F18-F20, wherein the MRD status of the subject is detected prior to and after administering the first and second courses of treatment to the subject.

F23. The method of any one of claims F1-F22, further comprising terminating administration of at least the first course of treatment to the subject if the subject is determined to be measurable residual disease (MRD)-negative.

Example 1. Alvocidib Monotherapy

Provided herein is a prophetic example describing an exemplary alvocidib monotherapy regimen for treating AML with venetoclax failure.

Human patients having primary refractory AML after up to 2 cycles of venetoclax treatment or having relapsed AML with a First Complete Remission (CR1) period of >90 days to ≤18 months after venetoclax treatment can be subject to this monotherapy.

The monotherapy includes 4-8 treatment cycles, each of which includes 28 days (4 weeks). In each treatment cycle, alvocidib is given to the AML patient at a dose of 25 mg/m$^2$ via an intravenous bolus of 30 minutes on Day 1 of Week 1. In Weeks 2 and 3 (e.g., on Day 1 of Week 2 and Day 1 of Week 3), alvocidib is given to the AML patient at a dose of 50 mg/m$^2$ via an intravenous bolus for 30 minutes. The patient then has a 1-week alvocidib-free (drug holiday) period.

Example 2. Alvocidib in Combination with Low Dose Cytarabine

This is a prophetic example describing a Phase 2, open label, clinical study in patients with AML, who have progressed due to resistance or relapse (i.e., after complete remission) following treatment with venetoclax, either alone or in combination with azacitidine or decitabine.

In this study, the human subjects were previously treated with venetoclax, optionally in combination with azacitidine or decitabine, and were considered ineligible for induction therapy, including:
a. ≥75 years of age
b. ≥18 to 65 years of age with at least one of the following comorbidities that preclude use of intensive induction chemotherapy:
   i. Eastern Cooperative Oncology Group (ECOG) Performance Status of 2 or 3;
   ii. Cardiac history of Congestive Heart Failure (CHF) requiring treatment or Ejection Fraction≤50% or chronic stable angina;
   iii. Diffusing capacity of the Lung for Carbon Monoxide (DLCO)<=65% or Forced Expiratory Volume in 1 second (FEV1)≤65%;
   iv. Creatinine clearance≥30 mL/min to <45 ml/min;
   v. Moderate hepatic impairment with total bilirubin>1.5 to ≤3.0×Upper Limit of Normal (ULN);
   vi. Any other comorbidity that the physician judges to be incompatible with intensive chemotherapy must be reviewed and approved by the Therapeutic Medical Director during screening and before study enrollment.

Provide written informed consent prior to any study related procedure. (In the event that the patient is re-screened for study participation or a protocol amendment alters the care of an ongoing patient, a new informed consent form must be signed.)

To be eligible for participation in the study, patients must meet all of the following inclusion criteria:
1. Be ≥18 years of age
2. Have an established, pathologically confirmed diagnoses of AML by World Health Organization (WHO) criteria excluding acute promyelocytic leukemia (APL-M3) with a bone marrow of >5% blasts based on histology or flow cytometry
3. Have demonstrated progression on prior venetoclax combined with azacitidine or decitabine 4. Have an Eastern Cooperative Oncology Group (ECOG) performance status (PS)≤2
5. Have a serum creatinine level≤1.8 mg/dL
6. Have an alanine aminotransferase (ALT)/aspartate aminotransferase (AST) level≤5 times upper limit of normal (ULN)
7. Have a total bilirubin level≤2.0 mg/dL (unless secondary to Gilbert syndrome, hemolysis, or leukemia)
8. Have a left ventricular ejection fraction (LVEF)>45% by echocardiogram (ECHO) or multigated acquisition (MUGA) scan
9. Be nonfertile or agree to use an adequate method of contraception. Sexually active patients and their partners must use an effective method of contraception associated with a low failure rate during and for 6 months after completion of study therapy Patients meeting any one of these exclusion criteria will be prohibited from participating in this study.

1. Received any previous treatment with alvocidib or any other CDK inhibitor
2. Require concomitant chemotherapy, radiation therapy, or immunotherapy Hydroxyurea is allowed up to the evening before starting (but not within 12 hours) of starting treatment on either arm
3. Have a peripheral blast count of >30,000/mm$^3$ (may use hydroxyurea as in #5 above)
4. Received antileukemic therapy within the last 3 weeks (with the exception of hydroxyurea or if the patient has definite refractory disease). Refractory patients who received therapy within the last 3 weeks may be eligible with prior approval of the Medical Monitor
5. Diagnosed with acute promyelocytic leukemia (APL, M3)
6. Have active central nervous system (CNS) leukemia
7. Have evidence of uncontrolled disseminated intravascular coagulation
8. Have an active, uncontrolled infection
9. Have other life-threatening illness
10. Have other active malignancies or diagnosed with other malignancies within the last 6 months, except nonmelanoma skin cancer or cervical intraepithelial neoplasia
11. Have mental deficits and/or psychiatric history that may compromise the ability to give written informed consent or to comply with the study protocol
12. Are pregnant and/or nursing
13. Have received any live vaccine within 14 days prior to first study drug administration The patients are given a combination therapy including 4-8 treatment cycles, each of which contains 28 days. Each treatment cycle consists of (i) alvocidib administered at a dose of 25 mg/m$^2$ as a 30 minute intravenous (IV) bolus daily on Day 1, followed by a first drug holiday period on Day 2; (ii) cytarabine administered at a dose of 20 mg/m$^2$ by subcutaneous injection on Days 3 through 12 (10 days) followed by 2 days of rest (a drug holiday period), and (iii) alvocidib administered at a dose of 50 mg/m$^2$ as a 30 minute intravenous (IV) bolus on Day 15, followed by 13 days of rest (on Days 16-28).

Supportive care is provided and includes the following: tumor lysis prevention and treatment (e.g., mandatory hydration with saline or similar hydration fluid); diligent monitoring of urine output; mandatory allopurinol orally each day of dosing during treatment cycle 1 (optional in subsequent cycles); mandatory oral phosphate binder to be started at the same time as initiation of IV hydration during cycle 1 (optional in subsequent cycles), unless contraindicated; evaluation of laboratory indicators of tumor lysis syndrome (TLS) during treatment cycle 1; monitoring fibrinogen levels at baseline and then as clinically indicated; and prophylactic antibiotic, antiviral, and/or antifungal therapy.

The efficacy assessments performed in the study include response assessments as defined by the International Working Group Criteria and 2017 European LeukemiaNet, safety assessments, treatment assessments, and pharmacodynamic assessments. The response assessments included complete remission rate, overall survival, combined complete remission rate (e.g., complete remission plus complete hematologic remission), combined response rate (e.g., complete remission plus complete hematologic remission plus partial remission), and event-free survival. Treatment assessments included bone marrow biopsies and/or aspirates performed before treatment and at hematologic recovery (i.e., absolute neutrophil count (ANC)>1000 µL and platelet count>100,000 µL) or Day 45, whichever occurred first. In addition, complete blood counts and chemistries are assessed daily during hospitalization for chemotherapy administration and weekly thereafter. Pharmacodynamic assessments include determination of MCL-1 dependence at baseline using bone marrow.

Example 3. Alvocidib in Combination with Hypomethylating Agents (HMA)

Provided herein is a prophetic example describing an exemplary alvocidib therapy in combination with an HMA agent such as decitabine or azacitidine for treating AML with venetoclax failure.

Human patients having primary refractory AML after up to 2 cycles of venetoclax treatment or having relapsed AML with a First Complete Remission (CR1) period of >90 days to ≤18 months after venetoclax treatment can be subject to this therapy.

The therapy described in this Example may contain multiple treatment cycles as needed, for example, 4-8 treatment cycles. Each treatment cycle includes 28 days (4 weeks). In each treatment cycle, decitabine may be given to a subject on a daily basis on Days 1-5 (may extend to up to 10 days in some instances) at a daily dose of from about 15 mg/m$^2$ to about 45 mg/m$^2$, preferably, about 20 mg/mgt. After a drug holiday period (e.g., having 1-4 days such as 2 days, e.g., on Day 6 and 7), alvocidib is given to the AML patient at a dose of from about 20 mg/m$^2$ to about 90 mg/m$^2$ via an intravenous injection for 1-4 days, for example, on Day 8. Alvocidib may be given to the subject as an intravenous bolus of 30 minutes. Alternatively, a portion of the daily dose may be given to the subject (e.g., between about 10 mg/m$^2$ and about 30 mg/m$^2$, such as about 20 mg/m$^2$) as an intravenous bolus for 30 minutes, and the remaining dose (e.g., between about 10 mg/m$^2$ to about 60 mg/m$^2$, such as about 10 mg/m$^2$, about 20 mg/m$^2$, about 30 mg/m$^2$, about 45 mg/m$^2$, or about 60 mg/m$^2$) can be given to the subject by intravenous infusion in about 3 to about 6 hours, such as about 4 hours. The subject can then have a drug holiday period of about 15 to about 25 days, for example, about 20 days (e.g., on Days 9-28).

Example 4. Phase 2 Study of Alvocidib in Patients With Relapsed/Refractory Acute Myeloid Leukemia Following Treatment with Venetoclax Combination Therapy This study will evaluate the safety and efficacy of alvocidib in patients with AML who have either relapsed from (e.g., experience reoccurrence of disease following a CR/CR$_i$ with duration of greater than or equal to 90 days) or are refractory to (e.g., failed to achieve a CR/CR$_i$, or achieved a CR/CR$_i$ with duration of less than 90 days) induction therapy with venetoclax in combination with azacytidine or decitabine.

The following inclusion criteria apply to this study:
1. Be ≥18 years of age.
2. Have an established, pathologically confirmed diagnosis of AML by World Health Organization (WHO) criteria, excluding acute promyelocytic leukemia (APL-M3) with a bone marrow of >5% blasts based on histology or flow cytometry.
3. Have received initial induction therapy with venetoclax in combination with azacytidine or decitabine and were either refractory (failed to achieve a CR/CRi or achieved a CR/CRi with duration<90 days) or have relapsed (reoccurrence of disease following a CR/CRi with duration≥90 days).
4. Have an Eastern Cooperative Oncology Group (ECOG) performance status (PS)≤2.
5. Have a glomerular filtration rate (GFR)≥30 mL/min using the Cockcroft-Gault equation.
6. Have an alanine aminotransferase (ALT)/aspartate aminotransferase (AST) level≤5 times upper limit of normal (ULN).
7. Have a total bilirubin level≤2.0 mg/dL (unless secondary to Gilbert syndrome, hemolysis, or leukemia).
8. Be infertile or agree to use an adequate method of contraception: sexually active patients and their partners must use an effective method of contraception associated with a low failure rate prior to study entry, for the duration of study participation, and for at least 3 months (males) and 6 months (females) after the last dose of study drug.
9. Be able to comply with the requirements of the entire study.
10. Provide written informed consent prior to any study related procedure: in the event that the patient is re-screened for study participation or a protocol amendment alters the care of an ongoing patient, a new informed consent form must be signed.

The following exclusion criteria apply to this study:
1. Received a previous treatment with alvocidib or another CDK inhibitor, or received prior anti-leukemic therapy other than first-line venteoclax in combination with azacytidine or decitabine.
2. Require concomitant chemotherapy, radiation therapy, or immunotherapy. Hydroxyurea is allowed up to the evening before starting (but not within 12 hours) of starting treatment on either arm.
3. Received an allogeneic stem cell transplant within 60 days of the start of study treatment. Patients who received an allogeneic stem cell transplant must be off all immunosuppressants at the time of study treatment.
4. Are receiving or have received systemic therapy for graft-versus-host disease.
5. Have a peripheral blast count of >30,000/mm$^3$ (may use hydroxyurea as in #2 above).
6. Received antileukemic therapy within the last 3 weeks (with the exception of hydroxyurea or if the patient has definite refractory disease). Refractory patients who received therapy within the last 3 weeks may be eligible with prior approval of the Medical Monitor.
7. Diagnosed with acute promyelocytic leukemia (APL-M3).
8. Have active central nervous system (CNS) leukemia.
9. Have evidence of uncontrolled disseminated intravascular coagulation.
10. Have an active, uncontrolled infection.
11. Have other life-threatening illness.
12. Have other active malignancies requiring treatment or diagnosed with other malignancies within the last 6 months, except nonmelanoma skin cancer or cervical intraepithelial neoplasia.
13. Have mental deficits and/or psychiatric history that may compromise the ability to give written informed consent or to comply with the study protocol.
14. Are pregnant and/or nursing.
15. Have received any live vaccine within 14 days prior to first study drug administration.

This is an open-label, randomized, two-stage clinical study. Stage 1 of the study is randomized, and consists of two arms (26 patients per arm). In Stage 1, 26 patients will be randomized into each of the two treatment arms stratified by prior response to venetoclax in combination with azacytidine or decitabine: refractory or relapsed.

As an additional safety measure, given the unique patient population and outpatient treatment administration, a lead-in cohort of six patients (three patients in each of the Stage 1 treatment arms) will be enrolled, treated and evaluated for dose-limiting toxicities (DLTs). Three patients in each arm of the lead-in cohort may be enrolled and treated simultaneously. In the absence of any dose-limiting toxicity (DLT), the study will proceed as outlined and randomization will begin into Arm 1 or Arm 2. If a patient in the lead-in cohort experiences a DLT during the first cycle, then the alvocidib doses for that patient will be reduced by 25% (to Dose Level −1), as shown in Table 1. That arm of the lead-in cohort will be expanded by at least one patient to determine whether the event was isolated in nature. If no additional DLTs are observed, the study will proceed as outlined. Once all 6 patients have been treated in the lead-in cohort with ≤1 DLT observed, patients will be accrued and randomized into Arm 1 or Arm 2. However, should ≥2 patients in a lead-in arm experience a DLT, a clinical meeting would be scheduled to discuss continuing the study as currently designed.

TABLE 1

| Stage | Study Drug Component | Dosing Days | Dose Level 1 | Dose Level -1[a] |
|---|---|---|---|---|
| 1 | | | | |
| Arm 1 | Alvocidib[b] | 1 | 25 mg/m$^2$ IV bolus | 19 mg/m$^2$ IV bolus |
| | Cytarabine | 3 through 12 | 20 mg/m$^2$ SC injection | 20 mg/m$^2$ SC injection |
| | Alvocidib[b] | 15 | 50 mg/m$^2$ IV bolus | 39 mg/m$^2$ IV bolus |
| Arm 2 | Alvocidib[b] | 1 | 25 mg/m$^2$ IV bolus | 19 mg/m$^2$ IV bolus |
| | Alvocidib | 8, 15 | 50 mg/m$^2$ IV bolus | 39 mg/m$^2$ IV bolus |

[a]Dose Level -1 to be used should a DLT be observed in the lead-in cohort of 6 patients (3 patients/treatment arm)
[b]Alvocidib to be administered as an IV bolus over 30 to 60 minutes Those patients in Arm 1 are given alvocidib and low dose cytarabine on a 28-day treatment cycle. On Day 1, patients in Arm 1 are given 25 mg/m$^2$ alvocidib as a 30-60-minute intravenous (IV) bolus. On Days 3 through 12 (10 days), patients in Arm 1 are given 20 mg/m$^2$ cytarabine by subcutaneous (SC) injection each day. On Day 15, patients in Arm 1 are given 50 mg/m$^2$ alvocidib as a 30-60-minute IV bolus. Those patients in Arm 2 of the study are given alvocidib on a 28-day treatment cycle. On Day 1, patients in Arm 2 are given 25 mg/m$^2$ alvocidib as a 30-60-minute IV bolus. On Days 8 and 15, patients in Arm 2 are given 50 mg/m² alvocidib as a 30-60-minute IV bolus.

Stage 2 of the study consists of 76 patients, who will be dosed with a regimen selected based on Stage 1 performance.

Patients who achieve CR, $CR_i$, $CR_h$, MLFS or PR after the first cycle (completion of all doses) may receive additional optional cycles of treatment until disease progression. Patients not demonstrating evidence of CR, $CR_i$, $CR_h$, MLFS or PR after 4 cycles of treatment will be considered for removal from the study, although with permission of the Medical Monitor, treatment may continue if clinically indicated and provided there is no evidence of toxicity≥NCI CTCAE Grade 4.

Supportive care may be provided, and may include the following: tumor lysis prevention and treatment (e.g., mandatory IV hydration with 0.45% NaCl (or similar hydration fluid per institutional standard) sterile solution at 500 cc for 1-2 hours prior to alvocidib, then an additional 500 cc for 1-2 hours after alvocidib during Cycle 1 (optional for subsequent cycles for patients who have achieved a CR)); replacement of excessive fluid losses, including from diarrhea, should be done unless otherwise clinically indicated (over-the-counter measures are typically effective in this setting if initiated early; persistent diarrhea despite optimal outpatient management would trigger medical consultation); mandatory oral allopurinol to be started at least 72 hours prior to Day 1 of Cycle 1 and continued until completion of the first cycle (i.e., 28 days) (this may be discontinued for subsequent treatment cycles if uric acid levels are within normal limits and there is no evidence of TLS); mandatory oral phosphate binder to be started at the same time as initiation of IV hydration on Day 1 of Cycle 1 and continued for the first week (i.e., 7 days) (this may be discontinued for subsequent treatment cycles if serum phosphorus levels are <3 after the first treatment with alvocidib and there is no evidence of TLS); evaluation of laboratory indicators of TLS during Cycle 1 (obtain a STAT serum potassium at the end of alvocidib infusion; tumor lysis laboratory evaluations (tumor lysis labs) include electrolytes (sodium, potassium, chloride, and carbon dioxide) as well as creatine, calcium, lactate dehydrogenase, uric acid, and phosphorous levels; monitor tumor lysis labs prior to infusion and two hours (±30 minutes) after completion of IV hydration post-alvocidib (labs will also be drawn daily for the first three days following the first alvocidib dose (Days 2-4, and at least weekly for the remainder of Cycle 1); during Cycles 2+, tumor lysis labs will be assessed prior to each dose of alvocidib; and monitor fibrinogen levels at baseline and then as clinically indicated); infection prevention (prophylactic antibiotics including levofloxacin (or equivalent) 500 mg orally once daily and azole antifungals (e.g., fluconazole, posaconazole, voriconazole, isavuconazole) should be administered to patients in all treatment arms if ANC<500/μL, and can be discontinued when the ANC≥500/μL per institutional standards and physician's discretion, valacyclovir (or equivalent) to be administered daily to all patients throughout the study based on institutional standards unless there are contraindications); routine growth factor support is not allowed; growth factor support can be given at the discretion of the Investigator and with the Medical Monitor's approval in the presence of life threatening infection with ongoing neutropenia; donor lymphocyte infusions are not allowed at any time during the study).

The efficacy assessments performed in the study include response assessments as defined by the International Working Group Criteria and 2017 European LeukemiaNet, safety assessments, treatment assessments, and pharmacodynamic assessments. The response assessments include complete remission rate; $CR_{MRD-}$, defined as patients achieving CR whose bone marrow is determined to be negative for MRD using standardized techniques (e.g., multiparametric flow cytometry, molecular testing including next generation sequencing); median overall survival (time from treatment (Day 1) until death from any cause); CR rate, defined as the percentage of patients achieving CR (defined as bone marrow blasts<5%, absence of blasts with Auer rods, absence of extramedullary disease, and hematologic recovery (absolute neutrophil count (ANC)≥1,000/μL and platelet count≥100,000/μL)); composite CR rate, defined as the percentage of patients achieving CR, $CR_i$ (defined as meeting all CR criteria but with only full recovery of one peripheral blood cell type (ANC≥1,000/μL or platelet count≥100,000/μL)) or $CR_h$ (defined as CR with only partial recovery of both peripheral blood cell types (ANC≥500/μL and platelet count≥50,000/μL); combined response rate, defined as the combined percentage of patients achieving at least one of the following: CR, $CR_i$, $CR_h$, morphologic leukemia free state (MLFS; bone marrow blasts of less than 5%, absence of blasts with Auer rods, absence of extramedullary disease, no hematologic recovery required) and partial remission (PR; meets all hematologic values required for CR, but with a decrease of at least 50% in the percentage of blasts to greater than or equal to 5% to less than or equal to 25% in bone marrow); event-free survival (EFS; time from first treatment (Day 1) until (a) treatment failure, (b) relapse after CR, $CR_i$ or $CR_h$, or (c) death from any cause, whichever occurs first, censored at 2 years); duration of composite CR, defined as time from first documented response of CR, $CR_i$ or $CR_h$ to relapse or death from any cause; rates of 28- and 56-day transfusion independence (TI; defined as percentages of patients who do not receive red blood cell (RBC) transfusions, platelet (PLT) transfusions, or RBC and PLT transfusions for 28 days and 56 days, respectively).

Safety and tolerability of the regimen will be assessed by analyzing the incidence rates of treatment-emergent adverse events (TEAEs) summarized at the MedDRA preferred term and primary system organ class levels. Similar summaries will be made for subsets of adverse events (AEs) such as (1) those judged by the Investigator to be related to study treatment, and (2) serious adverse events (SAEs).

Safety and tolerability of the regimen will be assessed by analyzing the incidence rates of treatment-emergent adverse events (TEAEs) summarized at the MedDRA preferred term and primary system organ class levels. Similar summaries will be made for subsets of adverse events (AEs) such as (1) those judged by the Investigator to be related to study treatment, and (2) serious adverse events (SAEs).

Other routine safety assessments (e.g., clinical laboratory parameters and vital signs) will be summarized by shift tables and treatment group using mean, standard deviation, median, minimum and maximum changes from baseline values.

Mortality (all causes) at 30 and 60 days following last treatment will also be calculated.

Adverse events will be graded according to National Cancer Institute's Common Terminology Criteria for Adverse Events (NCI CTCAE), version 5.0.

A Data Safety Monitoring Board (DSMB) will monitor key outcomes from the study.

Other Embodiments

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for treating acute myeloid leukemia (AML) in a subject in need thereof, the method comprising administering an effective amount of alvocidib to the subject in the absence of venetoclax, wherein the subject has refractory, resistant, or relapsed AML after one or more prior therapies, at least one of which comprises venetoclax and a hypomethylating agent.

2. The method of claim 1, wherein the hypomethylating agent is azacitidine, decitabine, or azacitidine and decitabine.

3. The method of claim 1, wherein the one or more prior therapies comprising venetoclax and a hypomethylating agent is an induction therapy.

4. The method of claim 1, wherein the alvocidib is a compound having the structure of Formula (I):

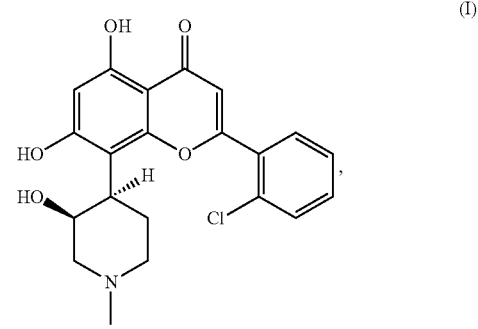 [SMILES: CN1CC[C@H](c2c(O)cc(O)c3c(=O)cc(-c4ccccc4Cl)oc23)[C@H](O)C1]

or a pharmaceutically acceptable salt thereof.

5. The method of claim 1, wherein the alvocidib is a compound having the structure of Formula (I-b):

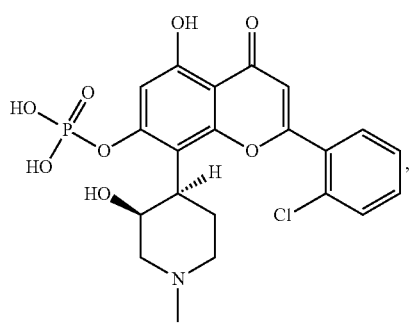

or a pharmaceutically acceptable salt thereof.

6. A method for treating acute myeloid leukemia (AML) in a subject in need thereof, the method comprising, in the absence of venetoclax:
(i) administering to the subject an effective amount of alvocidib in a first course of treatment;
(ii) administering to the subject an effective amount of cytarabine in a second course of treatment; and
(iii) administering to the subject an effective amount of alvocidib in a third course of treatment;
wherein the subject has refractory, resistant, or relapsed AML after one or more prior therapies, at least one of which comprises venetoclax and a hypomethylating agent.

7. The method of claim 1, comprising administering to the subject an effective amount of alvocidib in the absence of an additional chemotherapeutic agent for AML, wherein the subject has refractory, resistant, or relapsed AML after an induction therapy comprising venetoclax and a hypomethylating agent.

8. The method of claim 7, wherein the alvocidib is a compound having the structure of Formula (I):

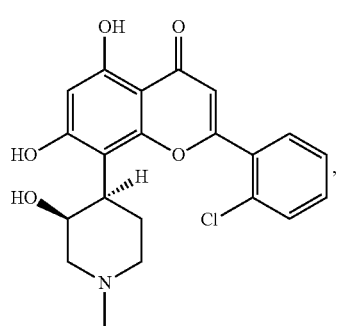

or a pharmaceutically acceptable salt thereof.

9. The method of claim 8, wherein:
from about 15 mg/m² to about 40 mg/m² of the alvocidib is administered by intravenous bolus on day 1 of a 28-day treatment cycle; and
from about 40 mg/m² to about 80 mg/m² of the alvocidib is administered by intravenous bolus on days 8 and 15 of the 28-day treatment cycle.

10. The method of claim 7, comprising administering to the subject, in the absence of an additional chemotherapeutic agent for AML:
from about 15 mg/m² to about 40 mg/m² of a compound having the structure of Formula (I):

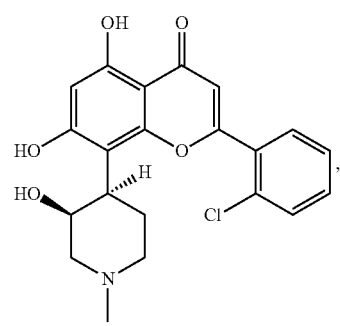

or a pharmaceutically acceptable salt thereof, by intravenous bolus on day 1 of a 28-day treatment cycle; and
from about 40 mg/m² to about 80 mg/m² of the compound having the structure of Formula (I), or a pharmaceutically acceptable salt thereof, by intravenous bolus on days 8 and 15 of the 28-day treatment cycle,
wherein the subject has refractory, resistant, or relapsed AML after an induction therapy comprising venetoclax and azacitidine or venetoclax and decitabine.

11. The method of claim 10, wherein:
about 25 mg/m² of the alvocidib is administered by intravenous bolus on day 1 of a 28-day treatment cycle; and
about 50 mg/m² of the alvocidib is administered by intravenous bolus on days 8 and 15 of the 28-day treatment cycle.

12. The method of claim 1, comprising administering to the subject an effective amount of alvocidib and low-dose cytarabine in the absence of an additional chemotherapeutic agent for AML, wherein the subject has refractory, resistant, or relapsed AML after an induction therapy comprising venetoclax and a hypomethylating agent.

13. The method of claim 12, wherein the alvocidib is a compound having the structure of Formula (I):

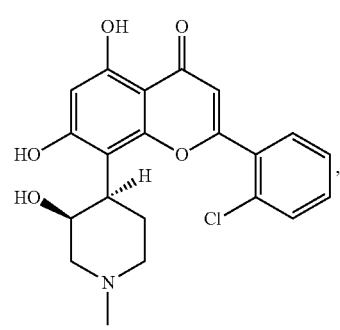

or a pharmaceutically acceptable salt thereof.

14. The method of claim 13, wherein:
from about 15 mg/m² to about 40 mg/m² of the alvocidib is administered by intravenous bolus on day 1 of a 28-day treatment cycle; and
from about 40 mg/m² to about 80 mg/m² of the alvocidib is administered by intravenous bolus on day 15 of the 28-day treatment cycle.

15. The method of claim 14, wherein:
from about 10 mg/m² to about 100 mg/m² cytarabine is administered per day by injection on days 3, 4, 5, 6, 7, 8, 9, 10, 11 and 12 of the 28-day treatment cycle.

16. The method of claim 12, comprising administering to the subject, in the absence of an additional chemotherapeutic agent for AML:
from about 15 mg/m² to about 40 mg/m² of a compound having the structure of Formula (I):

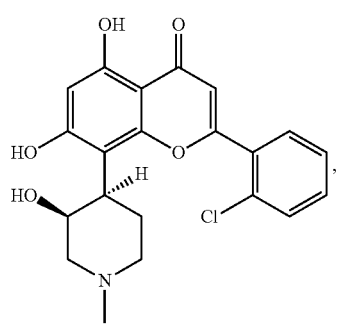

or a pharmaceutically acceptable salt thereof, by intravenous bolus on day 1 of a 28-day treatment cycle;
from about 10 mg/m² to about 100 mg/m² cytarabine, per day by injection on days 3, 4, 5, 6, 7, 8, 9, 10, 11 and 12 of the 28-day treatment cycle; and
from about 40 mg/m² to about 80 mg/m² of the compound having the structure of Formula (I), or a pharmaceutically acceptable salt thereof, by intravenous bolus on days 8 and 15 of the 28-day treatment cycle,
wherein the subject has refractory, resistant, or relapsed AML after an induction therapy comprising venetoclax and azacitidine or venetoclax and decitabine.

17. The method of claim 16, wherein:
about 25 mg/m² of the alvocidib is administered by intravenous bolus on day 1 of a 28-day treatment cycle; and
about 50 mg/m² of the alvocidib is administered by intravenous bolus on day 15 of the 28-day treatment cycle.

18. The method of claim 16, wherein:
about 20 mg/m² cytarabine is administered per day by injection on days 3, 4, 5, 6, 7, 8, 9, 10, 11 and 12 of the 28-day treatment cycle.

19. The method of claim 1, wherein the subject is a human.

20. A method for inhibiting development of tumor lysis syndrome (TLS) in a subject; reducing the severity of TLS in a subject decreasing mortality from TLS in subjects; reducing the incidence of TLS in subjects; preventing TLS in a subject; or treating AML in a subject without high risk for developing TLS, the method comprising administering alvocidib to the subject at a first dose of from about 15 mg/m² to about 40 mg/m² in the absence of venetoclax, wherein the subject has refractory, resistant, or relapsed AML after one or more prior therapies, at least one of which comprises venetoclax.

* * * * *